United States Patent [19]
Comberbach et al.

[11] Patent Number: 6,103,519
[45] Date of Patent: Aug. 15, 2000

[54] ANTIGENS AND METHODS THEREFOR

[75] Inventors: Martin Comberbach, La Hulpe; Nigel Harford, Overijse; Teresa Cabezon, Rhode-St-Genese; Apolonia Rutgers, Genval; Pierre Voet, Izel, all of Belgium; Eric Jacobs, Bas-Rhin, France; Cornelis P. Hollenberg, Dusseldorf, Germany; Zbigniew A. Janowicz, Erkrath, Germany; Armin J. Merckelbach, Dusseldorf, Germany

[73] Assignee: SmithKline Biologicals, S.A., Rixensart, Belgium

[21] Appl. No.: 08/443,054

[22] Filed: May 17, 1995

Related U.S. Application Data

[63] Continuation of application No. 08/399,391, Mar. 6, 1995, which is a continuation of application No. 08/179,799, Jan. 11, 1994, abandoned, which is a continuation of application No. 07/914,177, Jul. 14, 1992, abandoned, which is a continuation of application No. 07/556,933, Jul. 23, 1990, abandoned, which is a continuation of application No. 07/389,184, Aug. 3, 1989, abandoned.

[51] Int. Cl.$^7$ ............................. A61K 39/29; A61K 39/00
[52] U.S. Cl. ................... 435/320.1; 435/69.1; 435/69.3; 536/23.72
[58] Field of Search ................................. 435/69.3, 69.1, 435/320.1; 536/23.72

[56] References Cited

U.S. PATENT DOCUMENTS

| | | |
|---|---|---|
| 4,722,840 | 2/1988 | Valenzuela et al. . |
| 4,769,238 | 9/1988 | Rutter et al. . |
| 5,389,525 | 2/1995 | Hollenberg et al. ............... 435/69.1 |
| 5,650,296 | 7/1997 | Thill .................................. 435/69.3 |

FOREIGN PATENT DOCUMENTS

| | | |
|---|---|---|
| 288 198 | of 0000 | European Pat. Off. . |
| 0288 198 | 10/1988 | European Pat. Off. ........ C12N 15/00 |
| 0304578 | 1/1989 | European Pat. Off. ........ C12N 15/00 |
| 299101 | 1/1989 | European Pat. Off. ........ C12N 15/00 |
| 414374A3 | 7/1990 | European Pat. Off. . |

OTHER PUBLICATIONS

Burrell, et al. Expression in Escherichia coli of hepatitis B virus DNA sequences cloned in plasmid pBR322, Nature 279, 43–47 (1979).

Charnay, et al. Cloning in Escherichia coli and physical structure of hepatitis B virion DNA. Proc. Natl. Acad. Sci. USA 76, 2222–2226 (1979).

Cregg, et al. Pichia pastoris as a Host System for Transformations. Mol. Cell. Biol. 5, 3376–3385 (1985).

Dehoux, et al. Expression of the hepatitis B virus large envelope protein in Saccharomyces cerevisiae. Gene 48, 155–163 (1986).

Eble, et al. Hepatitis B Surface Antigen: an Unusual Secreted Protein Initially Synthesized as a Transmembrane Polypeptide. Mol. Cell. Biol. 6, 1454–63 (1986).

Ellis, et al. Isolation of Alcohol Oxidase and Two Other Methanol Regulatable Genes from the Yeast Pichia pastoris. Mol. Cell. Biol. 5, 1111–1121 (1985).

Galibert, et al. Nucleotide sequence of the hepatitis B virus genome (subtype ayw) cloned in E. coli. Nature 281, 646–650 (1979).

Grindley, et al. Genetic and DNA sequence analysis of the kanamycin resistance transposon Tn903. Proc. Natl. Acad. Sci USA 77, 7176–7180 (1980).

Harford, et al. Construction and characterization of a Saccharomyces cerevisiae strain (RIT4376) expressing hepatitis B surface antigen. Postgrad. Medical J. 63, Suppl. 2. 65–70 (1987).

Heermann, et al. Large Surface Proteins of Hepatitis B Virus Containing the Pre–s Sequence. J. Virol. 52, 396–402 (1984).

Hitzmann, et al. Expression for a human gene for interferon in yeast. Nature 293, 717–722 (1981).

Imamura, et al. Expression of Hepatitis B Virus Middle and Large Surface Antigen Genes in Saccharomyces cerevisiae. J. Virology 61, 3543–3549 (1987).

Itoh, et al. Expression of Hepatitis B Virus Surface Antigen P31 Gene in Yeast. Biochem. Biophys. Res. Comm. 138, 268–274(1986).

Jacobs, et al. Retrovirus–like vectors for Saccharomyces cerevisiae: integration of foreign genes controlled by efficient promoters into yeast chromosomal DNA. Gene 67, 259–269 (1988).

Janowicz, et al. Cloning and characterization of the DAS gene encoding the major methanol assimilatory enzyme from the methylotrophic yeast Hansenula polymorpha. Nucl. Acid Res. 13, 3043–3062 (1985).

Jimenez and Davies, Expression of a transposable antibiotic resistance element in Saccharomyces. Nature 287, 869–871 (1980).

(List continued on next page.)

*Primary Examiner*—Michael P. Woodward
*Assistant Examiner*—Mary V. Zeman
*Attorney, Agent, or Firm*—Zoltan Kerekes; Stephen Venetianer; Charles M. Kinzig

[57] ABSTRACT

A composite particle comprising at least two polypeptides corresponding to all or part of a protein having the biological activity of one of the hepatitis B surface antigens, wherein the particle presents at least two antigenic determinants provided by the S-protein, preS2-protein or preS1-protein, said particle optionally further comprising host specific lipids. The invention also provides a modified hepatitis B surface antigen L protein which may be used alone or incorporated into such composite particles.

A particular embodiment of the modified L protein (L*) comprises residues 12–52 followed by residues 133–145 followed by residues 175–400 of the L protein and a particular embodiment of a composite particle has the form (L*, S) where S is the S-protein of HBsAg.

Improved hepatitis B vaccines may be prepared following expression of the above immunogens, especially in yeasts such as *S. cerevisiae* and *Hansenula polymorpha*.

17 Claims, 15 Drawing Sheets

OTHER PUBLICATIONS

Klebe, et al. A general method for polyethylene–glycol–induced genetic transformation of bacterial and yeast. Gene 25,333–341 (1983).

Kniskern, et al. A Candidate Vaccine for Hepatitis B Containing the Complete Viral Surface Protein. Hepatology 8, 82–87 (1988).

Kohler and Milstein, Continuous cultures of fused cells secreting antibody of predefined specificity. Nature 256, 495–497 (1975).

Laemmli. Cleavage of Structural Proteins during the Assembly of the Head of Bacteriophage T4. Nature 227, 680–685 (1970).

Langley, et al. Characterization of purified hepatitis B surface antigen containing pre–S(2) epitopes expressed in Saccharomyces cerevisiae. Gene 67, 229–245 (1988).

Ledeboer, et al. Molecular cloning and characterization of a gene coding for methanol oxidase in Hansenula polymorpha. Nucleic Acid Res. 13, 3063–3082 (1985).

Lowry, et al. Protein Measurement With the Folin Phenol Reagent. J. Biol. Chem. 193, 265–275 (1951).

Maxam and Gilbert. A new method for sequencing DNA. Proc. Natl. Acad. Sci. USA 74, 560–564 (1977).

Michel, et al. Synthesis in animal cells of hepatitis B surface antigen particles carrying a receptor for polymerized human serum albumin. Proc. Natl. Acad. Sci. USA 81, 7708–7712 (1984).

Milich, et al. Enhanced Immunogenicity of the Pre–S Region of Hepatitis B Surface Antigen. Science 228, 1195–1199 (1985).

Milich, et al. T– and B–cell recognition of hepatitis B viral antigens. Immunology Today 9, 380–386 (1988).

Ou, et al. Regulation of Secretion of the Hepatitis B Virus Major Surface Antigen by the PreS–1 Protein. J. Virol. 61, 782–786 (1987).

Persing, et al. A frameshift mutation in the pre–S region of the human hepatitis B virus genome allows production of surface antigen aprticles but eliminates binding to polymerized albumin. Proc. Natl. Acad. Sci. USA 82, 3440–44 (1985).

Pontisso, et al. Receptors for Polymerized Human Serum Albumin on Hepatitis B Virus Particles Detected by Radioimmunoassay: Changes in Receptor Activity in Serum During Acute and Chronic Infection. J. Virological Methods 6, 151–159 (1983).

Roggenkamp, et al. Transformation of the methylotrophic yeast Hansenula polymorpha by autonomous replication and integration vectors. Mol. Gen. Genetics 202, 302–308 (1986).

Rutgers, et al. Hepatitis B Surface Antigen as Carrier Matrix for the Repetitive Epitope of the Circumsporozoite Protein of Plasmodium Falciparum. Biotech. 6, 1065–1070 (1988).

Schwartz and Cantor. Separation of Yeast Chromosome–Sized DNAs by Pulsed Field Gradient Gel Electrophoresis. Cell 37, 67–75 (1984).

Sninsky, et al. Cloning and endonuclease mapping of the hepatitis B viral genome. Nature 279, 346–348 (1979).

Southern. Detection of Specific Sequences Among DNA Fragments Separated by Gel Electrophoresis. J. Mol. Biol. 98, 503–517 (1975).

Stinchcomb, et al. Eukaryotic DNA segments capable of autonomous replication. Proc. Natl. Sci. USA 77, 4559–4563 (1980).

Struhl, et al. High–frequency transformation of yeast: Autonomous replication of hybrid DNA molecules. Proc. Natl. Acad. Sci. USA 76, 1035–1039 (1979).

Szmuness, et al. Hepatitis B Vaccine. Demonstration of Efficacy in a Controlled Trial in a High–Risk Population in the United States. New England J. Med. 303, 833–841 (1980).

Tschumper and Carbon. Sequence of a yeast DNA fragment containing a chromosomal replicator and the TRP1 gene. Gene 10, 157–166 (1980).

Towbin, et al. Electrophoretic transfer of proteins from polyacrylamide gels to nitrocellulose sheets: Procedure and come application. Proc. Natl. Acad. Sci. USA 76, 4350–4354 (1979).

Valenzuela, et al. Nucleotide sequence of the gene coding for the major protein of hepatitis B virus surface antigen. Nature 280, 815–819 (1979).

Valenzuela, et al. Synthesis and assembly of hepatitis B virus surface antigen particles in yeast. Nature 298, 347–350 (1982).

Valenzuela, et al. Synthesis and Assembly in Yeast of Hepatitis B Surface Antigen Particles Containing the Polyalbumin Receptor. Biotech 3, 317–320 (1985).

Tiollais, et al, *Nature*, 317:489 (1985).

Stibbe, et al., *J. Virol*, 46:626–628 (1983.

Neurath, et al, *Science*, 224:392–394 (1984).

Neurath, et al, *Nature*, 315:154–156 (1985).

Machida, et al, *Gastroenterology*, 86:910–918 (1984).

Persing, et al, *Science*, 234:1388–1392 (1986).

Persing, et al, *J Virol*, 61(5):1672–1677 (1987).

Rutgers, et al, "Viral Hepatitis and Liver Disease," ed. A.J. Zuckerman, A.R. Liss, New York, pp. 304–308 (1988).

Valenzuela, et al, *Biotech*, 3:323 (1985).

Kingsman, et al *Biotech*, Gen.Eng.Rev., 3:377 (1985).

Delpeyroux, et al *J. Virol*, 1836–1839 (1988).

Itoh and Fujisawa, *Biochem. Biophys. Res. Commin*, 141:942–948 (1986).

Jacobs, et al, $14^{th}$ Int. Conf. Gent. And Mol. Biol. S153 (1988).

Itoh, et al., *Biochem. Biophys. Res. Commin.*, 141(3):942–948 (1986).

Milich, et al., *J. of Immunology*, 137(1):315–322 (1986).

Neurath, et al., *Vaccine*, 4:35–37 (1986).

Itoh, et al., *Proc. Natl. Acad. Sci.*, 83:9174–9178 (1986).

Milich, et al., *Nature*, 329:547–549 (1987).

Neurath, et al., *Cell*, 46:429–436 (1986).

Hadler, et al., *New Engl. J. Med.*, 315:209–215 (1986).

Cregg, et al., *Biotechnology*, 5:479 (1987).

Elfassi, E., et al., *J. Theor. Bio.*, 121:371–74 (1986).

Fujisawa, Y., et al., *Mol. Bio. Hep. B Viruses*, Col. Sp. Harbor, p. 62 (1988).

Hermann, K–H., et al., *Intervirology* 28:14–25 (1987).

Neurath, A.R., et al., *Ann. Inst. Pasteur*, 139:13–38 (1988).

ANTIGENS AND METHODS THEREFOR

This is a continuation of Ser. No. 08/399,391 filed Mar. 6, 1995, which is a continuation of application Ser. No. 08/179,799, now abandoned filed Jan. 11, 1994, which is a continuation of application Ser. No. 07/914,177, filed Jul. 14, 1992,now abandoned, which is a continuation of application Ser. No. 07/556,933, filed Jul. 23, 1990, now abandoned, which is a continuation of application Ser. No. 07/389,184, filed Aug. 3, 1989 now abandoned.

The invention relates to a microorganism selected from the group of methylotrophic yeast genera, a DNA molecule containing an expression cassette, a vector suitable for transformation of a methylotrophic yeast, a process for the preparation of a microorganism, a composite particle containing at least two polypeptides corresponding to all or part of a protein having the biological activity of hepatitis B surface antigen, a method for the preparation of composite particles and to compositions, vaccines and test kits containing same.

The invention also relates to the construction of microorganism strains synthesizing modified large surface proteins of hepatitis B virus, especially hepatitis B surface L antigens which are modified at various regions of the coding sequence to alter and enhance the biological activity thereof.

Hepatitis is a wide spread, serious infectious disease, which may be caused by several agents. One important cause was identified as hepatitis B virus (HBV), a small virion of about 43 nm diameter containing a genome which consists of a 3,200 base pair double-strained DNA circle having a single stranded gap of variable length. Infection with this virion results in an acute, sometimes fatal disease. Eighty five percent of affected persons recover after about three months of illness, about 1% suffers from acute necrosis of liver tissue, resulting in death within a short period, and about 10% suffer from a recurring outbreak of the disease. Approximately 4% of infected persons develop a chronic carrier state with an increased risk of primary hepatocellular carcinoma or liver cirrhosis.

Infection mostly occurs via perinatal or parenteral transmission of infectious virions, for example in the course of blood transfusions or by use of contaminated injection syringes or tips, or by sexual contact. Therefore there is an urgent need for reliable diagnostic means for detection of HBV and for a vaccine protecting people at high risk of exposure, such as spouses of chronic carriers, travellers to areas of high HBV endemicity, newborns of chronic carriers, homosexuals, prostitutes and drug abusers, which should be affordable at low costs. Furthermore in third world countries there exists a need for an inexpensive vaccine for mass immunisation programmes.

In addition to viral particles consisting of the core (HBcAg) and capsid or surface (HBsAg) antigen proteins enclosing the circular, partially double stranded DNA genome the blood of infected individuals may contain substantial quantities of HBsAg particles containing the surface antigen protein and host lipids. These particles have been purified from human serum and formulated as vaccines which have been shown to confer protection against HBV infection (Szmuness et al, 1980).

In this application certain publications are referenced by mention of the first author and the year of publication within parenthesis. Full citation for these references listed according to their alphabetical order may be found at the end of the specification. The disclosures of these publications in their entireties are hereby incorporated by reference into this application in order to more fully describe the state of the art.

The preparation of vaccines from serum derived HBsAg has been hampered by the limited supply of infected blood and by the need to undergo long and rigorous testing to ensure the removal and/or inactivation of potential infectious agents.

Hepatitis B virus (HBV) infection in humans is associated with the occurrence in the serum of various structures carrying the hepatitis B surface antigen (HBsAg) [Tiollais et al, Nature, 17:489 (1985)]. In addition to infectious virions, filamentous and spherical particles of 22 nm in diameter (containing about 100 envelope proteins) are present which are formed by association of host-derived lipids with the three hepatitis surface proteins: the major (S), middle (M) and large (L) proteins.

These proteins share the same sequence of 226 amino acids codons on the HBV genome, known as the S protein coding sequence. The entire amino acid coding sequence which immediately precedes the S protein coding sequence on the HBV genome is referred to herein as the preS coding sequence. The preS coding sequence codes for a 55 amino acid sequence which immediately precedes the S protein, called the preS2 region, and, depending on the virus subtype, either a 108 or 119 amino acid sequence which immediately precedes the preS2 region, called the preS1 region.

The entire preS coding sequence thus codes for 163 (55 preS2+108 preS1) amino acids in ay subtypes and for 174 (55 preS2+119 preS1) amino acids in most ad subtypes. Sequence comparisons between the preS coding sequences in the genomes of ad and ay isolates have shown that the first eleven codons of the preS1 region of ad isolates are not present in ay subtypes. In agreement with the generally adopted nomenclature, throughout this application the codon and amino acid numbering of ad subtypes is followed, meaning that HBV genomes of ad isolates encode a preS region of 174 amino acids numbered 1 to 174 while the 163 amino acids preS region of ay subtypes are numbered 12 to 174.

The major protein (S) is encoded by the 226 amino acid codons S gene and exists in glycosylated and non-glycosylated forms.

The middle protein (M) includes the preS2 region and the S protein (M protein: 55 plus 226 amino acids). The M protein is a glycoprotein present in two forms according to the extent of glycosylation [Stibbe et al, J. Virol., 46:626–628 (1983)]. The 55 amino acids encoded by the preS2 region are hydrophilic and contain an immunodominant epitope located at the surface of the envelope gene (residues 132–137). This epitope is disulfide bond-independent and reported to be more immunogenic than epitopes of the S protein. [Neurath et al, Science, 224:392–394 (1984); Neurath et al., Nature, 315:154–156 (1985)]. The preS2 sequence also contains a receptor for polymerized human serum albumin (pHSA) [Machida et al, Gastroent., 86:910–918 (1984)]. This receptor can also bind monomeric HSA and may mediate attachment of HBV to hepatocytes, which also have a receptor for pHSA. It has been suggested that such binding could lead to tolerance or auto-immune reactions in humans.

The large protein (L) includes the preS1 region, the preS2 region and the S coding sequence (L protein: 108 (or 119) plus 55 plus 226 amino acids). It is present in glycosylated and non-glycosylated forms. The L protein is of variable length according to the subtype, e.g., 389 and 400 amino acids long for the ay and ad subtypes, respectively. The preS1 translation product is also involved in the attachment of HBV to hepatocytes.

Because the promoter for the S and M specific transcripts is embedded within the open reading frame of the L protein, transformation of mammalian cells with DNA encoding the complete open reading frame for the L protein may result in synthesis of all three surface proteins. In mammalian cells, HBsAg particles are secreted [Tiollais et al, cited above]. In mammalian systems expression of L protein causes an inhibition of secretion of HBsAg particles. [See, e.g., Ou et al, *J. Virol.,* 61:782 (1987)]. This phenomenon has been suggested to be related to the presence on the L protein of an N-myristoyl group, causing interference with the budding or secretion process [Persing et al, *Science,* 234:1388–1391 (1986); Persing et al, *J. Virol.,* 61:1672–1677 (1987)].

For ease of reference, the following Table A sets out the DNA coding sequences and amino acid sequences for the preS1, preS2 and S regions of the HBV proteins discussed herein. Amino acid numbers are above the codons in parentheses and are numbered from the first ATG codon present in the open reading frame for the envelope proteins found in HBV adw isolate sequence which was cloned on plasmid pRIT10616. As the first eleven codons of this ad sequence are not present in any of the expression casettes described in the present application these sequences are not given in Table A.

Plasmid pRIT10616, harboured in *E. coli* K12 strain C600, is on deposit at the American Type Culture Collection, Rockville, Md., U.S.A. under accession number ATCC 39131.

TABLE A

PRE-S1 REGION

```
(12)
ATG GGG ACG AAT CTT TCT GTT CCC AAC CCT CTG GGA TTC TTT
Met Gly Thr Asn Leu Ser Val Pro Asn Pro Leu Gly Phe Phe

(26)
CCC GAT CAT CAG TTG GAC CCT GCA TTC GGA GCC AAC TCA AAC
Pro Asp His Gln Leu Asp Pro Ala Phe Gly Ala Asn Ser Asn

(40)
AAT CCA GAT TGG GAC TTC AAC CCC ATC AAG GAC CAC TGG CCA
Asn Pro Asp Trp Asp Phe Asn Pro Ile Lys Asp His Trp Pro

(54)
GCA GCC AAC CAG GTA GGA GTG GGA GCA TTC GGG CCA GGG CTC
Ala Ala Asn Gln Val Gly Val Gly Ala Phe Gly Pro Gly Leu

(68)
ACC CCT CCA CAC GGC GGT ATT TTG GGG TGG AGC CCT CAG GCT
Thr Pro Pro His Gly Gly Ile Leu Gly Trp Ser Pro Gln Ala

(82)
CAG GGC ATA TTG ACC ACA GTG TCA ACA ATT CCT CCT CCT GCC
Gln Gly Ile Leu Thr Thr Val Ser Thr Ile Pro Pro Pro Ala

(96)
TCC ACC AAT CGG CAG TCA GGA AGG CAG CCT ACT CCC ATC TCT
Ser Thr Asn Arg Gln Ser Gly Arg Gln Pro Thr Pro Ile Ser (110)                                   (119)
CCA CCT CTA AGA GAC AGT CAT CCT CAG GCC
Pro Pro Leu Arg Asp Ser His Pro Gln Ala
```

PRE-S2 REGION

```
(120)
ATG CAG TGG AAT TCC ACT GCC TTC CAC CAA GCT CTG CAG GAT
Met Gln Trp Asn Ser Thr Ala Phe His Gln Ala Leu Gln Asp (134)
CCC AGA GTC AGG GGT CTG TAT TTT CCT GCT GGT GGC TCC AGT
Pro Arg Val Arg Gly Leu Tyr Phe Pro Ala Gly Gly Ser Ser (148)
TCA GGA ACA GTA AAC CCT GCT CCG AAT ATT GCC TCT CAC ATA
Ser Gly Thr Val Asn Pro Ala Pro Asn Ile Ala Ser His Ile (162)                                               (174)
TCG TCA AGC TCC GCG AGG ACT GGG GAC CCT GTG ACG AAC
Ser Ser Ser Ser Ala Arg Thr Gly Asp Pro Val Thr Asn
```

S PROTEIN

```
(175)
ATG GAG AAC ATC ACA TCA GGA TTC CTA GGA CCC CTG CTC GTG
Met Glu Asn Ile Thr Ser Gly Phe Leu Gly Pro Leu Leu Val

TTA CAG GCG GGG TTT TTC TTG TTG ACA AGA ATC CTC ACA ATA
Leu Gln Ala Gly Phe Phe Leu Leu Thr Arg Ile Leu Thr Ile

CCG CAG AGT CTA GAC TCG TGG TGG ACT TCT CTC AAT TTT CTA
```

TABLE A-continued

```
Pro Gln Ser Leu Asp Ser Trp Trp Thr Ser Leu Asn Phe Leu

GGG GGA TCA CCC GTG TGT CTT GGC CAA AAT TCG CAG TCC CCA
Gly Gly Ser Pro Val Cys Leu Gly Gln Asn Ser Gln Ser Pro

ACC TCC AAT CAC TCA CCA ACC TCC TGT CCT CCA ATT TGT CCT
Thr Ser Asn His Ser Pro Thr Ser Cys Pro Pro Ile Cys Pro

GGT TAT CGC TGG ATG TGT CTG CGG CGT TTT ATC ATA TTC CTC
Gly Tyr Arg Trp Met Cys Leu Arg Arg Phe Ile Ile Phe Leu

TTC ATC CTG CTG CTA TGC CTC ATC TTC TTA TTG GTT CTT CTG
Phe Ile Leu Leu Leu Cys Leu Ile Phe Leu Leu Val Leu Leu

GAT TAT CAA GGT ATG TTG CCC GTT TGT CCT CTA ATT CCA GGA
Asp Tyr Gln Gly Met Leu Pro Val Cys Pro Leu Ile Pro Gly

TCA ACA ACA ACC AAT ACG GGA CCA TGC AAA ACC TGC ACG ACT
Ser Thr Thr Thr Asn Thr Gly Pro Cys Lys Thr Cys Thr Thr

CCT GCT CAA GGC AAC TCT ATG TTT CCC TCA TGT TGC TGT ACA
Pro Ala Gln Gly Asn Ser Met Phe Pro Ser Cys Cys Cys Thr

AAA CCT ACG GAT GGA AAT TGC ACC TGT ATT CCC ATC CCA TCG
Lys Pro Thr Asp Gly Asn Cys Thr Cys Ile Pro Ile Pro Ser

TCC TGG GCT TTC GCA AAA TAC CTA TGG GAG TGG GCC TCA GTC
Ser Trp Ala Phe Ala Lys Tyr Leu Trp Glu Trp Ala Ser Val

CGT TTC TCT TGG CTC AGT TTA CTA GTG CCA TTT GTT CAG TGG
Arg Phe Ser Trp Leu Ser Leu Leu Val Pro Phe Val Gln Trp

TTC GTA GGG CTT TCC CCC ACT GTT TGG CTT TCA GCT ATA TGG
Phe Val Gly Leu Ser Pro Thr Val Trp Leu Ser Ala Ile Trp

ATG ATG TGG TAT TGG GGG CCA AGT CTG TAC AGC ATC GTG AGT
Met Met Trp Tyr Trp Gly Pro Ser Leu Tyr Ser Ile Val Ser

CCC TTT ATA CCG CTG TTA CCA ATT TTC TTT TGT CTC TGG GTA
Pro Phe Ile Pro Leu Leu Pro Ile Phe Phe Cys Leu Trp Val (400)
TAC ATT TAA
Tyr Ile Stop
```

Viral transcription initation signals located 5' to the translation initiation codons control the expression of each of the preS1, preS2 and S proteins in vivo. Upon translation in the mammalian cell, the proteins may be glycosylated, resulting in a set of surface antigens as demonstrated in the following table.

| Protein | Length (amino acids) | Designation | Glycosylation of S-protein Sequences | Glycosylation of preS2-specific domains |
|---|---|---|---|---|
| P24 | 226 | S-protein | − | − |
| GP27 | 226 | S-protein | + | − |
| GP33 | 281 | preS2-protein | − | + |
| GP36 | 281 | preS2-protein | + | + |
| P39* | 389 | preS1-protein | − | − |
| GP42* | 389 | preS1-protein | + | − |

*: Subtype ayw; the preS1-proteins derived from adw-subtype are about 1.0 to 1.5 kDa larger, which is in agreement with an additional 11 amino acids at the N-terminal end (Heermann et al., 1984).

Since the DNA sequence of the surface antigen coding region became known, several attempts have been made to produce S protein by virtue of recombinant DNA technology. Burrell et al. (1979) and Murray et al. (1980) as well as several other researchers reported the expression of HBsAg in E. coli. Valenzuela et al. (1982) reported the expression of HBsAg in yeast. Following disruption of yeast cells transformed with a vector containing the S protein coding sequence under control of the yeast alcohol dehydrogenase I promoter, spherical particles containing HBsAg could be observed which are similar to those found in sera of individuals infected with HBV. In European Patent Application 0 226 846 (Tschopp et al.) the production of HBV S-protein in the yeast Pichia is disclosed. Protein synthesis is under the control of a regulatory region responsive to methanol.

However, although vaccines containing exclusively S-antigen particles are generally highly protective (Szmuness et al., 1980) some hosts respond poorly to such preparations. To overcome this unpredictable failure of the vaccination, systems for expression of preS2-protein and preS1-protein have been developed. PreS2 is known to be even more immunogenic than S-protein. For example, upon immunisation of mice with subviral particles bearing preS2- and S-specific epitopes, the antibody response to preS2 exceeds the anti-S-response (Milich et al., 1985). Furthermore it has been observed that immunisation with preS2 containing particles may also induce an anti-S-response. The role of preS1- and preS2-proteins in immunisation and the specificity of the T- and B-cell recognition of HBV surface antigen proteins has recently been reviewed (Milich, 1988, with references therein). Valenzuela et al. (1985) disclose the expression of the entire preS2- protein coding sequence in yeast transformed with a plasmid containing the corresponding viral sequences. It has to be noted, that in yeast transcription, initiation has to be directed by yeast promoters preceding the respective coding region, since the viral transcription initiation signals within the HBV-ORF are not recognised by the yeast transcription system.

Itoh et al. (1986) and others also disclose expression of the preS2-protein in yeast and assembly into particles. Dehoux et al. (1986) disclose expression of a 39 kD preS1-protein in yeast and state that this is assembled into a particle form. A report by Imamura et al. (1987) discloses expression in S. cerevisiae of both the preS2-protein and the preS1-protein. These authors state that the large protein was found as a relatively stable, non-glycosylated product of 42 kD molecular weight which was not readily assembled into particles.

Glycosylation of the surface proteins produced in the yeast S. cerevisiae differs from glycosylation observed in naturally occuring particles isolated from individuals infected with HBV. The S-protein is not glycosylated, whereas preS2-protein and preS1-protein are produced in N-linked glycosylated and non-glycosylated forms. N-linked chains of the high mannose type were identified, as well as O-linked oligosaccharide chain(s) (Itoh et al., 1986; Langley et al., 1988).

Expression of HBV surface antigen in mammalian cells has also been performed. Michel et al. (1984) disclosed the synthesis of HBsAg in Chinese Hamster ovary (CHO) cells transfected with a plasmid carrying the preS2-protein coding sequence. Persing et al. (1985) disclosed the expression of three HBsAg related polypeptides of 24,000, 27,000 and 35,000 daltons in mouse L cells transformed with a preS2-protein coding sequence. The three polypeptides obtained may be organised into complex immuno reactive HBsAg particles of about 22 nm diameter.

McLachlan et al. (WO88/06185) reported on the expression of various HBV related proteins in vertebrate cells. However, the expression of preS-antigen in mammalian cells is generally hampered by the fact that due to relative overproduction of preS1-protein relative to S-protein secretion of HBsAg particles is inhibited (Ou et al., 1987). Moreover the ratio of the different S related proteins cannot be controlled. Finally culturing of animal cells is an expensive approach which results in high costs for the product obtained.

Although vaccines presently described and in use have great efficacy, a certain percentage of persons receiving such vaccines, particularly immunocompromised persons, e.g., hemodialysis patients, are non- or slow responders [See, e.g., Hadler et al, *New Engl. J. Med.,* 315:209–215 (1986); and Bruguera et al, *Post Grad. Med. J.,* 63:155–158 (1987)].

There thus remains a need in the art for methods and compositions useful in preparing additional effective vaccines to HBV.

According to a first aspect of the present invention there is provided a microorganism selected from the group of methylotrophic yeast genera, carrying A) more than one copy of an expression cassette (ec1) coding for a first polypeptide and/or one or more than one copy of an expression cassette (ec2) coding for a second polypeptide, optionally in addition one or more than one expression cassette (ec3) coding for a third polypeptide, or B) one copy of an expression cassette (ec1) coding for a first polypeptide and one or more than one copy of an expression cassette (ec2) coding for a second polypeptide, optionally in addition one or more than one expression cassette (ec3) coding for a third polypeptide, wherein the expression cassettes comprise:

a) a regulon R which is responsive to methanol and/or depletion of catabolite repressing carbon sources;

b) an open reading frame coding for all or part (or parts) of a protein having the biological activity of one of the hepatitis B surface antigens;

c) optionally a DNA sequence serving as a transcription terminator T;

wherein R exerts control on the transcription of the open reading frame and T directs polyadenylation and/or termination of transcription of a produced mRNA.

The advantage of the above aspect of the invention is that a means is provided for obtaining composite particles containing various ratios of pre S- and S-protein thereby allowing the large scale production of these composite particles at low costs.

The present invention also provides a composite particle containing at least two polypeptides corresponding to all or part of a protein having the biological activity of a hepatitis B surface antigen, wherein the particle presents at least two antigenic determinants provided by the S-protein, preS2-protein or preS1-protein, said particle optionally further comprising host specific lipids.

The following terms used throughout the specification are defined as follows:

An "expression cassette" is defined as any discrete region of DNA which functions in a host cell as a complete gene expression unit.

A "complete gene expression unit" is a structural gene and the promoter and regulatory regions required for its transcription and translation.

A "functional DNA coding region" means a DNA coding sequence which, when fused in phase to the S protein coding sequence, does not interfere with the assembly of an HBsAg mixed particle.

A "functional derivative" means a coding sequence having amino acid alterations which do not interfere with particle formation and which retain immunogenicity or other functionality. Such functional derivatives can be prepared by conventional site specific mutagenesis or by other standard techniques.

A "vector" is defined as DNA which can carry and maintain the DNA fragment of the invention, including, for example, phages and plasmids. These terms are understood by those of skill in the art of genetic engineering.

The invention, which comprises further subjects, is now described in a tore detailed manner by the following description, examples and figures.

BRIEF DESCRIPTION OF THE FIGURES

FIG. 5: Maps of plasmids pBC, pMS-2, pFS-9. The latter two plasmids are derived from pBC containing the

*Hansenula polymorpha* URA3 gene by insertion of expression cassettes containing the MOX promoter (pMS-2) or the FMD promoter (pFS-9) into the URA3 gene coding sequence.

Figure 6:
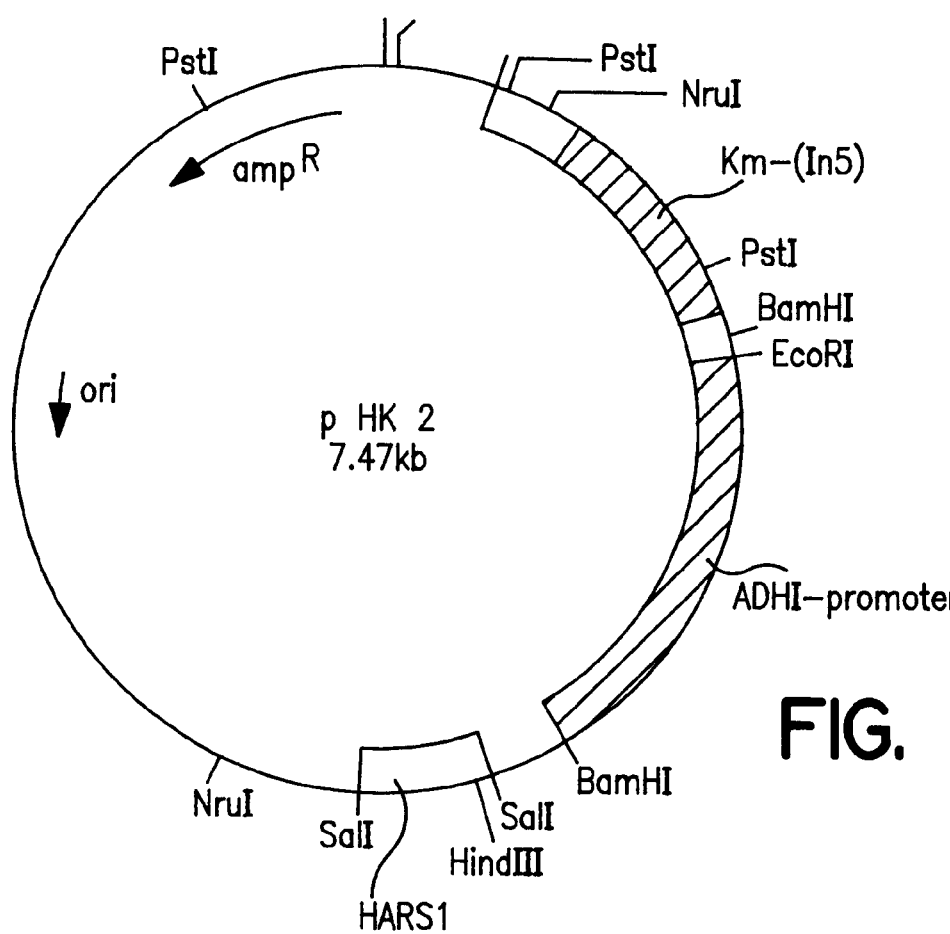

FIG. 6: Map of plasmid pHK2. This plasmid contains a kanamycin gene (derived from Tn5) under control of the ADH1-promoter of *Saccharomyces cerevisiae*. In addition plasmid pHK2 comprises the HARS1 sequence.

Figure 7:
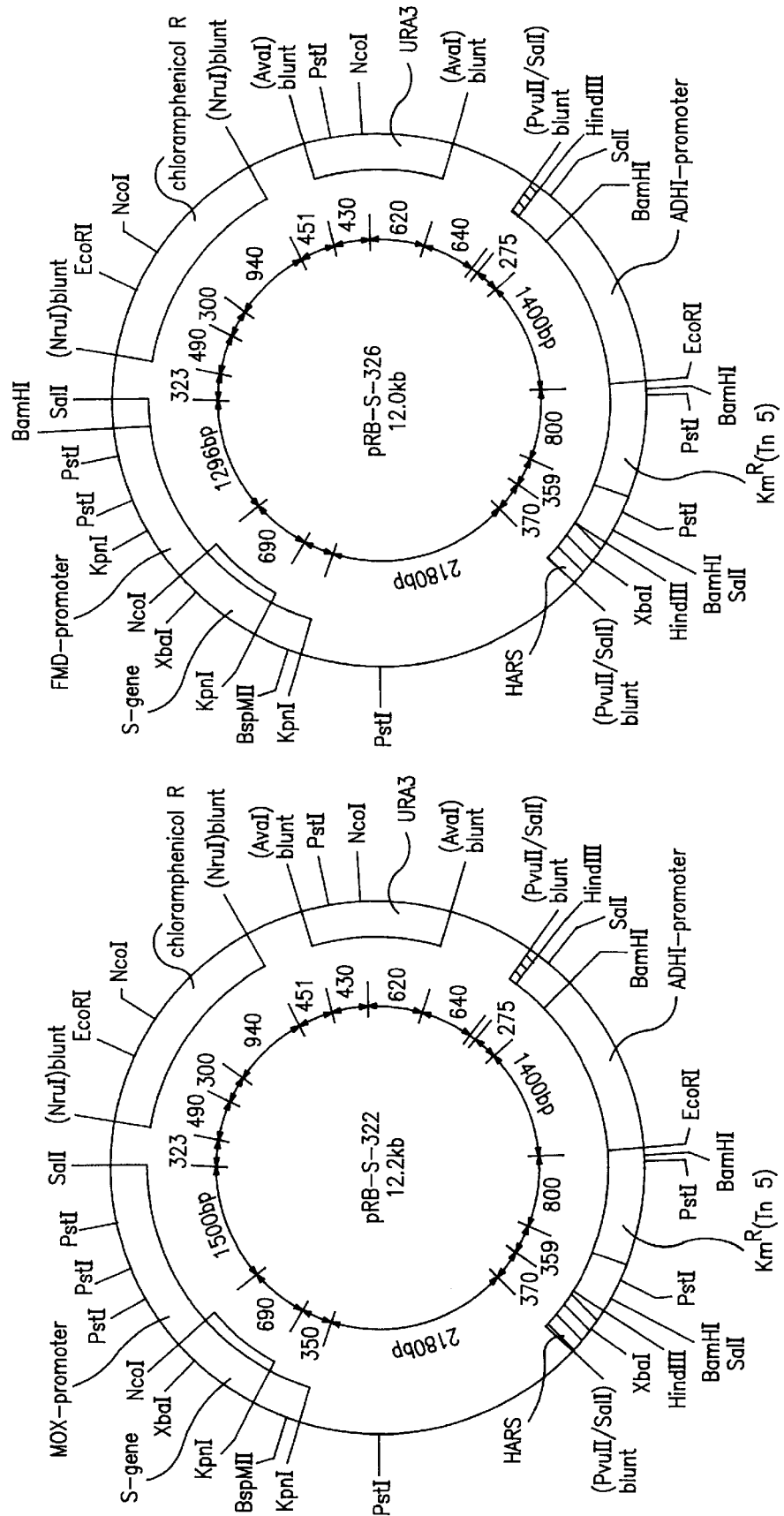

FIG. 7: Maps of plasmids pRB-S-322 and pRB-S-326. The functional unit consisting of the kanamycin resistance gene and ADH1-promoter as present on plasmid pHK was inserted into the HARS regions of plasmid pRB-S-269 and pRB-S-271.

Figure 8:
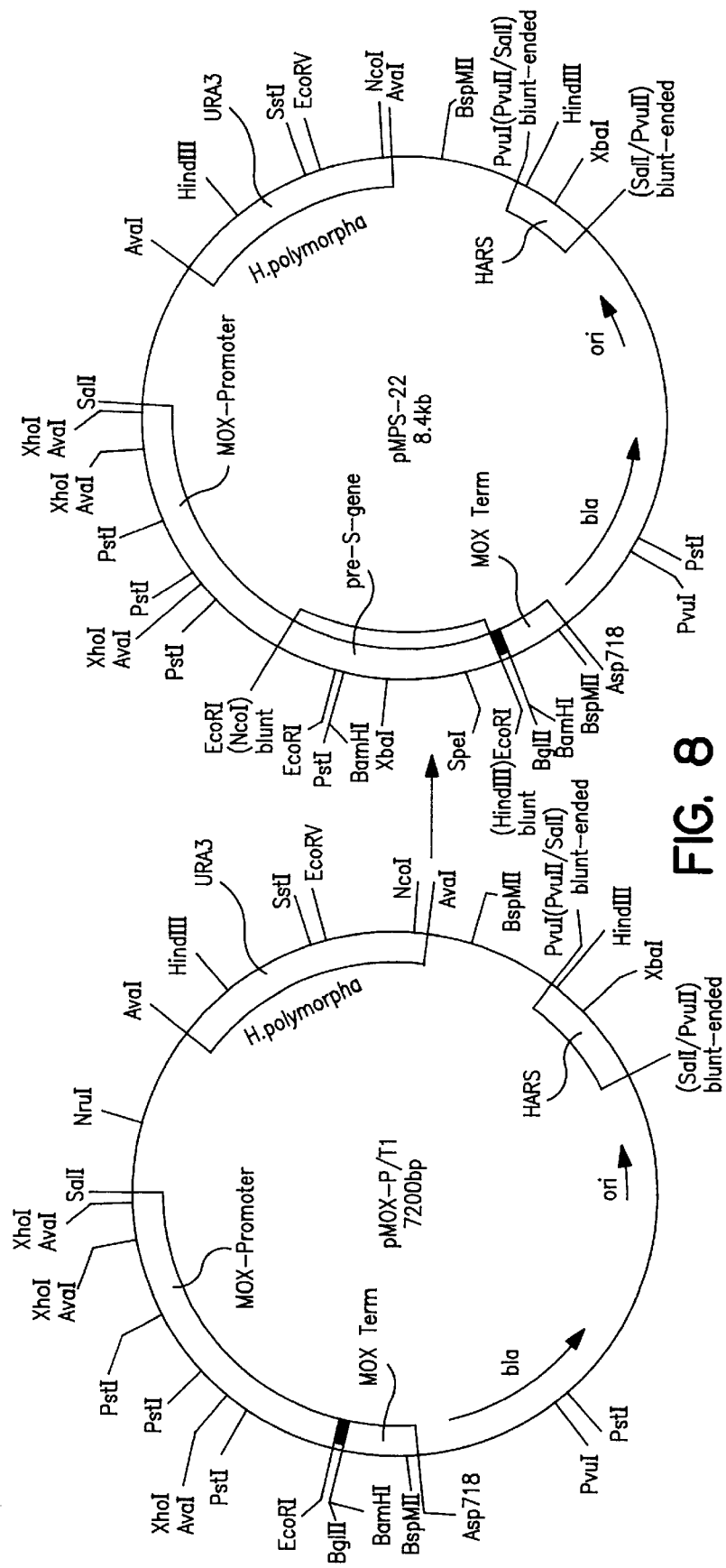

FIG. 8: Construction of pMPS-22 from pMOX-P/T1. The preS gene of Hepatitis B virus was inserted into the EcoRI site of plasmid pMOX-P/T1. In the resulting plasmid pMPS-22 the preS gene is regulated by the MOX promoter.

Figure 9:
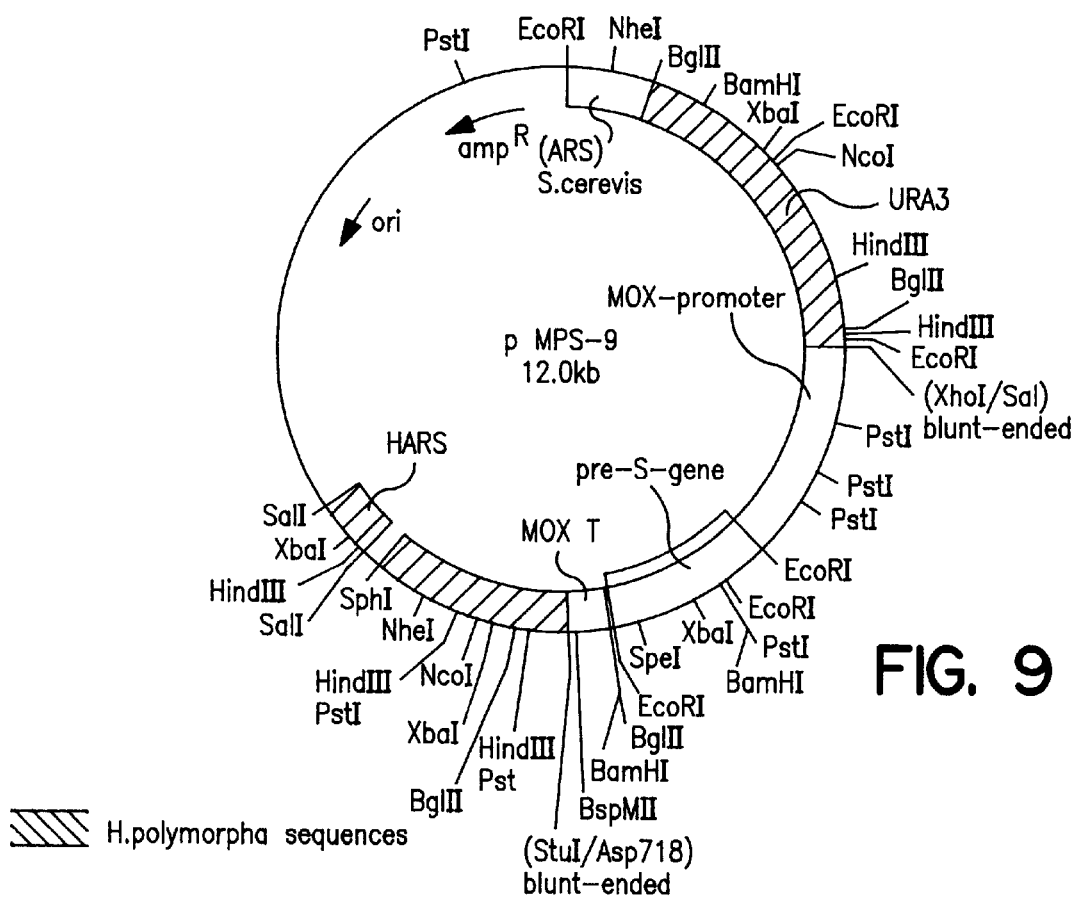

FIG. 9: Map of plasmid pMPS-9. For the construction of this plasmid: the preS expression cassette of pMPS-22 was inserted between the XhoI and StuI site of the Hansenula fragment of original plasmid pBC.

Figure 10:
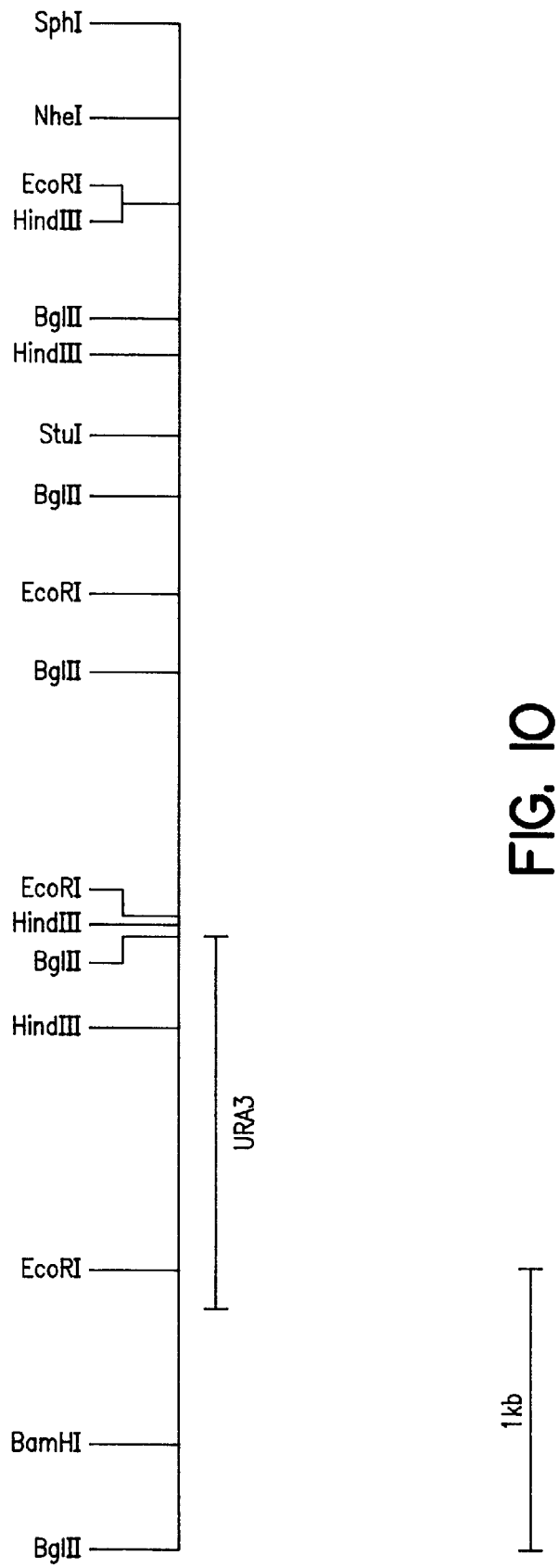

FIG. 10: Map of the *Hansenula polymorpha* URA3 gene and adjacent DNA-regions.

Figure 11:
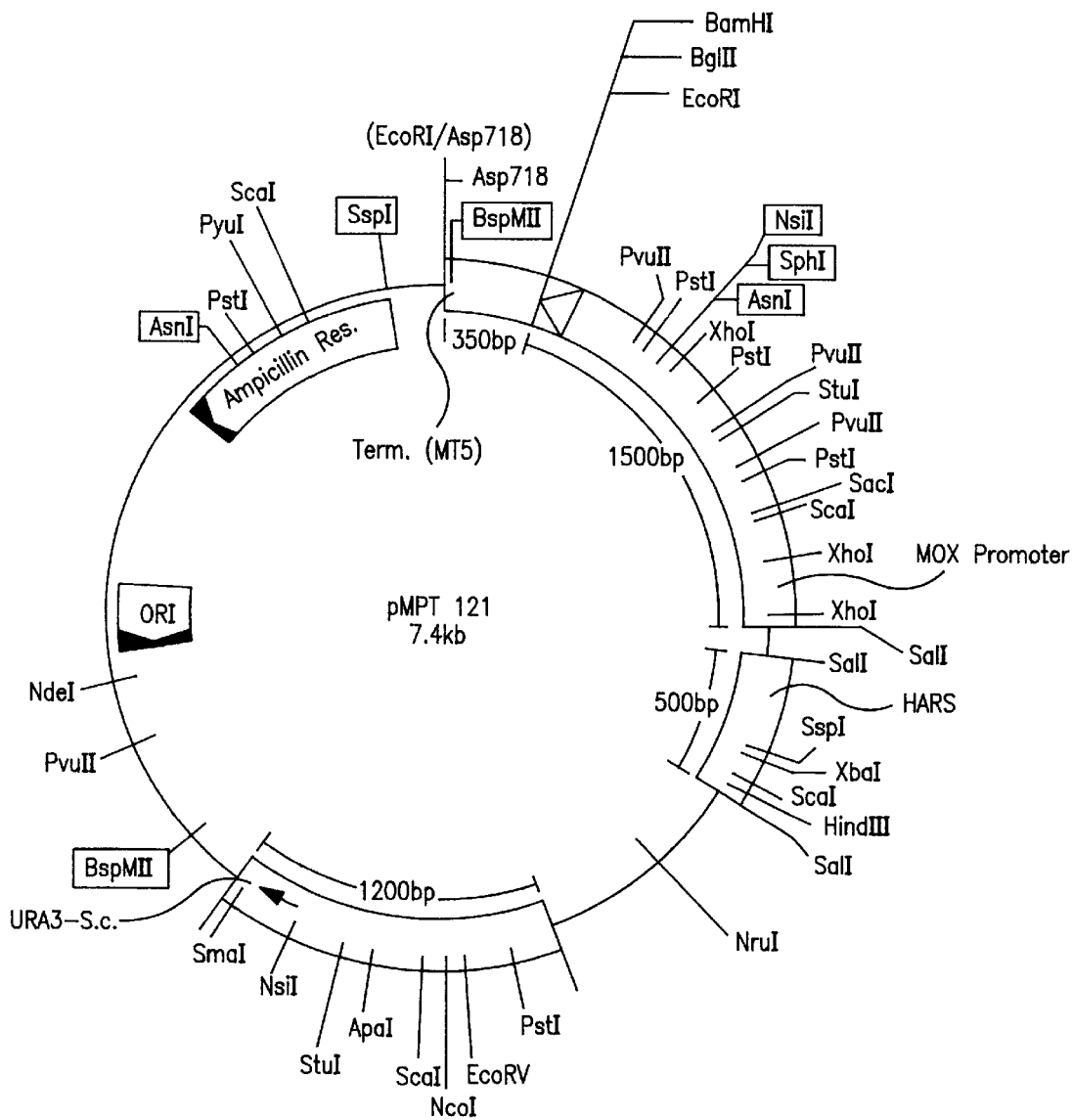

FIG. 11: A diagram illustrating the structure of plasmid pMPT121 in which foreign gene sequences can be inserted under the control of the MOX promoter.

Figure 12:
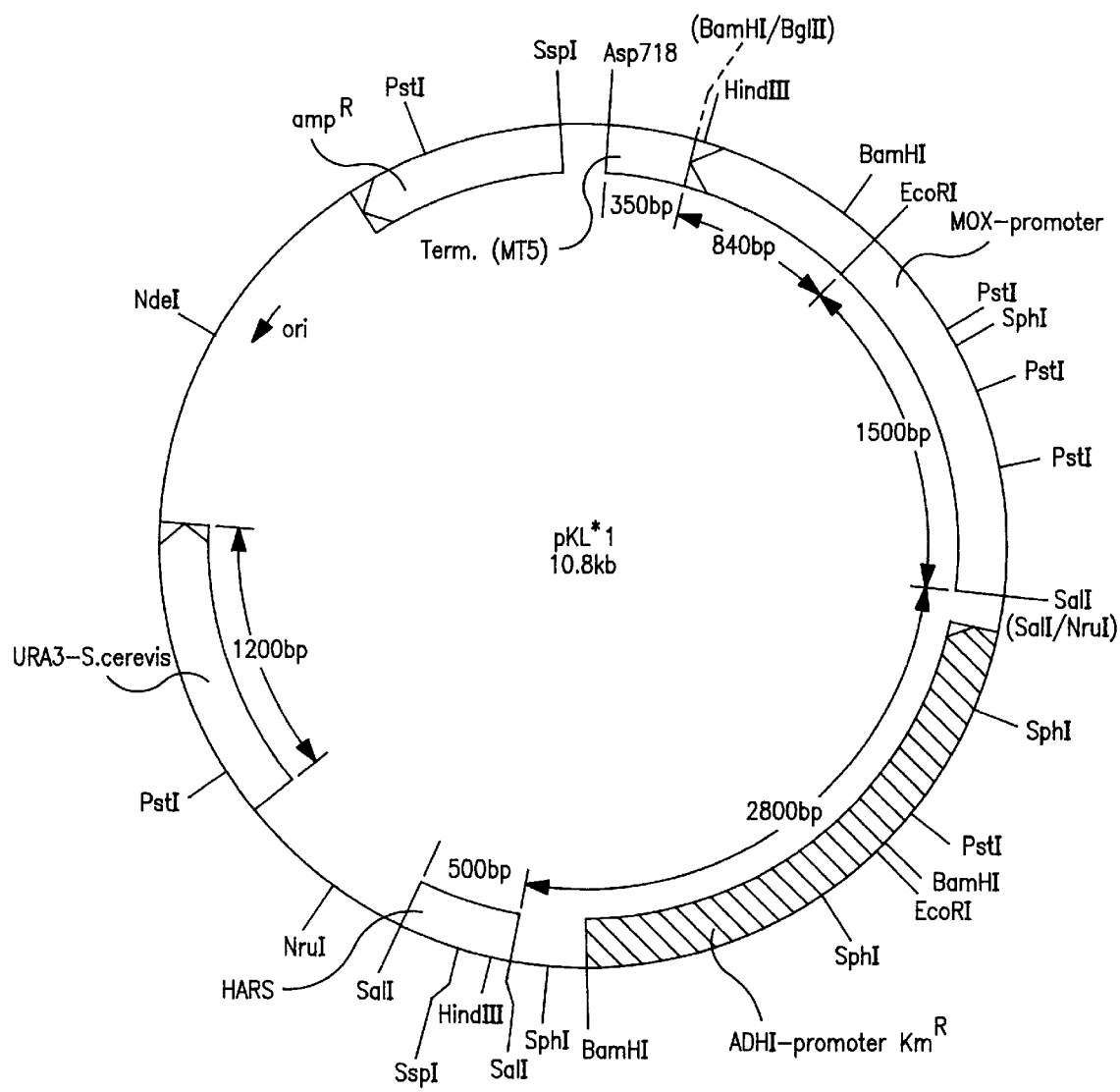

FIG. 12: A diagram illustrating the structure of plasmid pKL*1 containing an expression cassette for L* protein under control of the MOX promoter.

Figure 13:
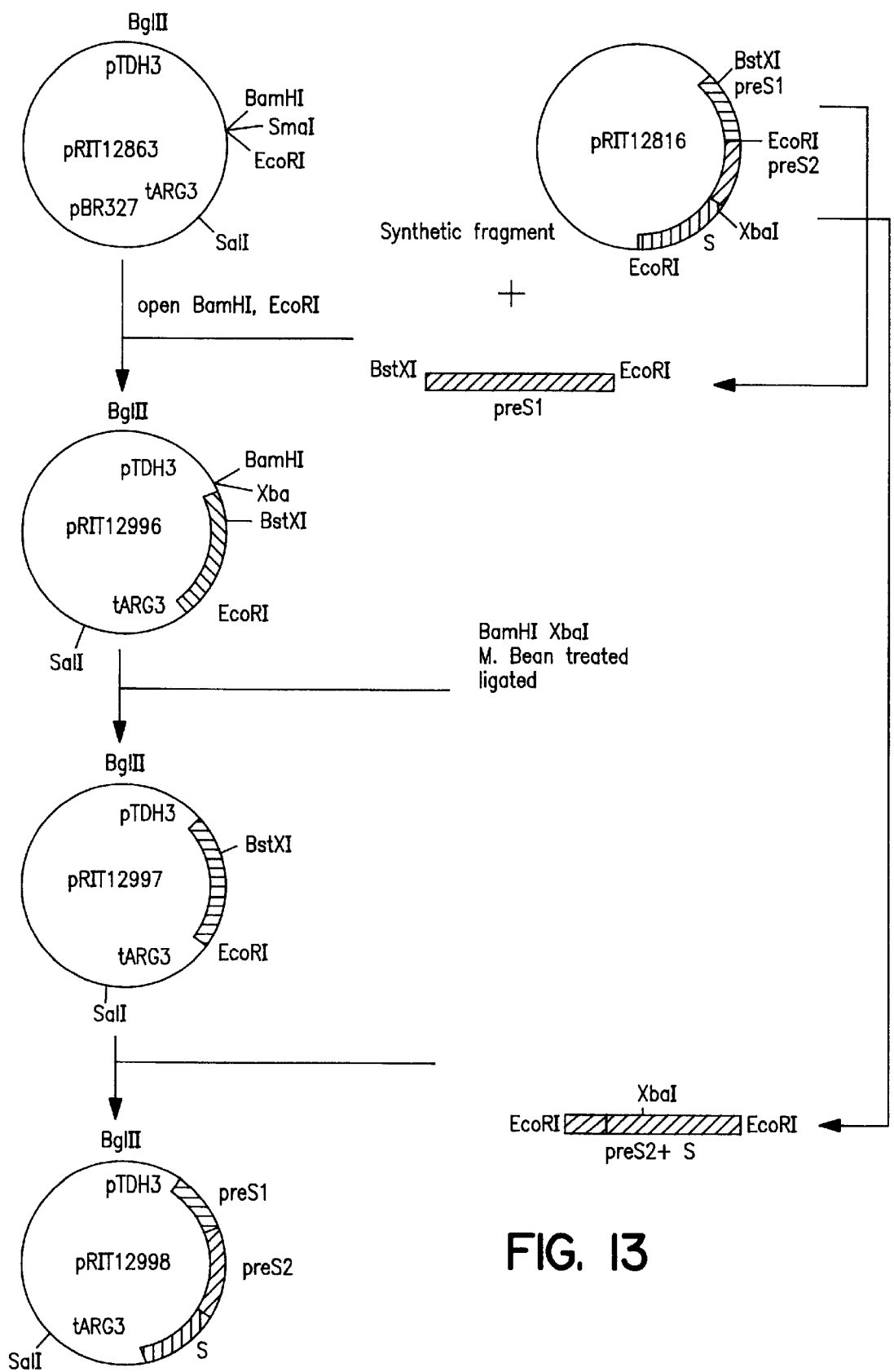

FIG. 13: A schematic diagram showing the steps for constructing an *E. coli* plasmid harbouring a Gly13 deleted L protein-expression cassette, pRIT12998.

Figure 14:
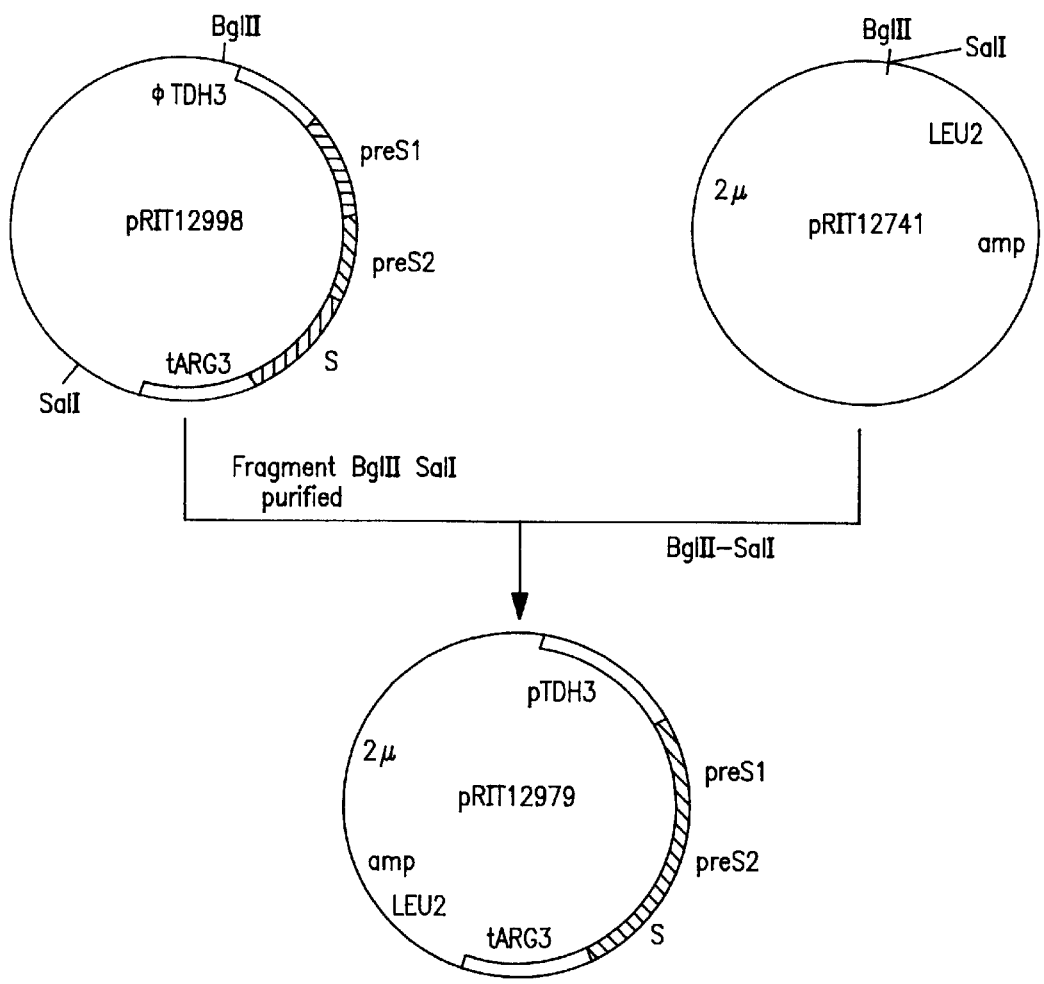

FIG. 14: A schematic diagram illustrating the procedure for obtaining a yeast plasmid pRIT12979 capable of expressing a Gly13 deleted L protein.

Figure 15:
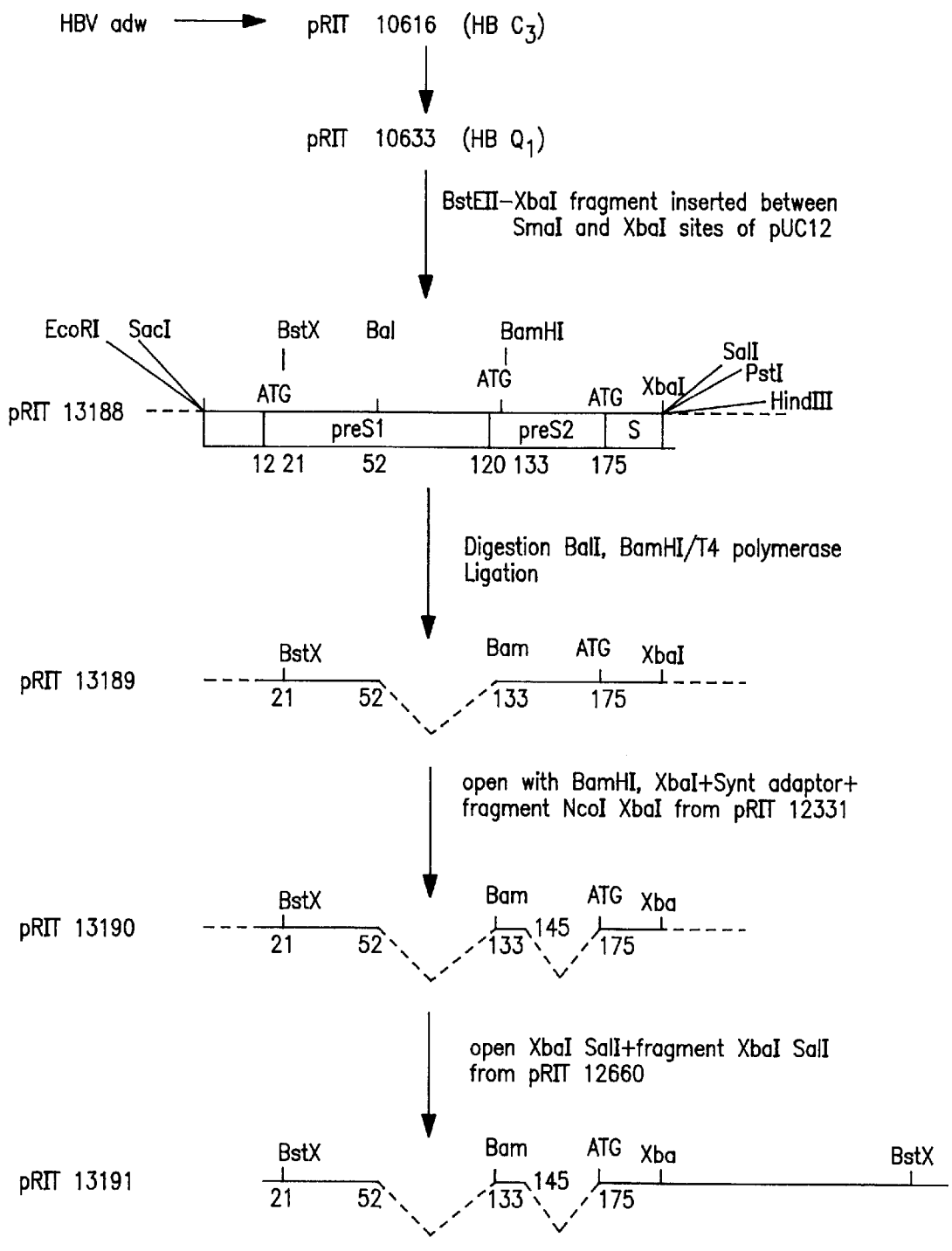

FIG. 15: A schematic diagram illustrating the construction of the plasmid pRIT13191 containing the coding sequence for an L protein deleted for amino acids 53–132 and 146–174.

Figure 16:
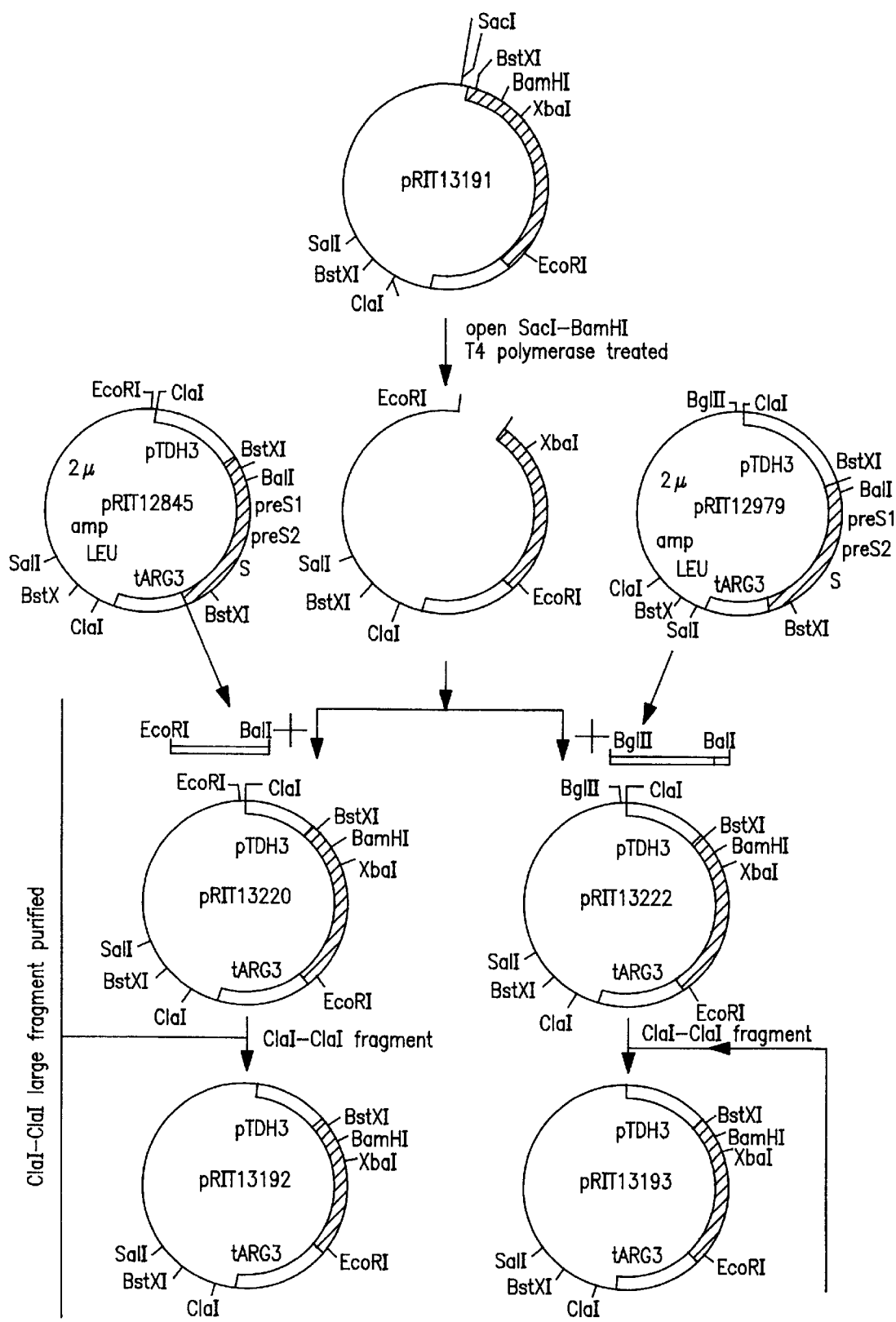

FIG. 16 A schematic diagram illustrating the construction of yeast expression plasmids pRIT13192 and pRIT13193 containing the expression cassettes for the L* and ΔGly L* proteins respectively.

The microorganism according to the first aspect of the invention may be any member of a methylotrophic yeast genus, which has been manipulated to carry more than one copy of an expression cassette ec1 and optionally one or more than one expression cassette ec2 and/or optionally one or more than one expression cassette ec3 or at least one expression cassette of two or more different types. The expression cassettes need only differ in the nature of the encoded protein to be expressed and in general comprise the following components:

a) A regulon R which is responsive to methanol and/or depletion of catabolite repressing carbon sources. The term "regulon" as used throughout the application comprises any cis-acting DNA involved in the regulation of expression of a given structural gene. The term thus embraces sequences preceding a given coding sequence, for example, a promoter and sequences which are recognised by transcription factors or other proteins involved in transcription regulation. The meaning of the term "regulon" is thus not limited to sequences corresponding to known promoters. Also included are DNA sequences exhibiting the same responsiveness to methanol as known regulons of methanol inducible genes, i.e. all functionally equivalent sequences.

Recently several regulons exhibiting the above outlined properties became known. For example Ledeboer et al. (1985) disclose the regulatory DNA sequence preceding the methanol oxidase (MOX) structural gene of *Hansenula polymorpha*. In EP 85 201 235.0 to Unilever NV, a system for the expression of proteins is disclosed, which involves the use of the promoters regulating the expression of methanol oxidase and DHAS in vivo. In EP 87 110 417 to Rhein Biotech GmbH, a system suitable for expression of foreign proteins under control of the formate dehydrogenase promoter (FMD) is proposed. Ellis et al. (1985) disclose the isolation of methanol regulatable genes from *Pichia pastoris*. These and other promoters obtained or obtainable from genes of methylotrophic yeast, which are potentially involved in methanol utilisation, all have in common that they respond to either addition of methanol and/or depletion of a carbon source with enhanced synthesis of the respective gene regulated by them. Also included are all DNA sequences which exhibit the same responsiveness.

b) An open reading frame (ORF) coding for part(s) or all of the protein having the biological activity of one of the hepatitis B surface antigens. As already mentioned, hepatitis B surface antigens of given subtype comprise a set of about six different proteins, differing in length and glycosylation pattern. These proteins exhibit different antigenic determinants and also seem to have different functions for the viable virus. For eliciting a preS immune response it is not necessarily required to provide the respective complete preS-sequence, but it may be sufficient to include just those codons encoding the relevant epitope into the open reading frame. Furthermore a protein having the biological activity of one of the hepatitis B surface antigens also includes proteins having undergone exchanges of amino acids which do not interfere with their biological activity.

c) Optionally a DNA sequence serving as a terminator T. As the terminator any sequence may be used, which efficiently terminates transcription in the respective host organism. Terminators may be for example sequences prone to give formation of hairpin structures and/or polyadenylation sites in transcribed RNA. In a preferred embodiment the terminator is derived from a methanol responsive gene of the same organism and/or from the same gene as the regulon was obtained.

The three components are arranged in operable linkage in order to enable the regulon to regulate transcription and the terminator to terminate transcription of the open reading frame between them.

The microorganism according to the present invention has the invaluable advantage, that because of the presence of more than one copy of an expression cassette coding for a first polypeptide and/or one or more than one copy of each of the different additional expression cassettes, transcription and translation of the encoded protein(s) may occur in highly enhanced amounts. The microorganism according to the present invention provides the possibility to obtain any desired ratio of a first to a second polypeptide within the cell. Thus, upon assembly of protein to form particles composite particles of any composition may be obtained. Furthermore owing to the production of high amounts of different proteins in close proximity these proteins are more liable to form particles comprising more than one polypeptide species than particles known in the art.

The microorganism according to the present invention preferably expresses all or part of the S-protein from a first expression cassette (ec1) since this constitutes the structural scaffold of any particle which may be formed. In one embodiment the microorganism further contains a second expression cassette (ec2) which expresses a polypeptide representing all or part of the preS1-protein, for example the preS1 specific domains localised at the N-terminal end of this protein or all or part of the preS2-protein. In a further embodiment the microorganism may contain three different types of expression cassette to enable simultaneous expression of three polypeptides comprising all or part of the S-protein, all or part of the preS1 protein and all or part of the preS2-protein.

Furthermore, the use of regulons derived from methylotropic yeast enables the repression, derepression or induction of a cell culture by addition or depletion of a carbon source or by addition of methanol which is cheaply available.

The group of methylotrophic yeasts comprises members of the following genera: Candida, Kloeckera, Saccharomyces, Rhodotorula, Torulopsis and Pichia, preferably Hansenula. In the most preferred embodiment a microorganism according to the present invention is derived from *Candida boidinii, Pichia pastoris* or *Hansenula polymorpha*. Yeasts from these genera are well known to persons skilled in the art and their general culturing and growth conditions are established.

A useful strain of the preferred methylotrophic yeast Hansenula may be any strain of the species *Hansenula polymorpha*. In the most preferred embodiment the strain to be used has the identifying characteristics of *Hansenula polymorpha* RB 10(DSM 5215). RB 10 is a ura3 mutant of *Hansenula polymorpha* ATCC 34438.

In a preferred embodiment the microorganism according to the present invention is capable of efficient utilisation of glycerol as a carbon source. Glycerol is a non-catabolite repressing carbon source which is converted into energy with different efficiency by known methylotrophic yeasts. Yeast species of the genus Hansenula are able to metabolise glycerol with high efficiency, whereas *S. cerevisiae* grows poorly on this carbon source. In addition, growth of *Hansenula polymorpha* on glycerol results in very little ethanol by-production which otherwise causes problems during large-scale fermentation.

The regulons used for the expression cassettes of the present invention are preferably derived from yeast of the well known genera mentioned above. Regulons which have been characterised in detail are preferred, such as the regulating region from various methanol responsive genes of *Hansenula polymorpha*, for example the methanol oxidase gene, the FMD gene, DAS gene or catalase gene. The regulating regions of most of these genes are already sequenced and the sequences published (e.g. Janowicz et al., 1985; Ledeboer et al., 1985, EP 87 110 417). The technical proceedure of isolating these regulons from appropriate microorganism is facilitated by the knowledge of the respective DNA sequences and corresponding restriction patterns.

As a terminator any sequence may be included which efficiently serves to terminate the nascent mRNA regardless of whether it is derived from a eukaryotic or prokaryotic gene. Preferred terminators are derived from yeast genes. Use of termination sequences obtained from the methanol responsive genes cited above is most preferred.

It is another advantage of the microorganism according to the present invention that a surprisingly high number of expression cassettes can be introduced into the respective host cell and be stably maintained. In general, there are two possibilities to achieve stable maintenance of specific genetic information:

The information is either encoded chromosomally or it is localised on an autonomously replicating vector, which may be a plasmid, a cosmid, a virus or the like. Normally higher gene dosages are provided by transformation of the desired host organism using high copy number autonomously replicating plasmids or lysogenic viruses. These plasmids or viruses are well known in the art and usually contain a replicon and a selective marker gene enabling replication and stable maintenance of the vector. However, viruses are often subject to conversion to lytic cycles and plasmids are prone to being lost under certain conditions and furthermore often require continuous selection pressure. Moreover even with high copy number plasmids a copy number of not more than about 50 to 75 can generally be obtained in yeast. On the other hand, introduction of desired genetic information, e.g. an expression cassette, into the host genome normally requires a certain degree of homology between at least part of the DNA sequence to be inserted, preferably the termini of said molecule, and the site of insertion. Thus the number of potential integration sites for homologous recombination of a given molecule is limited, in most cases to just one. This number is slightly more elevated for homologous recombination with genes present in multiple copies or with transposon-like structures such as Ty (Jacobs et al., 1988). In order to promote the integrative recombination event, it is preferable to use vectors lacking a replicon but carrying a selective marker gene, which confers a detectable phenotypic trait to the transformed cell and allows identification under selective conditions.

Random recombination is normally a rarely observed event. However according to the present invention, it is possible to introduce numerous copies of any given DNA sequence into one or more chromosomes of the genome, by insertion due to random recombination. To obtain transformants carrying as many as some hundred copies of the DNA sequence desired, it is preferable to use autonomously replicating plasmids for transformation, which by the simultaneous events of integration of some copies and replication of others can provide a large pool of integratable copies, which are inserted during subsequent cell cycles. Surprisingly it was possible to obtain methylotrophic yeast strains carrying many expression cassettes.

Preferred yeast strains, such as yeast strains of the genus Hansenula, contain about 2–500, preferably 15 to 200, especially 20 to 150 copies of a desired DNA sequence. Once the desired number of integrated expression cassettes is obtained further integration processes can be prevented by cycles of growth on non-selective medium to segregate out the remaining plasmid copies.

A special feature of microorganisms according to the present invention is the phenomenon of multimeric integration. Upon transformation with a vector capable of autonomous replication *Hansenula polymorpha* was found to integrate several repeats of the plasmid used for transformation. Repetitions of up to about 100 copies of the introduced plasmid were observed. This allows the presence and integration of a high number of copies of foreign DNA sequences without jeopardising the cell's viability by insertion into essential genes. Surprisingly integrants containing multimeric DNA were shown to be stable.

For the purpose of designing vaccines containing composite particles a constant ratio of the different polypeptides of said particles is desirable. In order to meet this need the present invention provides microorganisms having a selected ratio of different expression cassettes. For instance, a microorganism according to the present invention may carry between 1 to 100 copies of an expression cassette (ec1)

encoding all or part of a protein having the biological activity of S-protein and 1 copy or several copies of an expression cassette (ec2) encoding a protein having the biological activity of preS2- or preS1-protein.

Preferred microorganisms carry a ratio of between 2 copies of ec1 to one copy of ec2 to 30 copies of ec1 to one copy of ec2 more especially in the ratio of 5 to 10 copies of ec1 to one copy of ec2 or 6–8 copies of ec1 to one copy of ec2. A third expression cassette can be introduced in the same ratio as ec2 or 6–8 copies of ec1 to one copy of ec3.

In addition to the possibility of preparing strains containing integrated copies of the expression cassette, it is also possible to use microorganisms containing autonomously replicating vectors comprising autonomously replicating sequences (ARS) and the desired expression cassette. Presence and maintenance of vectors containing ARS are well known in the art.

Subjects of the present invention are also DNA molecules containing an expression cassette (ec1) coding for a first polypeptide and an expression cassette (ec2) coding for a second polypeptide and/or an expression cassette (ec3) coding for a third polypeptide, wherein the expression cassettes comprise:

a) a regulon R which is responsive to methanol and/or depletion of catabolite-repressing carbon sources;

b) an open reading frame coding for part (or parts) or all of a protein having the biological activity of one of the hepatitis B surface antigens;

c) optionally a DNA sequence serving as a terminator T; wherein R exerts control on the transcription of the open reading frame and T directs polyadenylation and/or termination of transcription of the mRNA produced.

For the properties of the regulon, the open reading frame and the terminator referal is made to the above provided information. Also for these molecules it is preferable to derive both regulon and terminator from a methylotrophic yeast selected from the genera Candida, Kloeckera, Saccharomyces, Rhodotorula, Torulopsis, Pichia and Hansenula. In the most preferred embodiment the regulon and the terminator are derived from a gene involved in methanol utilisation, for example the MOX-gene, the FMD gene, the DAS gene or the catalase gene. *Hansenula polymorpha* is a preferred microorganism as a source for these genes. For the identity of the polypeptides encoded by ec1, ec2 and ec3, referral is made to the explanation given above.

The DNA molecule according to the present invention may be composed of fragments obtained from the respective natural sources. The DNA coding for any of the hepatitis B surface antigens can be isolated from DNA of intact viruses, also called Dane particles. Isolation, cloning and sequencing of HBV virion DNA are disclosed in Charnay et al. (1979), Galibert et al. (1979), Sninsky et al. (1979) Valenzuela et al. (1979).

The choice of restriction enzymes for cloning and DNA manipulation depends on the kind of subtype of hepatitis virus used. The subtypes differ not only by length, but also with respect to their individual restriction patterns which are subject to normal mutation events. It is possible for any person skilled in the art to identify the restriction fragment carrying the desired coding region, for example by cleavage of the isolated DNA using different sets of restriction endonucleases, subjecting the samples to gel electophoresis and Southern blotting or equivalent methods and identifying the restriction fragment using a probe corresponding to a known surface gene sequence. If necessary, the DNA may be sequenced and further manipulated, for example by treatment with endonucleases, in vitro mutagenesis, primer repair or other known techniques in order to create a fragment having the desired size, carrying the desired sequence and having the appropriate termini. As is known to any one skilled in the art, the termini may be trimmed to have any desired sequence by digestion with exonucleases, filling in with the Klenow fragment of DNA-polymerase I and addition or substitution of DNA by the use of synthetic oligodeoxyribonucleotides as linkers and adapters.

The DNA sequence coding for the respective hepatitis surface antigen may then be further combined with an appropriate regulon and/or terminator, which are obtained by known techniques from the genome of a methylotrophic yeast. The respective fragments are adapted accordingly, in order to be in a suitable position relative to the translation initiation codon and the translation termination codon of the coding DNA sequence. Ligation is also carried out according to known procedures. Since these methods are well known in the art, no further explanations are provided. For a detailed description of techniques used in molecular cloning, "Molecular Cloning" by Maniatis et al. (1982) may be consulted.

Instead of ligating DNA sequences isolated exclusively from the respective natural sources, it is also possible to synthesise part or all of the desired expression cassette by means of chemical synthesis. Chemical synthesis may be conducted according to known procedures. Chemical synthesis of long oligodeoxyribonucleotides is already offered on a commercial basis. Furthermore, any combination of fragments synthesised chemically and fragments obtained from the respective natural source may be appropriate for the purposes of the present invention.

A further subject of the present invention is the provision of the URA3 gene obtained from a methylotrophic yeast. The gene was identified by complementation of the corresponding pyr F mutation of *E. coli* strain MB 1000 with plasmids constructed by random insertion of *Hansenula polymorpha* restriction fragments into a suitable vector. A plasmid was identified which complemented the deficiency of the recipient strain. The newly identified gene comprises approximately 1400 bp by measurement on agarose gels. Its restriction pattern is shown in FIG. 10 below.

In order to facilitate the construction the amplification and introduction of the expression cassette into the host microorganism it is advisable to insert this onto a vector suitable for transformation of a methylotrophic yeast. This vector may either be a linear or circular plasmid or a virus. It is possible to use so called integrative vectors, i.e. vectors lacking any autonomously replicating sequence (ARS). If these vectors are not integrated they will be lost during subsequent cell cycles.

In one preferred embodiment the vector also comprises such ARS DNA sequences capable of directing autonomous replication. Preferably these sequences are derived from the respective host microorganism. In the case of methylotrophic yeast there are several ARS described, for example HARS, and PARS. (Roggenkamp et al., 1986; Cregg et al., 1985). These sequences contain a region of DNA which functions to stably maintain the vector as an extrachromosomal entity within the host cell.

In order to facilitate the identification of transformed host organisms it is further preferred to provide selective marker-genes suitable for selection of the desired microorganism following transformation. In yeast plasmids known in the art these selective marker-genes often correspond the DNA sequences coding for enzymes involved in the amino acid or nucleic acid metabolism, which are defective in the recipient host organism to be transformed.

The same strategy may be applied for selection of transformed methylotropic yeasts. Genes, which are commonly used for selection of auxotrophic *Saccharomyces cerevisiae* strains include the LEU2, HIS3, TRP5, ARG4 and URA3 genes. Genes obtained from *Saccharomyces cerevisiae* may also be used as selective markers in transformation of methylotrophic yeast; however, growth of such transformants on minimal medium could be considerably impaired. Therefore, in a preferred embodiment of the present invention, methylotrophic yeast strains deficient in the function of any one gene involved in normal metabolism are transformed with a DNA molecule carrying a wild type homologous marker gene. The present invention provides for the first time a homologous marker gene for selection for transformants in *Hansenula polymorpha*, namely the URA3 gene. The characteristics of this gene, i.e. its restriction fragment pattern, is discussed above.

As an alternative way of selecting transformants use can be made of antibiotic resistance genes. This is a well-known approach for bacterial transformation and has been shown to be applicable to *S. cerevisiae* (Jimenez and Davies, 1980). However, for methylotrophic yeasts so far nothing is known regarding their behaviour upon contact with antibiotics such as chloramphenicol or gentamycin G418. This is believed to be the first report of selection of transformed methylotrophic yeast by subjecting the same to selective concentrations of growth inhibiting aminoglycoside antibiotics following the transformation procedure. Surprisingly, the aminoglycoside phosphotransferase derived from Tn5 (Grindley, 1980) could be shown to be active also in methylotrophic yeasts when regulated by a promoter obtained from bakers yeast. Inactivation of G418 is effective also in strains where only one or two copies of the gene are present in the cell, i.e. the gene is not required in a high copy number. According to the present invention this is a very efficient transformation/selection system in methylotrophic yeasts.

In the most preferred embodiment the vector according to the present invention is selected from the vectors pMS-2, pFS-9, pRB-S, pRB-S-269, pRB-S-271, pRB-S-322, pRB-S-326, pMPS22, pMPS21, pMPS9. The construction and use of these vectors will be described below in more detail.

A further subject of the present invention is a process for the preparation of a microorganism as described above, where a methylotrophic yeast host organism is transformed with a vector carrying the expression cassettes ec1 and/or ec2 and/or ec3 and wherein upon replication of the vector at least some of the expression cassettes are integrated by recombination with the chromosome of the yeast host organism, preferably as a multimeric repeat. As a consequence, the transformed methylotrophic organism may contain several copies of any introduced expression cassette dispersed over the whole genome, but also with a high probability that multimeric repeats of the expression cassettes are localised in one site of the genome. This type of recombination is found to occur especially in Hansenula. However, the methylotrophic yeast host organism may also be selected from any other species of methylotrophic yeast genera, for example, Candida, Kloeckera, Saccharomyces, Rhodotorula, Torulopsis and Pichia.

In the most preferred embodiment the host organism is selected from the species *Hansenula polymorpha*, exemplified by a strain having the identifying characteristics of *Hansenula polymorpha* RB 10. *Hansenula polymorpha* RB 10 was deposited with the "Deutsche Sammlung von Mikroorganismen und Zellkulturen" on Feb. 17, 1989 and received the accession No. DSM5215. *H. polymorpha* DSM 5215 forms a further aspect of this invention.

While it is preferred to perform the transformation using any one of the above-described vectors according to the present invention, it will be appreciated that other vectors may be constructed and used.

In order to obtain microorganisms containing more than one copy of an expression cassette (ec1) and optionally one or more than one copy of a second expression cassette (ec2), the following process comprising several steps is the most convenient way. According to the process, the methylotrophic host organism a) is transformed with a first vector and initially grown on selection medium, followed by incubation under non-selective conditions for several generations, b) mitotically stable transformants containing more than one expression casssette (ec1) coding for a first polypeptide are selected, c) said transformants are optionally cured of residual autonomously replicating plasmids, d) said transformants are optionally transformed with a second vector and again initially grown on selective medium, followed by incubation under non-selective conditions for several generations, e) mitotically stable transformants containing more than one expression cassette (ec1) coding for a first polypeptide and optionally one or more than one expression cassette (ec2) coding for a second polypeptide are selected, f) said transformants are optionally cured of residual autonomously replicating plasmids, steps d) to f) are optionally repeated using a third vector.

According to this process, it is possible to increase the number of expression cassettes of one type, for instance, ec1, by subjecting the cells to several subsequent cycles of transformation, growth under selective/non-selective conditions, selection of transformants and optionally curing of free plasmids. Alternatively, two or more types of expression cassettes can be introduced by either using a single type of vector containing two or more different expression cassettes or subjecting the cells to the above described cycles, wherein transformation is performed using different vectors, carrying different expression cassettes. The process according to the present invention thus provides a variety of possibilities in order to obtain a desired microorganism.

A subject of the present invention is also a composite particle, comprising at least two polypeptides corresponding to part or all of a protein having the biological activity of one of the hepatitis B surface antigens, wherein the particles present at least two antigenic determinants provided by the S-protein, preS2-protein or preS1-protein, said particle optionally containing host specific lipids. In general, the particles are made of a majority of a protein having the antigenic characteristics of the S-protein, which also constitutes about 80 to 90% of naturally occurring 20 nm particles. The composite particles further may comprise either any protein having the antigenicity of preS1-protein specific domains, i.e. peptides corresponding to at least part of the N-terminal 108 (or 119) amino acids of preS1-protein, or/and any protein having the antigenicity of preS2 specific domains, i.e. peptides corresponding to at least part of the 55 amino acid preS2-specific domain.

The presence of two or more different proteins having the biological activity of hepatitis B surface antigens in one particle was not a known approach for the design of yeast-derived anti-hepatitis B vaccine at the relevant priority date of the present application. Yeast-derived particles or aggregates obtained by that date had contained exclusively either the S protein, or the preS2-protein or the preS1-protein, i.e. only one of the three possible proteins. It had been shown by Valenzuela et al. (1985) and Itoh et al. (1986) that preS2-protein was assembled into particles, while preS1-protein had been reported to form either a mixture of small particles (2 or 3 nm in diameter) or a polydisperse population of large aggregates some 15 to 50 nm in diameter (Kniskern et al., 1988; Imamura et al., 1987). Before the filing date of the present application, however, a publication appeared (EP-A-0 341 746) which reports a process for the enhanced production of antigenic particles consisting essentially of hepatitis B S protein and preS2 protein.

Rutgers et al. (1988) report that on preS2-protein and preS1-protein particles or aggregates, the S-protein encoded epitopes are masked as these particles are less reactive in the AUSRIA assay. This may have a deleterious effect on the immune response with respect to S-protein when particles composed of homogenous preS protein species are used as, immunogens for vaccine purposes.

The present invention as claimed provides new composite particles comprising more than one species of hepatitis B surface antigen. By analogy with particles comprising only one protein produced in S. cerevisiae, the particles according to the present invention will normally comprise host-specific lipids.

In a preferred embodiment the composite particles according to the present invention comprise more than 1% preS1-protein, the rest of the protein being S-protein and optionally some preS2-protein. Preferred particles, however, contain 1–50%, especially 1–25% preS1-protein, the rest being the same as above. In especially preferred embodiments, the ratio of preS1-protein to S-protein is between 1:1 and 1:100, preferably 1:2, 1:8 or 1:15.

The particles according to the present invention are at least partially glycosylated. A proportion of the pre S1-proteins in methylotrophic yeasts are glycosylated, as indicated by the detection of bands with molecular weights of 45 kD, 38 kD and 39 kD. It will be appreciated by one skilled in the art that the number and size of preS1 protein species observed by immunoblotting may present some apparent variability. Detection of the 45, 38 and 39 kD bands will depend, inter alia, on their resolution during polyacrylamide gel electrophoresis, interference from other yeast proteins and variations in the efficacy of the procedures used in immunoblotting. Further, the method chosen for the preparation of crude cell extracts and the specific composition of the buffer used for extraction may also influence the detection of a particular band. The relative proportions of the three species may also vary with growth conditions. Furthermore, estimates of molecular weight are also subject to experimental variation and depend on the standards used for calibration. Glycosylation of S-protein has not been observed.

The composite particles described above are conveniently prepared by cultivating a methylotrophic yeast strain according to the present invention in a suitable culture medium. Using a regulated system of expression, the synthesis of particle components can be controlled to avoid their expression affecting cell growth. Thus at any desired cell density, methanol regulon-controlled protein synthesis may be derepressed to permit expression of the heterologous protein. Upon coordinated expression of different types of hepatitis B surface antigens in close proximity, particle formation occurs. These particles can be isolated from the culture by means of well-known techniques, for example isopycnic centrifugation, chromatography and other methods known in the art.

The same method may also be applied in order to obtain particles or aggregates comprising only one species of surface antigen, when appropriate strains are used.

In a preferred embodiment, protein synthesis directed by the expression cassette starts upon depletion of repressing carbon sources. The cells, which were previously subject to catabolite repression, begin expression upon dilution of the repressing agent. The effect of derepression can be further enhanced by addition of methanol, which results in induction of a methanol responsive regulon. Addition of methanol results in up to 10 fold enhancement of heterologous protein synthesis.

In a preferred embodiment, the culture medium contains glycerol as a carbon source. Glycerol is a carbon source having a minimal catabolite repressing effect. Glycerol concentrations of up to 0.3% do not effect repression. Therefore, when using a culture medium containing glycerol, this carbon source does not have to be removed completely before the optional addition of methanol.

Fermentation of the methylotrophic yeast strains according to the present invention is carried out between 30 to 40° C. using a medium maintained at pH 3 to 7, preferably pH 4 to 6. Examples of media, are given below.

In a preferred embodiment of the invention the composite particle comprises all or part or parts of the S-protein and all or part or parts of the preS1-S2-S protein (L protein) of HBV.

In an especially preferred embodiment of this invention the composite particle may comprise any of the modified L proteins disclosed both generically and specifically hereinbelow.

In a particularly preferred embodiment the modified L protein corresponds to a 280 amino acid polypeptide containing residues 12–52, 133–145 and 175–400 relative to the ORF on a HB virus of ad serotype.

In yet a further preferred embodiment of this invention the composite particle may contain hepatitis B surface antigen polypeptides of differing subtypes to broaden the range of protection. That is the S-protein may be of ad subtype specificity and the preS1-protein and/or the modified L protein and/or the preS2-protein of ay subtype or vice versa.

The subject of the present invention is further a composition of matter comprising the new composite particle or hepatitis B surface antigen protein produced according to the present invention. Further components of the inventive composition may be stabilizers, buffering substances, diluents, salts such as NaCl, or sugars.

As outlined above, the initial purpose of the present invention is to provide a vaccine against hepatitis B virus. Therefore, a vaccine comprising a composite particle as described above or hepatitis B surface antigen produced according to the present invention is a further subject of the present application. The vaccine may comprise further substances, for example salts, stabilizers, adjuvants, and/or other physiologically acceptable additives. The vaccine comprising composite particles elicits formation of antibodies directed against at least two of the possible antigenic determinants of hepatitis B surface antigens. Due to the presence of pres1 specific and preS2 specific domains, even individuals who did not respond to presently available vaccines, may be protected against hepatitis B infection. In general the vaccine according to the present invention will evoke a broader immune response than present vaccines and furthermore can be produced at lower costs due to the high amount of expression per cell and the high cell density.

The present invention has also proved to be useful for the development of a test kit. By providing a composition comprising the composite particles according to the present invention, it is possible to monitor the formation of immune complexes formed between antibodies of an infected individual with such particles. The test kit requires further provision of a detection agent, for example, a goat/anti-human IgG antibody labelled by any of the known techniques. The antibody, which can of course also be derived from any other mammal, may for example be coupled to an enzyme or may be radioactively labelled to effect detection. The advantage of a test kit responsive to antibodies against preS1 and preS2 specific domains is the possibility of early detection of HBV infection, since anti-preS1 and anti-preS2 antibodies appear prior to anti-S antibodies during HBV infection in man (Petit et al., 1986). Thus the test kit according to the invention provides a convenient means for early diagnosis of this highly infective disease.

In a further aspect the present invention provides a modified large surface protein (hereinafter modified L protein) of hepatitis B virus (HBV). One such modified L protein has an L protein sequence characterized by the absence of sites preferentially attacked by proteases. Elimination of these sites provides a less protease sensitive molecule, which upon expression produces a protein readily purified in particle form.

Another aspect of the present invention is a modified L protein characterized by the absence of an amino acid necessary for myristylation of the protein.

In yet another aspect the present invention includes a modified L protein which is characterised by the absence of several potential glycosylation sites. Elimination of the glycosylation of the L protein improves the presentation of epitopes which are shielded, distorted or modified by glycosylation of the protein which occurs during expression in yeast hosts. The modified, deglycosylated L protein presents the protective B epitopes and significant $T_H$ epitopes of the preS1, preS2 and S region in their correct conformation, well exposed-on the surface of the resulting particle.

A further aspect of the present invention includes a modified L protein characterised by a deletion of a part of the preS2 region, which includes the human serum albumin (pHSA) binding site. This modification of the L protein thereby eliminates the potential tolerance or auto-immune problems linked to the presence of the pHSA receptor without losing the major B epitopes of the preS2 region.

In still a further aspect of this invention, a modified L protein is provided which is characterized as non-glycosylated, and having diminished protease sensitivity and diminished pHSA binding capacity. This protein contains the preS1 region sequences corresponding to amino acid residues 12 to 52 fused to preS2 region sequences corresponding to amino acid residues 133–145, followed by the entire coding sequence for the S protein in a continuous reading frame.

The modified L proteins of this invention may be expressed not only in methylotrophic yeasts as thus far discussed but also in other yeast expression systems which produce the proteins as particles retaining the major antigenic sites encoded by the three domains preS1, preS2 and S. The modified L proteins may also be co-expressed with the S protein in yeast to form particles of mixed subunit composition. Other expression systems, e.g., bacterial, insect, mammalian may also produce the modified L proteins in various forms.

As another aspect this invention also provides novel DNA sequences coding for the modified L proteins of the present invention. In another aspect of this invention, such DNA sequences may be incorporated in vectors under the control of appropriate regulatory sequences.

As still another aspect there is provided a method for producing a modified L protein of HBV as described above involving culturing a yeast cell transformed with a yeast expression plasmid expressing a selected modified L protein gene sequence under control of suitable regulatory sequences and employing suitable culture conditions. The modified L protein may also be co-expressed in a yeast host with S protein. The resulting L protein may be isolated from the culture or cell lysate by conventional techniques. The modified L protein may be isolated in the form of particles of either mixed or homogeneous subunit composition depending on its co-expression with S protein.

As still a further aspect, the invention provides a method for producing modified L proteins in other expression systems, including bacterial expression systems; insect cell expression systems, e.g., baculovirus systems; mammalian cell expression systems; vaccinia virus systems and plant expression systems.

Still a further aspect of this invention are vaccines comprising one or more modified L proteins of this invention, alone or in combination with other vaccinal agents and pharmaceutically acceptable vaccinal carriers and adjuvants. The vaccines of this invention comprising the modified L proteins described herein may also include the modified L protein in the form of a particle of mixed subunit composition with other peptides i.e. S protein.

From the foregoing it will be appreciated that the novel modified large (L) hepatitis B surface protein molecules may be used alone or with other HBsAg or HBV components to provide vaccinal agents for use in immunizing persons against HBV infection. The invention also involves expressing a modified L protein in a suitable host cell under suitable regulatory control.

The modified L protein of the present invention is characterized by deletion, insertion or modification of a variety of amino acid sequences in the preS region. It is to be understood that the L molecule to be modified and expressed here has already been deleted for its first eleven amino acids and contains 163 amino acids in the preS1 region (see co-pending U.S. patent application Ser. No. 009,325 incorporated by reference herein). The resulting reduction in size of the preS region facilitates particle formation in the host cell and enhances various biophysical properties of the molecule, which may make the modified L particle particularly desirable for vaccinal manufacture and use. For example, the shortened preS regions of the present invention may enable better presentation of the S and preS epitopes on the particle for interaction with the immune system, thereby enhancing immunogenicity.

In one embodiment, the present invention provides a modified L protein deleted for the Gly 13 amino acid residue in the preS1 region. The L protein expressed in yeast carries a myristyl group covalently attached in an amide linkage, as disclosed in copending U.S. patent application Ser. No. 07/009,325. An N- terminal Gly residue is an essential requirement for the myristylation of a protein [Towler and Gordon, *Ann. Rev. Biochem.*, 57:69–99 (1988)]. Therefore, one suitable modified L protein of this invention is encoded by DNA having a deletion of the Gly13 codon (GGG) from the nucleotide sequence encoding the L protein. This deletion results in the synthesis of a non-myristylated L protein.

As used herein the symbol Δ denotes deletion: Thus, for example, ΔGly13 modified L means modified L protein lacking amino acid residue 13 (glycine).

Another embodiment of the present invention is a modified L protein deleted for one or more of its potential glycosylation sites. The L protein expressed in yeast carries an N-linked oligosaccharide chain at Asn123 and several O-linked mannose chains linked to Ser and Thr residues in both the pres1 and preS2 regions of the molecule as described in U.S. patent application Ser. No. 009,325, identified above [see, also, Rutgers et al, "Viral Hepatitis and Liver Disease" ed. A. J. Zuckerman, A. R. Liss, New York, pp. 304–308 (1988)]. To remove the N-glycosylation site which is characterized by the sequence Asn-X-(Ser or Thr), where X may be any amino acid, the sequence at amino acid positions 123–125 is altered. The N-linked glycosylation site may be eliminated by deleting or replacing the amino acids at positions 123 and 125, deleting amino acid 124 or deleting the entire 123–125 sequence. To destroy the O-linked glycosylation sites, all or some of the Ser and Thr residues in the L sequence are deleted from, or replaced with, other amino acids in the protein. The L protein expressed from illustrative plasmid pRIT13192 is characterized as wholly or partially non-glycosylated.

Another modified L protein of the invention contains a deletion in the preS2 sequence at amino acid residues 120–132 of the preS2 region responsible for binding of polymerized human serum albumin (pHSA) [see Machida et al, cited above]. pHSA binding is greatly diminished on the proteins lacking this sequence.

Another modified L protein according to the invention is characterized by deletion or alteration of the protease sensitive sites. Protease sensitive peptide bonds exist in the preS sequence behind the Arg residues around position 100 in the pres1 region [Heermann et al., Intervirology 28, 14–25 (1987)] and behind amino acid residues Arg137, Gly149 and Arg167. Deletions or other modifications introduced in the coding region of the L protein to remove some or all of the codons for these residues produce an L protein less sensitive to protease action.

The deletions introduced in the coding region of the L protein to form modified L proteins preferably leave untouched the codons for amino acids 21–47 and 133–145. These sequences are believed to provide the modified protein with the capacity to induce preS-specific antibodies correlated with immune protection [see, e.g., Itoh et al, supra].

Construction of an exemplary yeast expression plasmid pRIT12979 encoding the ΔGly13 L protein is described in Example F.1 below. Analysis of the modified L protein expression from plasmid pRIT12979 for expression level, post-translational modifications and macromolecular assembly is described in Example F.2.

Another modified L protein, devoid of all three of the above mentioned properties, i.e. to function as a substrate to yeast glycosylation enzymes, pHSA binding capacity and protease sensitivity, and modified by removal of the codons for amino acid residues 53–132 and 146–174 of the preS region is illustrated in plasmid pRIT13192, described in Example F.3 below. Plasmid pRIT13192 contains the codons for residues 12–52 and 133–145 of the preS region. Analysis of L protein expression from plasmid pRIT13192 is also described herein (Example F.4). The L protein expressed from pRIT13192 thus shows a greatly reduced pHSA binding capacity, an improved protease resistance and less glycosylation.

Yet another exemplary modified L protein of the present invention combines the deletions introduced in the L protein coding sequences of pRIT12979 and pRIT13192. The L protein expressed by this sequence codes for a non-myristylated, less glycosylated, less protease sensitive L protein with diminished pHSA binding capacity. Construction of the yeast expression plasmid pRIT13193 bearing this modified L sequence insert is also described in detail in Example F.3 below.

Modified L protein coding sequences, including the entire S coding sequence, for use in the present invention can be prepared from these S and preS protein coding sequences of Table A by conventional site specific mutagenesis [see, e.g., Botstein et al, Science, 229:1193 (1985)] or recombinant DNA techniques, [see, e.g., T. Maniatis et al, Molecular Cloning, A Laboratory Manual, Cold Spring Harbor Laboratory (1982)]. The amino acid position numbers referred to below will correspond with the position numbers in Table A for clarity. However, other published versions of the S, and preS sequences can be used in preparing the modified L proteins of this invention by one of skill in the art.

For example, the S protein can be isolated from DNA extracted from Dane particles in infected human serum by filling in the single strand region with a DNA polymerase, preferably the endogenous polymerase, followed by digestion with a restriction endonuclease. The choice of endonuclease will depend, in part, on the particular Dane particles. For example, the HBsAg coding sequence of HBV DNA of certain Dane particles of the adw serotype can be isolated on a single BamHI fragment; the HBsAg coding sequence of HBV DNA of certain Dane particles of the ayw serotype can be isolated on a HhaI fragment. HBV DNA of Dane particles of the same serotype may also exhibit different patterns of restriction sites.

Construction of the modified L protein sequences of this invention can be accomplished by use of intermediate vectors. Techniques for cloning DNA fragments in phages are disclosed, for example, by Charnay et al, Nature, 286:893–895 (1980) and Tiollais, United Kingdom Patent Application 2,034,323.

The modified L protein of this invention may be constructed in a recombinant DNA molecule or vector. A recombinant vector of this invention comprises the modified L protein coding sequence of this invention operatively linked to a regulatory region. Such vector may also additionally contain a replicon depending upon preference and/or the host to be employed. By the term "replicon" is meant that minimum region of DNA which functions to maintain stably, and extrachromosomally, a recombinant vector in a eukaryotic or prokaryotic host organism transformed with such vector. Such replicons are well-known in the art. By the term "regulatory region" is meant any DNA sequence which contains a promoter region and other sequences necessary for transcription of a coding sequence which regulates transcription of a structural gene's coding sequence. Such regulatory regions are well-known in the art.

Such a vector can be prepared by conventional techniques such as by inserting the modified protein coding sequence of this invention into a vector already containing a replicon and regulatory region in such a way that the DNA molecule is operatively linked to such regulatory region. This DNA molecule, or an expression cassette containing the modified L protein coding sequence, can be constructed by conventional techniques, such as by ligating the L coding sequence to the regulatory sequence.

Restriction of DNA to prepare DNA fragments used in the invention, ligation of such fragments to prepare recombinant DNA molecules used in the invention and insertion into microorganisms are carried out by known techniques, such as techniques disclosed in the previously and subsequently cited references. Conditions are selected to avoid denaturation of the DNA and enzymes. Restriction enzymes and ligases used in carrying out this invention are commercially available and should be used in accordance with instructions included therewith. T4 DNA ligase is the preferred ligase.

The various fragments and final constructions used for the expression of the modified L proteins, and the components of the vectors carrying these coding sequences for expression in host cells in the method of the present invention may be joined together using with conventional methods known to those of skill in the art. In many cases, genes have been isolated and restriction mapped, as well as sequenced. To that extent, one can select the sequence of interest, such as the HBV envelope protein coding sequence, by restriction of the gene, employing further manipulation as necessary such as resection with Bal31, in vitro mutagenesis, primer repair, or the like, to provide a fragment of a desired size, including the desired sequence, and having the appropriate termini. Linkers and adapters can be used for joining sequences, as well as replacing lost sequences, where a restriction site employed was internal to the region of interest. The various fragments which are isolated, may be purified by electrophoresis, electroeluted, ligated to other sequences, cloned, reisolated and further manipulated.

The use of regulatory regions for controlling transcription of the modified L gene of interest may allow for growing the host cells to high density with no or low levels of expression of the structural gene, and then inducing expression by changing the environmental conditions, such as nutrient, temperature, and the like.

The vector carrying the L protein coding sequence is transformed into, and expressed in a selected host cell by conventional techniques. The cell is then cultured in appropriate culture media, i.e., media which enable the host to survive and express the modified L protein in recoverable quantity. For example, where a yeast host cell is selected, an exemplary medium for such use is Yeast Nitrogen Base minimal medium. The appropriate culture media may be selected by one of skill in the art depending upon the particular host employed in the method.

The isolation of the modified L protein molecule of the invention may be from a cell lysate or extract of the host cell culture medium depending upon the cell's ability to secrete the modified protein. Recovery of the protein of this invention is performed by conventional protein isolation techniques.

For producing modified L proteins of this invention, a suitable host cell or cell line may be selected. Suitable cells or cell lines may be yeast cells. Many strains of yeast cells known to those skilled in the art are available as host cells for expression of the modified L proteins of the present invention. In the practice of this invention, any species of yeast may be employed. In one aspect, the examples below employ Saccharomyces, specifically *S. cerevisiae*. Numerous strains of *S. cerevisiae* are available from public depositories and laboratories, e.g., American Type Culture Collection, Rockville, Md.

In another aspect *Hansenula polymorpha* may be used.

Other yeast species may also be employed including, without limitation, Hansenula, Pichia, Candida, Kluyveromyces and Schizosaccharomyces.

Additionally, other species of eukaryotic host cells, e.g., mammalian cells, such as Chinese hamster ovary cells (CHO) or 3T3 cells, may be employed as host cells for expression of the modified L proteins described herein. Selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7):1750–1759 (1985) or Howley et al, U.S. Pat. No. 4,419,446. Other suitable mammalian cell lines, are the monkey COS-1 cell line, and the CV-1 cell line.

It will be realised that some of the deletions introduced in the L protein coding sequence described above have altered the internal sequences engaged in the transcription and translation of M and S specific mRNA in mammalian cells. Such a modified L protein coding sequence allows, therefore, independent expression of S and modified L protein in a mammalian cell harbouring their individual expression cassettes.

Similarly useful as host cells suitable for the present invention are bacterial cells. For example, the various strains of *E. coli* (e.g., HB101, MC1061 and strains used in the following examples) are well-known as host cells in the field of biotechnology. Various strains of *B. subtilis,* Pseudomonas, other bacilli and the like may also be employed in this method.

Additionally, where desired, insect cells may be utilized as host cells in the method of the present invention. See, e.g. Miller et al, *Genetic Engineering,* 8:277–298 (Plenum Press 1986) and references cited therein.

Some viruses may also be employed to express the L proteins of this invention, such as baculoviruses or vaccinia viruses. Selection of appropriate host cells is within the ability of one of skill in the art, as is the selection of appropriate culture conditions, media and vector components appropriate to expression in a selected host cell.

In the expression systems described above and below in the Examples, any known promoter capable of controlling the expression of the protein coding sequences in the selected host cell may be selected. Where the host cell of choice is a yeast cell, the promoters useful for expressing the modified L protein cassettes may include the strong promoter TDH3 or other constitutive or regulated promoters which allow modulation of the level of the L protein depending on the composition of the growth medium. Additionally, for example, PGK, ARG3, and APH1 are illustrative promoters useful in the vectors of the present invention.

The present invention also provides for expression of the modified L proteins of this invention as part of an HBsAg particle of mixed polypeptide composition, as described in detail in copending U.S. patent application Ser. No. 07/368,401, which is incorporated by reference herein. The method involves coexpressing in a yeast cell a first protein S and a second protein X-S, where S is substantially the major surface protein of HBV and where X, for purposes of the present invention, is a modified preS sequence encoded by a functional DNA coding region fused in phase to the S coding sequence.

Where reference is made to co-pending U.S. patent application Ser. No. 07/368,401 it should be noted that substantially the same disclosure is to be found in Jacobs et al., Gene 80: 279–291 (1989).

According to this method the S protein coding sequence is coexpressed with the modified L protein amino acid sequence. The coding regions of the L protein, as well as the sequence for the S protein may be constructed as described above using conventional chemical synthetic or recombinant DNA technology. The modified L proteins are incorporated together with S proteins into particles of mixed subunit composition.

In the construction of the X-S proteins comprising modified L proteins of the present invention, S is preferably the entire mature surface protein (about 226 amino acids) of HBV (see Table A). Alternatively, the S protein may be encoded by an S protein coding sequence of the HBV genome, wherein S is substantially the same as an authentic HBsAg S protein. Truncates of S can also be employed in the construction of the modified L protein containing mixed particles, as long as particle assembly is not adversely affected.

The S protein coding sequence is placed into a first expression cassette employing conventional techniques to allow expression of the S protein in the yeast host. The S protein coding sequence or a substantial portion thereof is employed in a fusion with portions of the preS coding sequence and placed into a second expression cassette to allow production of a modified L protein of this invention.

A vector, constructed by conventional techniques as described above, carrying the S protein expression cassette and one or more vectors carrying the modified L protein expression cassette are transformed into into a yeast host cell by conventional techniques.

Alternatively, S protein expression cassettes and expression cassettes for one or more modified L proteins are placed together on the same vector which is transformed into a yeast host cell.

Vectors that can be used are Ty integrative vectors as described in detail in co-pending U.S. patent application Ser. No. 386,401. Another alternative method employs compatible autonomously replicating vectors that carry the desired expression cassettes and transform the yeast host cell.

Examples of vector systems are described in detail in Mellor et al., *Yeast,* 2:145 (1986); Boeke et al., Cell, 40,491 (1985), Boeke et al., *Cell,* 42–507 (1985) and copending U.S. patent application Ser. Nos. 101,463; 233,631; 368,401 and 009,325 (European Patent Application Publication No. 0 278 940) which applications and references are incorporated herein by reference.

Additionally other species of host cells may be employed for expression of the composite HBsAg particles of mixed polypeptide composition described herein. Suitable eukaryotic hosts are the same as those listed hereinabove for expression of the modified L proteins of the invention, e.g. mammalian cells such as CHO cells and the like. Insect cells and viruses such as baculoviruses and vaccinia viruses mentioned hereinabove may also be used as host cells.

A preferred embodiment of the method according to the present invention employs Ty integrative vectors carrying the S protein expression cassette and autonomously replicating plasmid vectors carrying the modified L protein expression cassette. The use of Ty vectors carrying the S protein expression cassette allows these sequences to be stably integrated into the chromosomes of the yeast host cell. Such integrations are stable due to their low frequency of excision. The vectors are thus homogeneously distributed in the cell population, allowing a similar rate of protein synthesis in each cell.

Transformation into these cells of autonomously replicating plasmids carrying the expression cassette for the modified L protein ensures that for a definite amount of S protein synthesis in each cell, the level of modified L protein synthesis varies according to the copy number of the plasmid present in the cell. Due to the variable S/L expression ratio in each cell, the particles derived from a total cell population will dispose the peptides in all possible associations.

In a further preferred embodiment both the S protein expression cassette and the modified L protein expression cassette may be inserted on Ty integrative vectors and separately integrated into yeast host cells of opposite mating types. Strains carrying the desired numbers of S cassette and modified L cassette integration events may then be crossed to obtain diploid cells expressing both the S and modified L polypeptides. If desired haploid segregants carrying both types of expression cassette may be obtained by sporulating such diploids.

The cell may be cultured in appropriate culture media, i.e., media which enable the host to express the S protein and modified L protein in particles of mixed subunit composition in recoverable quantity.

Resulting modified L proteins will be produced simultaneously in yeast cells together with the S protein and assembled as mixed composite particles. Such particles are herein defined as a multimeric assembly of two or more polypeptides into a particulate structure, which is therefore characterised by a composite nature being of mixed polypeptide composition. The different peptides are disposed in a spatial association at the surface of the mixed particles. The presence of the novel modified L protein on the HBsAg particle will elicit an immune response similar to that associated with recognition of the native determinant. The present invention thereby enables the production of HBsAg particles in yeast which mimic natural particles insofar as they contain the essential antigenic sites from the S, M and L proteins of HBV.

The isolation of the mixed particle of the invention from a cell lysate or extract of the culture medium is performed by conventional protein isolation techniques.

In the practice of this method of this invention, any species of yeast host for which transformation, cloning and expression systems are available may be employed in developing "mixed particles" of HBsAg.

In other yeast genera no Ty sequences are present and therefore vector systems must be designed to provide coexpression of the S and modified L protein coding sequences in these genera to create the mixed particles described. Therefore, expression cassettes may be designed for integration into the yeast chromosomes employing other repetitive DNA sequences or plasmids such as ARS based plasmids in yeast such as Pichia, allowing integration into the chromosomes. An example of such applicable ARS plasmids is described in Cregg et al, *Mol. Cell. Biol.,* 5(12):3376 (1985).

In the expression systems described above, e.g. both the Ty expression systems and others, the regulatory element comprises a promoter which effects RNA polymerase binding and transcription. Regulatable, i.e., inducible or derepressible, promoters, can also be used. A variety of useful promoters are available for expression of heterologous polypeptides in yeast. These include the copper inducible metallothionein gene (CUP1) promoter and the constitutive promoter of the glycolytic genes, glyceraldehyde-3-phosphate dehydrogenase (TDH3) and alcohol dehydrogenase (ADH). Regions for transcription termination in yeast are derived from the 3 end of any of several yeast genes, for example, the gene for iso-1-cytochrome C (CYC1). Expression systems for use in Kluyveromyces are disclosed, e.g., in PCT WO83/04050, Hollenberg et al; in Schizosaccharomyces, e.g., in EP-A-107170, Yamomoto; in Pichia, e.g., in Cregg et al, *Bio/Technology,* 5:479 (1987); and in Hansenula, e.g., in EP-A-299108, Hollenberg et al.

Specifically provided by the examples of this invention are *S. cerevisiae* strains capable of synthesizing S protein as a result of the genomic integration of S protein expression cassettes directed by Ty based vectors. One such vector, pRIT13133-L, containing the TDH3-S coding sequence—ARG3 cassette and the URA3 marker is described in Example 1 of co-pending U.S. patent application Ser. No. 368,401. Another Ty1 vector, pRIT13034-L, contains the same expression cassette and URA3 marker but contains in addition the CUP1 gene which can be used as an additional marker in $CUP1^s$ or cup1Δ recipient yeast strains.

Preferred yeast strains are devoid of functional chromosomal CUP1 genes, which are sensitive to copper toxicity, in order to readily select transformants having integrated several copies of vectors. Two preferred cup1Δ yeast strains EJ cup1Δ3d and EJ cup1Δ7b are described in Example 9 of co-pending U.S. application Ser. No. 368,401.

Yeast strains containing several integrated copies of either pRIT13133-L or prRIT1034-L are described in the Examples below.

Transformation into these yeast strains of autonomously replicating yeast expression plasmids carrying an expression cassette for a modified L protein is also described in the Examples below.

Diploid yeast strains carrying several integrated copies of both S and modified L expression cassettes are described in Example F.10 below.

The method of the present invention for producing such modified L proteins, alone or in particles of mixed subunit composition has advantageous utility in the production of vaccines to pathogenic microorganisms. For example, the modified L proteins described in the various vaccine formulations comprising hepatitis B surface antigen and may provide benefits not obtained with known HBV vaccines. The HBsAg particle of mixed subunit composition containing a modified L protein resembles particles or filaments or virions present in the blood of HBV infected persons that contain preS2 and preS1 epitopes exposed at their surface in addition to epitopes from the major proteins and may also prove useful in novel vaccine formulations. The modified L proteins or mixed particles of mixed subunit composition containing them may have immunogenic properties that are not obtained with individual mixtures of S, M and L proteins.

In further embodiment of this invention the particles of mixed subunit composition may contain modified L proteins and S proteins with different subtype determinants so as to broaden the range of protection. That is, the modified L protein may be of ay subtype specificity and the S protein of ad subtype or vice versa.

Thus this invention encompasses vaccines containing the modified L proteins of the invention or a particle containing the modified L protein either in mixed (S, modified L) or homogeneous (modified L protein) subunit form. Such vaccine will contain an immunoprotective quantity of the particles or modified L proteins, i.e., enough of the proteins or particles are administered to elicit sufficient protective antibody response against HBV without serious side effects. Such vaccines may be prepared by conventional techniques. For example, a vaccine for stimulating protection against HBV infection in humans may contain the particle and/or the modified L proteins described above and a suitable conventional carrier. The particle or the L protein may be in an aqueous solution buffered at physiological pH for direct use. Alternatively, the protein or particle can be admixed or adsorbed with a conventional adjuvant, such as aluminum hydroxide or aluminum phosphate. Such a particle or modified L protein may also be combined with other immunogens to prepare combination vaccines. See, e.g., New Trends and Developments in Vaccines, eds. Voller et al, University Park Press, Baltimore, Md. (1978).

These modified L proteins, alone or in particles of mixed or homogeneous subunit composition, as described, thus broaden the spectrum of antibodies against HBV, and may provide an earlier response to viral challenge by the person vaccinated with the vaccines containing these proteins. Additionally the vaccines containing these modified L proteins may enable persons who do not respond to S proteins to mount a preS response, or may augment or enhance the S response.

Another use for the particles of this invention and/or the modified L proteins may be as probes or reagents for detection of HBV or HBV derived proteins or anti-HBV antibodies in biological samples by various conventional immunoassays and the like.

It will be appreciated that all vaccines described herein can be administered by an appropriate route, e.g., by the subcutaneous, intravenous or intramuscular routes. The amount of the immunogen in each vaccine dose is selected by the attending physician with regard to consideration of the patient's age, weight, sex, general physical condition and the like. The amount to induce an immunoprotective response in the patient without significant adverse side effects may vary depending upon the immunogen employed and the optional presence of an adjuvant. Generally, it is expected that each dose will comprise 1–1000 micrograms of protein, preferably 1–200 micrograms. Initial doses may be optionally followed by repeated boosts, where desirable.

Accordingly the present invention further provides a method of treating or preventing hepatitis B infection in humans which comprises giving to a patient in need thereof a protective amount of a vaccine according to the invention.

Especially preferred vaccines according to the invention are those which comprise composite particles of structure (L*, S) where L* is as defined below and S denotes the S-protein of hepatitis B surface antigen, most preferably expressed in *S. cerevisiae* or *H. polymorpha* as described herein.

As used herein the symbol L* denotes a modified L protein comprising residues 12–52, 133–145 and 175–400 relative to the large open reading frame on HB virus of ad serotype shown in Table A hereinabove. The symbol Δgly L* similarly denotes a modified L protein comprising residue 12 followed by residues 14–52, followed by residues 133–145 and 175–400.

The following Examples illustrate the invention.

Materials

1. Plasmids

Plasmids mentioned in the specification are described in Part A below.

2. Yeast strains

*Hansenula polymorpha* RB 10 (ura 3) is a mutant of *Hansenula polymorpha* ATCC 34438, obtained by mutagenesis using ethylmethansulfonate (EMS) essentially as described by Roggenkamp et al. (1986).

3. Enzymes

Restriction endonucleases, T4 DNA ligase and other enzymes used, were obtained either from Boehringer, Mannheim, FRG or Bethesda Research Laboratories, Eggenstein, PRG. The enzymes were used according to the instructions of the respective manufacturer.

4. Immunological Reagents

Monoclonal antibodies used included the following:

a) S1.1: mouse monoclonal antibody specific for the S1 domain of pres1-protein (SmithKline Biologicals, Rixensart, Belgium)

b) S2.1, S2.2 and S2.5; mouse monoclonal antibodies specific for the S2-domain of hepatitis B surface antigen (SmithKline Biologicals, Rixensart, Belgium).

Antibodies specific for the S1-domain and S2-domain of hepatitis B surface antigen are referred to as "preS-antibodies".

c) RF6: Mouse monoclonal antibody specific for a denaturation and reduction resistant epitope in the S domain of hepatitis B surface antigen (H. Thomas, Royal Free Hospital, London).

d) RF1: Mouse monoclonal antibody specific for a conformational dependent epitope located in the S-region (H. Thomas, Royal Free Hospital, London).

e) HBS1: Mouse monoclonal antibody directed aginst a denaturation and reduction resistant epitope of plasma-derived HBsAg, located in the S-region (SmithKline Biologicals Rixensart, Belgium). This monoclonal competes in binding experiments with Mab RF6.

Antibodies a), b) and e) were prepared by the applicant according to standard procedures by fusion of mouse spleen cells with myeloma cells. For the method reference is made to Köhler and Milstein, 1975. Methods are disclosed in Goding, Monoclonal Antibodies, Principles and Practice, Academic Press, London 1983. Other monoclonal antibodies mentioned hereinbelow were prepared similarly.

f) AUSRIA (Abbott Laboratories, Wiesbaden-Delkenheim, FRG and Louvain-La-Neuve, Belgium): commercial kit containing polyclonal antibodies directed against native conformational epitopes.

g) AUSZYME (Abbott Laboratories, Wiesbaden-Delkenheim, FRG and Louvain-La-Neuve, Belgium): commercial kit containing monoclonal antibodies directed against a native conformational epitope.

The antibodies mentioned under f), g) are commercially available. They do not react with monomeric hepatitis B surface antigen.

h) AUSAB (Abbott Laboratoires, Louvain-La-Neuve, Belgium): Commercial kit for detection of anti HBsAg-antibodies.

5. Media

Pepton 190, yeast extract, Casamino acids and yeast nitrogen base used for preparation of media were purchased from Gibco Ltd., Paisley, U.K.

In order to prepare agar plates, 18 g agar (Gibco Ltd.) per liter were added prior to autoclaving the respective medium.

a) SMR: Semi-rich non-selective medium

| Pepton 190 | 2 g/l |
| --- | --- |
| Yeast extract | 1 g/l |
| Casamino acids (Pepton 5) | 3 g/l |
| Yeast nitrogen base W/O $(NH_4)_2SO_4$ | 1.4 g/l |
| $(NH_4)_2SO_4$ | 5 g/l |
| Carbon sources: glucose | 20 g/l |
| or glycerol | 20 g/l |
| or methanol | 10 g/l |

SMR containing methanol is also called Met-SMR.

b) YNB: Selective medium

| Yeast nitrogen base without $(NH_4)_2SO_4$ (Gibco or Difco) | 1.4 g/l |
| --- | --- |
| $(NH_4)_2SO_4$ | 5 g/l |
| Carbon sources: glucose | 20 g/l |
| or glycerol | 20 g/l |
| or methanol | 10 g/l | c) YEPD: Non-selective rich medium.

| Yeast extract | 10 g/l |
| --- | --- |
| Pepton 19.0 | 20 g/l |
| Glucose | 20 g/l |

If necessary, 1 mg gentamycin G418 was added per 1 ml of medium.

d) S-medium

| COMPONENT | AMOUNT PER LITER |
| --- | --- |
| $(NH_4)_2SO_4$ | 5 g |
| $KH_2PO_4$ | 4 g |
| $MgSO_4.7\ H_2O$ | 2 g |
| NaCl | 0.1 g |
| L-Histidine monohydrochloride | 10 mg |
| LD-Methionine | 9 mg |
| LD-Tryptophan | 9 mg |
| $H_3BO_3$ | 2 mg |
| $CuSO_4.5\ H_2O$ | 0.16 mg |
| KI | 0.4 mg |
| $FeCl_3.6\ H_2O$ | 0.8 mg |
| $MnSO_4.H_2O$ | 1.6 mg |
| $Na_2MoO_4.2\ H_2O$ | 0.8 mg |
| $ZnSO_4.7\ H_2O$ | 1.6 mg |
| Biotin | 0.16 mg |
| Ca-pantothenate | 32 mg |
| Folic acid | 0.16 mg |
| Inositol | 160 mg |
| Niacin | 0.4 mg |
| p-Amino-benzoic acid | 0.2 mg |
| Pyridoxine hydrochloride | 32 mg |
| Riboflavin | 0.2 mg |
| Thiamine hydrochloride | 32 mg |

II Methods

1. Handling of DNA

Cleavage with restriction endonucleases, ligation using T4 DNA ligase, phosphorylation of DNA, isolation of DNA from E. coli, separation of DNA by gel electrophoresis, and all other techniques belonging to the field of gene technology used in these applications were essentially performed as described by Maniatis et al., 1982.

2. Transformation of yeast

Methylotrophic yeast is transformed by the methods described previously (Roggenkamp et al., 1986).

The method using intact frozen cells is preferred (Klebe et al., 1983).

a) Transformed cells are identified by complementation of ura3 deficiency or by resistance to gentamycin.

Resistance against gentamycin G418 was checked by plating the cells on YEPD plates containing 25 ml solidified medium. After 6 hours of growth on the plates 1 ml aqueous solution containing 25 mg gentamycin 418 was applied onto each plate and the incubation continued for 2 to 3 days. Gentamycin G418 (Trade Mark Geneticin) was obtained from Gibco Ltd.

b) Segregation of mitotically stable transformants was performed by selecting transformants from the selective transformation plate and allowing them to grow in a liquid selective medium (YNB or YEPD with G418 at 1 mg/ml) for about 20 generations (two passages). After this growth period cells were inoculated into a non-selective medium (SMR or YEPD) and allowed to grow for another 40–60 generations (5–6 passages). The cells were then plated on a selective plate (YNB or YEPD with G418 at 1 mg/ml) and clones still expressing the selective marker were retained.

3. Isolation of yeast DNA

Total DNA from yeast was prepared as described in Struhl et al. (1979).

4. Analysis of yeast DNA

The structure of the DNA in yeast transformants was analysed by digestion with appropriate restriction endonucleases followed by agarose gel electrophoresis. DNA fragments were then transferred to nitrocellulose and hybridized with the appropriate radioactively labelled DNA probe (Southern 1975).

5. Immuno assays

Western Blot Analysis a) Amersham procedure

Proteins obtained from crude extracts or from gradient fractions were separated by SDS-polyacrylamide gel electrophoresis (Laemmli, 1970) using 12.5% separating, 5% stacking gels. The protein bands were transferred onto nitrocellulose essentially as described by Towbin et al. (1979).

The antigenic material was detected by reacting the blot with specific antibodies. The antigen-antibody complex was visualised by reacting the filter with biotinylated antibody RPN 1001 (Amersham Buchler GmbH and Co. Ltd., Braunschweig, FRG) in a 1:300 dilution followed by an incubation with peroxidase-streptavidin-complex RPN 1051 (Amersham). All steps of the experiment were performed according to the instructions of the manufacturer.

b) Alternatively, the filter was preincubated with 0.05% Tween (w/v) in PBS. Following incubation with the given monoclonal antibody, antibody binding was detected by successive incubation with biotinylated sheep anti-mouse IgG (RPN 1021, Amersham) in a 1:250 dilution containing 0.05% Tween 20, streptavidin-biotinylated horse radish peroxidase complex (RPN 1051, Amersham, dilution 1:400 in PBS containing 1% gelatin) and finally 30 µl. $H_2O_2$ and 10 ml HRP Colour Development reagent containing 4-chloro-1-naphthol (3 mg/ml methanol) in 50 ml PBS. Between incubations the filter was washed with PBS containing 0.05% Tween 20.

Quantification of produced monomeric antigens (S and preS) was achieved by comparison of samples of 0.01–0.3 µg of yeast-derived purified HBsAg (SmithKline Biologicals) to 3–5 different dilutions of crude protein extracts of Hansenula containing 2 to 20 µg total cell protein.

The protein concentration was determined using a BioRad protein assay kit (BioRad Munich, FRG).

EXAMPLES: PART A

Plasmids

EXAMPLE A.1

Construction of plasmids enabling expression of protein in *Hansenula polymorpha* a) Construction of a basic plasmid containing an *Hansenula polymorpha* autonomously replicating sequence (pME4).

The parental plasmid used to construct plasmids containing the S-gene under control of Hansenula promoters is pME4, which is already disclosed in the Ph.D thesis of M. Eckart, 1988. pME4 is a derivative of YIp5 (Struhl et al., 1979; Stinchcomb et al., 1980) obtained by the following modifications:

The *Hansenula polymorpha* autonomously replicating sequence HARS1 is cloned into the SalI site of YIp5 as disclosed in Roggenkamp et al. (1986) to result in pHARS. Plasmid pHARS was then reconstructed by deleting and reinserting the 440 base pair HARS1-SalI fragment into the PvuII site of the same vector. The SalI sticky ends of the fragment were made blunt ended prior to ligation by incubation with exonuclease VII followed by reaction with Klenow polymerase. This reconstruction resulted in a single SalI site in the tetracycline resistance gene of the pBR322 part of the plasmid. The intermediate plasmid thus obtained was again reconstructed in order to obtain a beta-lactamase gene lacking the original signal sequence wherein the signal sequence is replaced by the linker shown below; for details, see Eckart (1988):

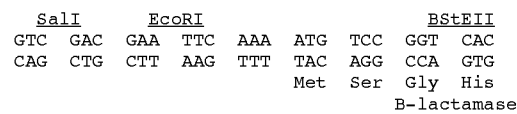

Figure 1:
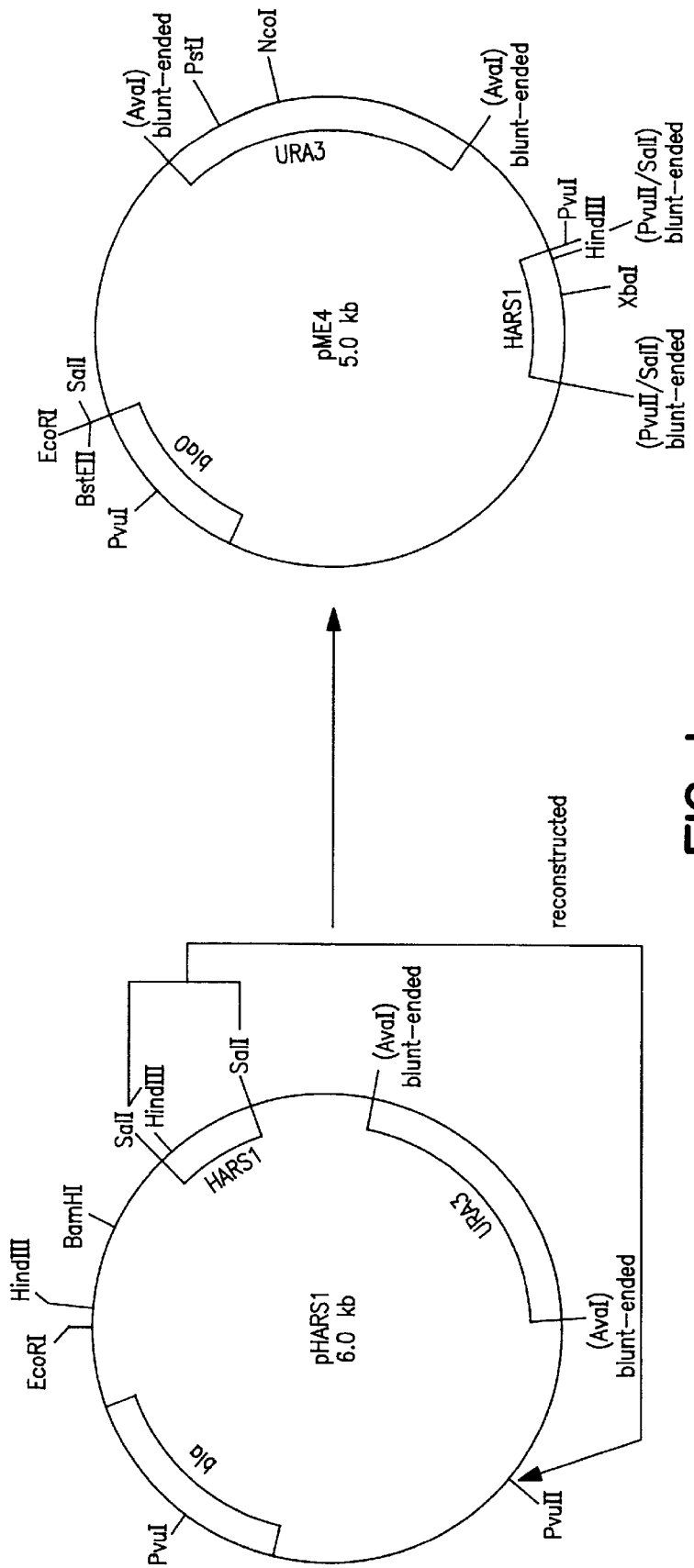
FIG. 1: Construction of plasmid pME4 from pHARS1. The HARS1 fragment has been transferred to the single PvuII site of former pHARS1, the sequences between the former position of HARS and the beta-lactamase gene as well as the 5' end of the beta-lactamase gene itself have been deleted.

This step yielded plasmid pME4 as shown in FIG. 1.

b) MOX and FMD promoter fragments.

Figure 2:
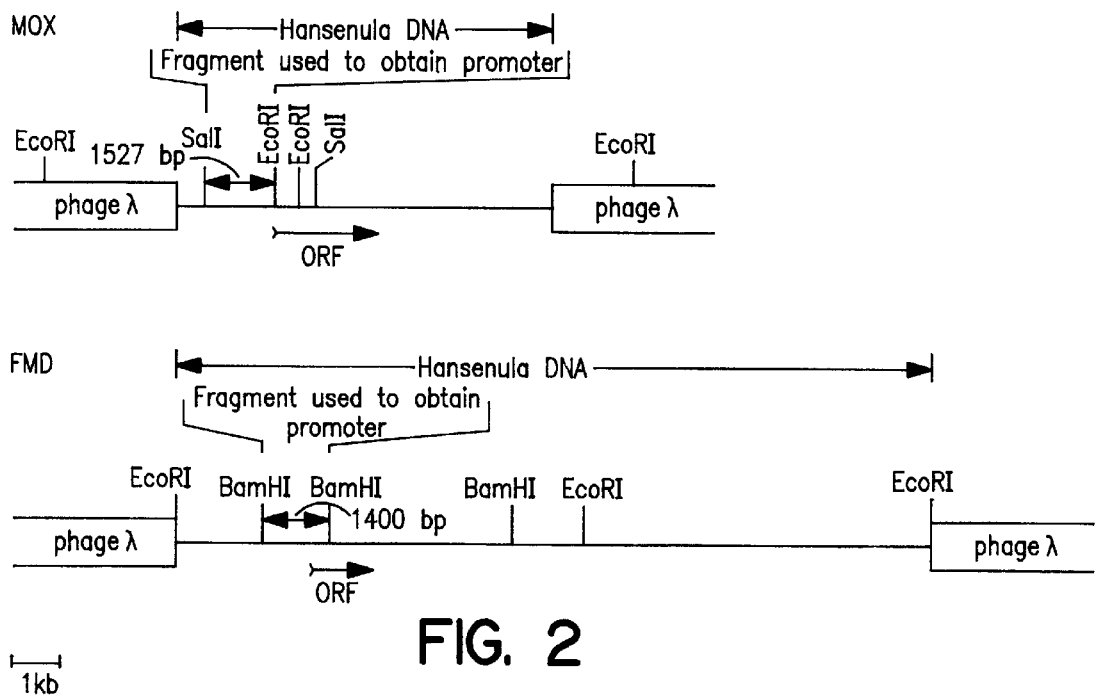
FIG. 2: Schematic representation of lambda-phages carrying genomic *Hansenula polymorpha* DNA fragments comprising: a) the MOX gene; b) the FMD gene.

The isolation of the MOX promoter from *H. polymorpha* is disclosed in Eckart, 1988. For the purposes of the present invention a genomic EcoRI-SalI fragment of 1525 bp containing the upstream control region of the MOX gene and the codons for the five first amino acids of the MOX protein was cloned into a pBR322 derivative. A schematic representation of the MOX-gene is given in FIG. 2. This intermediate plasmid was cleaved using EcoRI and treated with nuclease Bal31 and subsequently ligated with EcoRI linkers. Thus a series of promoter fragments having EcoRI 3' ends and SalI 5' ends were obtained by subsequent cleavage with restriction endonuclease SalI. The positions of the various deletion endpoints were established by DNA sequencing according to the method of Maxam and Gilbert, 1977. For the purpose of further experiments described in this application a plasmid designated pBR322-MP containing a deletion up to position minus 3 (when the first base of the MOX translation initiation codon is base plus 1) was used. The plasmid pBR322-MP is described in Eckart, 1988.

The isolation and characterisation of the FMD promoter is disclosed in European Patent Application 87 110 37 417.0. For the purposes of the present invention a 1.4 kb BamHI fragment encompassing about 1000 bp of the upstream promoter region was cloned into the BamHI site of pUC19. A clone was selected, in which the insert was orientated in a way to have the single EcoRI-site of pUC19 at the 3' end of the inserted fragment. A schematic representation of the genomic clone containing the FMD gene including its promoter is shown in FIG. 2B. A series of nuclease Bal31 deletions starting from the EcoRI site within then pUC19-linker was prepared in order to obtain plasmids containing the promoter without sequences of the structural gene. Following Bal31 treatment the DNA was ligated to EcoRI linkers, the DNA was cleaved with BamHI and the BamHI-EcoRI fragments were cloned into pBR322. A variety of deletions were obtained. Deletions to positions minus 5 and minus 9 from the first ATG were most efficient in later experiments. For the further experiments described in this application a plasmid carrying a promoter fragment containing the deletion to position -9 from the first ATG was used (plasmid pBR322-FMD-P-9). A schematic representation of the MOX- and FMD promoter fragments used for construction of further plasmids is shown below.

i) MOX promoter fragment (-3)

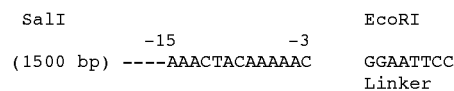

ii) FMD promoter fragment (-9)

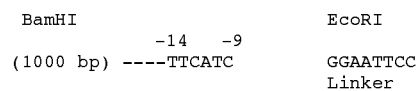

C) Terminator

The isolation of a transcription terminator from the MOX gene is disclosed in Eckart, 1988. A schematic representation of the 3' region of the MOX gene is shown below:

```
                        Arg Phe Stop
---------------------------------
                        AGA TTC TAA
SalI---------Asp718----------------EcoRV------NruI
<          1477 bp          > < 327bp >
                   < 284 bp      > <    368bp    >
```

The SalI-NruI fragment shown in the scheme above was subcloned into pBR322 between the SalI and NruI sites and this plasmid was then cleaved using restriction endonuclease Asp718 resulting in a linearisation of the plasmid due to a single Asp718 site within the MOX open reading frame, and subjected to Bal31 deletions.

Figure 3:
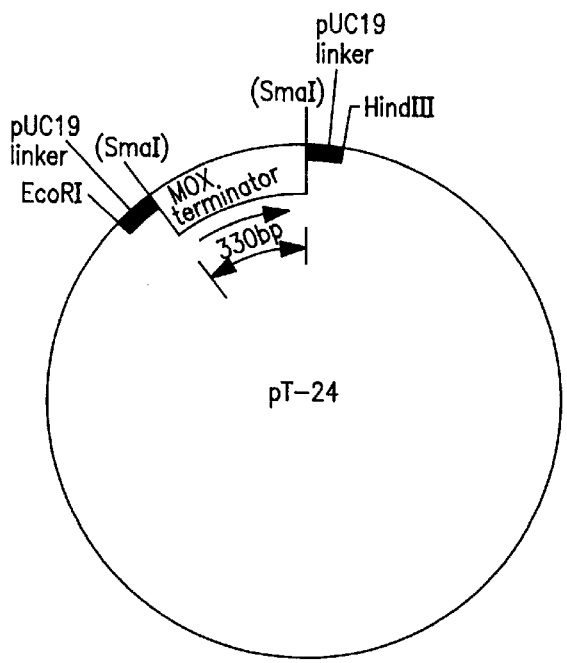
FIG. 3: Map of plasmid pT-24. This plasmid contains a DNA fragment encompassing the terminator of the MOX gene cloned into the SmaI-site of the pUC19 multiple purpose cloning site.

By DNA sequence analysis of the resulting fragments a terminator fragment of about 320 bp was identified (Eckart, 1988) which still functions as terminator. This blunt ended terminator fragment (GACATACC-315bp-EcoRV) was ligated into the SmaI site of pUC19. Orientation of the fragment was established by sequence analysis (Maxam and Gilbert, 1977). The resulting clone pT-24 is shown in FIG. 3. This clone was used to construct expression vectors as shown below.

d) Selective marker genes pME4 (described above, see FIG. 1) was cleaved with EcoRI and the sticky ends were filled in with Klenow polymerase. Plasmid pT-24 was digested with EcoRI and HindIII and the fragment comprising the pUC19 linker and the MOX terminator fragment isolated. The sticky ends of this fragment were made blunt ended by treatment with Klenow polymerase and the blunt ended fragment ligated with pME4. The resulting plasmid was called pP/T-24. The cloning sites derived from pUC19 were later on used for further cloning steps.

Plasmid pP/T-24 contains the *S. cerevisiae* URA3 gene as a selective marker. As a further selective marker a gene conferring resistance against chloramphenicol was introduced. This gene was isolated from vector pBR325 as a 1.7 kb AatII-ClaI fragment, subjected to a short Bal31 digestion for removal of about four base pairs on each side, and made blunt-ended using Klenow fill-in reaction. Subsequently the fragment was ligated with pP/T-24, which had been cleaved with NruI. The resulting plasmid showing chloramphenicol resistance was called pP/T-24-C.

EXAMPLE A.2

Construction of a plasmid containing the Hepatitis B surface antigen gene in functional combination with the *Hansenula polymorpha* terminator.

In order to obtain a functional unit comprising the Hepatitis B S-gene and a terminator efficient in *Hansenula polymorpha* the S-gene was introduced as an NcoI-EcoRI fragment of 683 bp into the BamHI site of the plasmid pP/T-24C provided by the pUC19 linker portion of said plasmid. The 683 bp fragment was obtained from pRIT12331 which is a conventional pUC9 based *E. coli* vector containing the 683 bp NcoI-EcoRI DNA fragment encoding the S-protein from NcoI at the ATG codon (CC <u>ATG</u>G) to EcoRI beyond the TAA stop codon (<u>TAA</u>CGAATTC). The surface antigen coding sequence was derived by conventional recombinant DNA techniques from pRIT10616 disclosed in EP-A-0278940 and in Harford et al., 1987. pRIT10616 contains the genome of a HBV virus of adw serotype cloned on pACYC184 and was deposited with the American Type Culture Collection under the terms of the Budapest Treaty on Jun. 2, 1982 under Accession Number ATCC39131.

The sticky ends of the S-gene fragment and of the BamHI cleaved pP/T-24C were made blunt ended by filling in prior to ligation. Ligation of the fragment in the proper orientation regenerates adjacent BamHI and NcoI sites on the construction immediately 5' to the S-gene coding region. The resulting plasmid is called pRB-S.

EXAMPLE A.3

Construction of plasmids containing a functional expression cassette comprising *Hansenula polymorpha* derived promoters, Hepatitis B surface antigen gene and *Hansenula polymorpha* terminator.

The pBR322 derivatives pBR322-MP and pBR322-FMD-P-9 containing the MOX or FMD promoters, respectively, were digested with EcoRI and the sticky ends were filled in using Klenow polymerase. The plasmids were then cleaved with SalI. The resulting fragment containing the MOX promoter comprises exclusively *Hansenula polymorpha* genomic DNA, whereas the fragment comprising the FMD promoter contains in addition 275 bp of pBR322 sequences (position bp 375 to bp 650 of pRB322 map).

Figure 4:
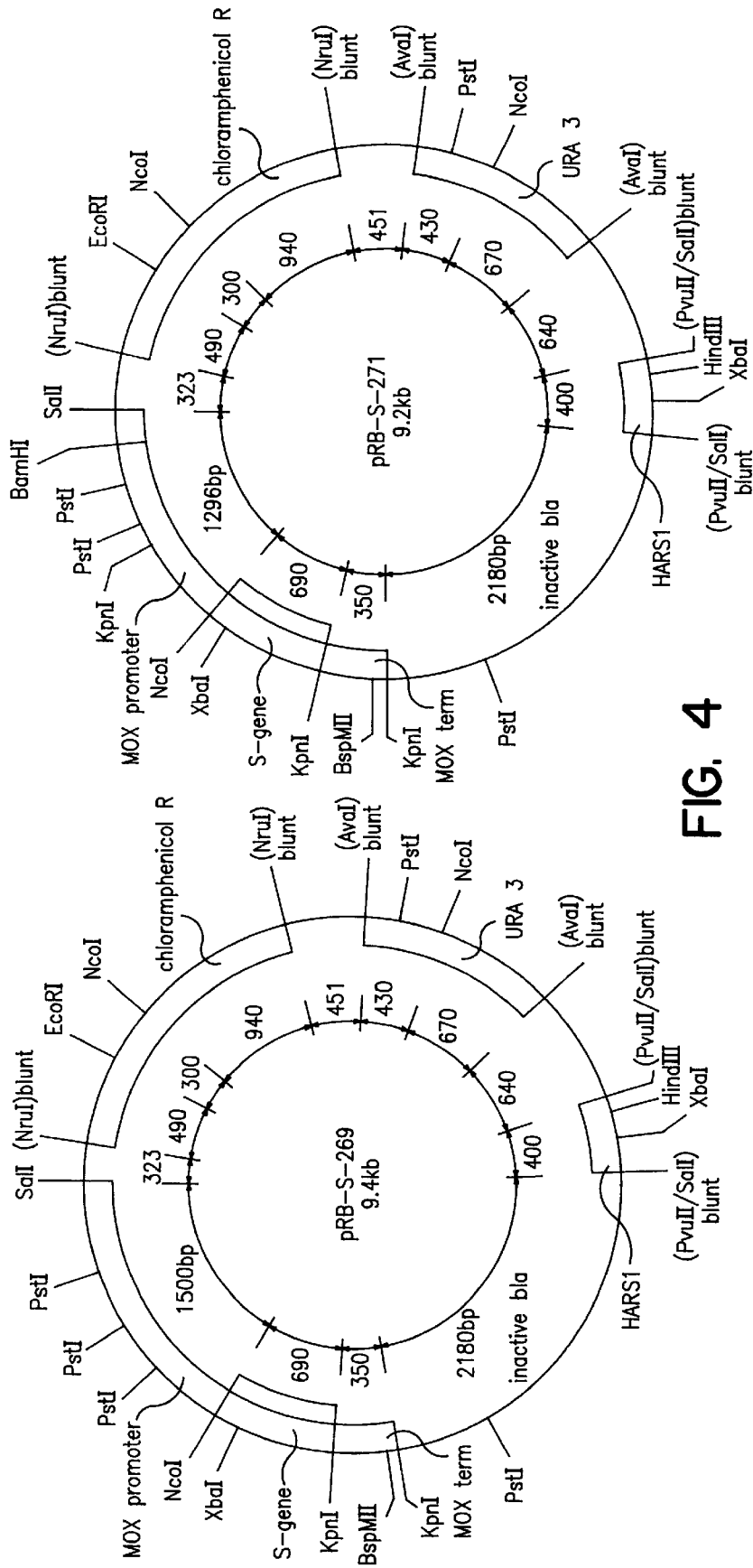
FIG. 4: Maps of plasmid pRB-S-269 and pRB-S-271 expressing the S-gene under control of the MOX- or FMD-promoter, respectively.

Plasmid pRB-S was cut at the regenerated BamHI site, the site was made blunt ended by filling-in with Klenow polymerase and subsequently the plasmid was digested with SalI. The promoter fragments having a SalI sticky end and a blunt end were ligated with the large SalI-blunt end fragment of pRB-S containing the S-gene coding region and the *Hansenula polymorpha* terminator. The resulting plasmids are called pRB-S-269 (MOX promoter) and pRB-S-271 (FMD promoter, minus 9 deletion) and contain the S-gene under control of the *Hansenula polymorpha* promoter and terminator as shown in FIG. 4. The sequence surrounding the fusion between promoters and S-gene is shown in the schematic representation below.

a) MOX—promoter fusion (pRB-S-269)

b) FMD—promoter (-9) fusion

Plasmids constructed identically to pRB-S-271 and pRB-S-269, but lacking the insertion of the 440 bp restriction fragment carrying the HARS1 sequences were called pRB-S-269I and pRB-S-271I. These plasmids were used to obtain integrants containing 1 to 3 copies of the expression cassette.

EXAMPLE A.4

Construction of integrative vectors containing the S-gene.

a) Construction of plasmid pBC containing *Hansenula polymorpha* autonomously replicating sequences and *H. polymorpha* URA3 gene.

Figure 5:
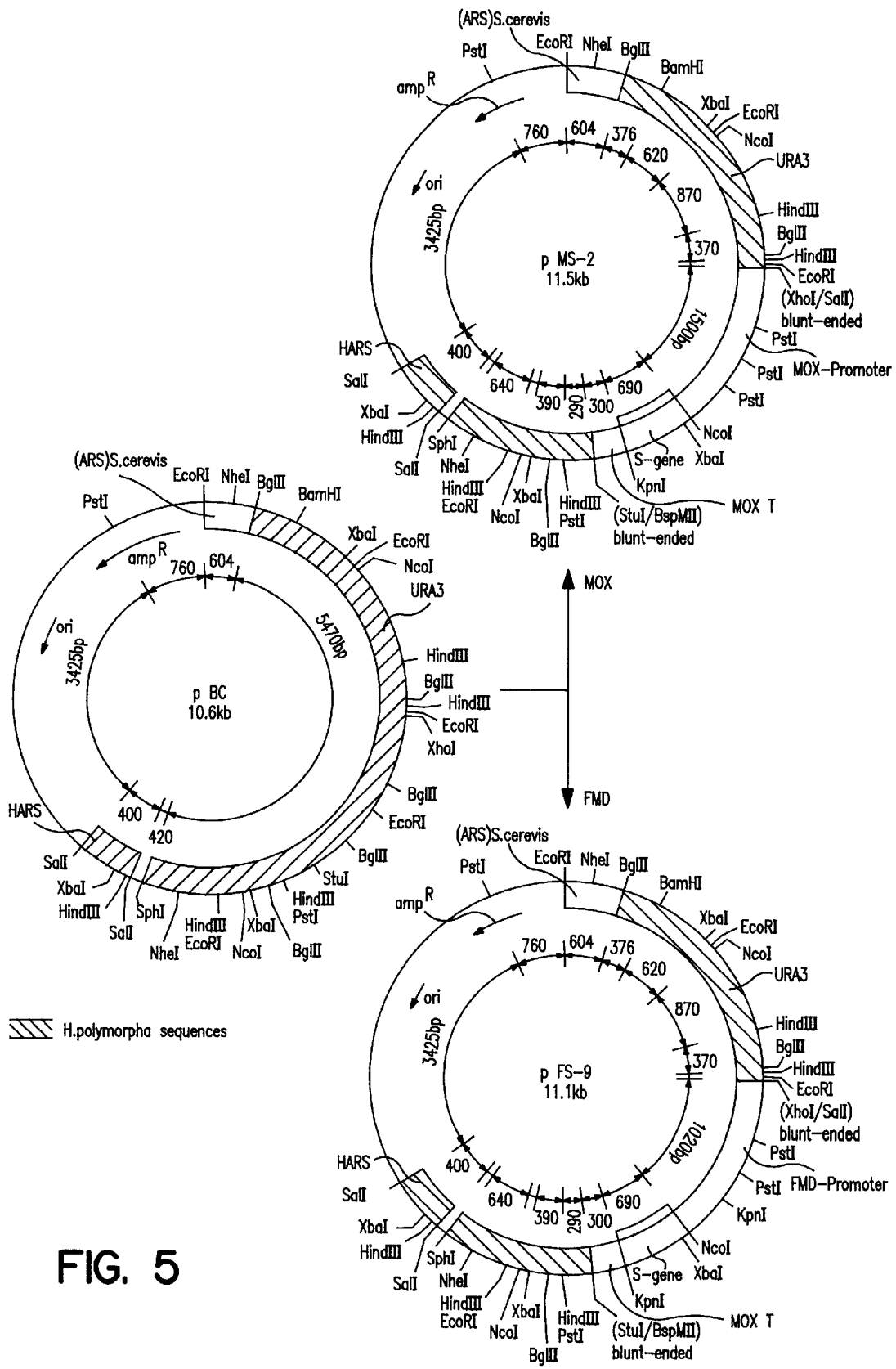

Plasmid pBC is derived from plasmid YRp7 (Tschumper and Carbon, 1980) containing the *Saccharomyces cerevisiae* ARS1 sequence. This autonomously replicating sequence was inactivated by insertion of a 5400 bp BglII-SphI fragment encompassing the *Hansenula polymorpha* URA3 gene. Furthermore the Hansenula autonomously replicating sequence 1 (HARS1) was cloned into the SalI site of the tetracycline resistance gene (FIG. 5).

b) Insertion of expression cassettes into plasmid pBC.

Plasmid pRB-S-269 was digested with BspMII and SalI.

The resulting fragment bearing the expression cassette comprising the MOX promoter, the Hepatitis B surface antigen encoding region and terminator was made blunt ended and ligated to plasmid pBC following cleavage with XhoI and StuI and filling in of the XhoI sticky ends. The resulting plasmid pMS-2 contains the S-gene expression cassette surrounded by flanking sequences of the *Hansenula polymorpha* URA3 gene fragment.

For integration of the S-gene expression cassette into the *Hansenula polymorpha* genome plasmid pMS2 was cleaved with NheI and the resulting fragment of 6.1 kb was used to transform the cells.

Vector pFS-9 was constructed in an analogous way except that the expression cassette was isolated from pRB-S-271 containing the FMD promoter.

A detailed description of the resulting plasmids is provided by way of FIG. 5.

EXAMPLE A.5
Construction of plasmids comprising the S-gene expression cassette and an additional selective marker gene.
a) Construction of the basic plasmid pHK2

For construction of plasmid pHK2 (FIG. 6; deposited under the terms of the Budapest Treaty with the DSM (DSM DEUTSCHE SAMMLUNG VON MIKROORGANISMEN UND ZELLKULTUREN GmbH) under Accession number 5328 on Apr. 27, 1989) the kanamycin resistance gene was isolated from transposon Tn5 (Grindley and Joyce, 1980). Unnecessary sequences were deleted by treatment of the structural gene with nuclease Bal31. The resulting fragment comprising the kanamycin structural gene including the kanamycin terminator was ligated with the *Saccharomyces cervisiae* ADH1 promoter (Hitzeman et al. 1981). Furthermore the HARS1 sequence was introduced as a 440 bp SalI fragment into the plasmid.
b) Construction of kanamycin resistant strains derived from pRB-S-269 and pRB-S-271.

The HindIII fragment from pHK encompassing the kanamycin resistance coding region (3.5 kb) was cloned into the HindIII site present in the HARS1-sequence of plasmids pRB-S-269 and pRB-S-271. The resulting plasmids are called pRB-S-322 and pRB-S-326 respectively and are shown in FIG. 7.

EXAMPLE A.6
Construction of a parental plasmid for expression of pre-S proteins.

Plasmid pP/T-24 (Example A.2) was reconstructed in order to obtain a plasmid pMox—P/T1 (FIG. 8) carrying a universal expression cassette comprising the MOX promoter, a multiple cloning site and the MOX terminator.

In order to insert a linker containing restriction sites for restriction endonucleases SalI, EcoRI, BglII and BamHI the pUC19 linker of plasmid pP/T-24 was partly replaced by synthetic DNA containing restriction sites for the above mentioned enzymes.

Plasmid pP/T-24 was cleaved with restriction endonucleases BamHI and SalI. These sites originate from the pUC19 linker (BamHI) and pME4 (SalI). The linker molecule containing restriction sites for SalI, EcoRI, BglII and BamHI was inserted. The resulting plasmid pT1 was digested with EcoRI and SalI and the MOX promoter was inserted as a 1.5 kb EcoRI-SalI fragment yielding plasmid pT2. The relevant areas of plasmid pT2 are shown below:

```
      SalI              EcoRI    BglII    BamHI
     -1500       -3
   ------//---AAAAAC   GGAATTC  AGATCT   GGATCC   AGCTT----
   <----------------                              ---------->
       MOX promoter                               Terminator
```

Furthermore plasmid pT2 contains the *Hansenula polymorpha* ARS and *Saccharomyces cervisiae* URA3 gene as in plasmid pRB-269 (FIG. 3).

The next construction step was the replacement of the *Saccharomyces cervisiae* URA3 gene by the URA3 gene derived from *Hansenula polymorpha*. A clone containing this gene was isolated as described below in example A.9. The URA3 gene was isolated as a 1.2 kb BamHI-BglII fragment. Whereas the BglII site is an original genomic site, the BamHI site was the result of ligating a Sau3A site with a BamHI site used to construct the genomic library. The sticky ends of this BamHI-BglII fragment were filed in by Klenow polymerase and inserted into the AvaI site of pBR322, which also had been filled in with Klenow polymerase. The AvaI site was regenerated by the ligation and the resulting plasmid was designated pURA3-P1.

Plasmid URA3-P1 was digested with NruI and BspMII. These sites originate from pBR322, positions bp 974 and bp 1664 of the conventional pBR322 map. Plasmid pT2 was subjected to a complete digestion with NruI (bp 974 of pBR322) and partial digestion with BspMII.

There are 2 BspMII sites in pT2: The first in pBR322 (bp 1664), the second is located in the MOX terminator. The NruI-BspMII fragment of pT2 (1800 bp) contains the URA3 gene of *Saccharomyces cerevisiae*. The NruI-BspMII fragment from URA3-P1 carrying the *Hansenula polymorpha* URA3 gene was cloned into pT2 replacing the *S. cerevisiae* URA3 gene located on the corresponding NruI-BspMII fragment. The resulting plasmid pT3 contains the MOX terminator, a linker, the MOX promoter and the *Hansenula polymorpha* URA3 gene following one another. Plasmid pT3 lacks however a functional β-lactamase gene as in parental plasmid pME4. To replace this defective β-lactamase gene by a functional gene pBR322 was digested with EcoRI, the sticky ends filled-in with Klenow polymerase and ligated to a 8 bp Asp718 linker followed by digestion with PvuI (position 3738 of the pBR322 map). The 633 bp Asp718-PvuI fragment thus obtained bears the original promoter and translation initiation codon of the β-lactamase gene.

Plasmid pT3 was subjected to cleavage by Asp718 (the Asp718 is located at the end of the MOX terminator) and to a partial digestion with PvuI. The Asp718-PvuI fragment obtained as described above was then inserted into the pretreated pT3 yielding the plasmid pMOX-P/T1.

Plasmid pMOX-P/T1 is shown in FIG. 8. This plasmid contains a functional beta-lactamase gene.

EXAMPLE A.7
Construction of plasmids expressing pre-S proteins.

The pre-S gene encoding the preS1-S2-S-protein (large protein) of Hepatitis B virus was obtained as a NcoI-HindIII fragment from pRIT12816. pRIT12816 is a conventional pBR322 based *E. coli* vector containing a 1185 bp NcoI-HindIII fragment encoding the preS1-S2-S-protein from NcoI at the ATG codon (CCATGG) to HindIII at 15 bp beyond the TAA stop codon (. . . AAGCTT). The preS1-S2-S-coding sequence fragment was derived by conventional cloning techniques from pRIT10616 disclosed in EP-A-0278940 and in Harford et al., 1987. A 861 bp fragment encoding the preS2-S sequence can also be recovered from this by conventional means. The NcoI-HindIII fragment was made blunt ended by filling-in with Klenow polymerase and cloned into the also made blunt ended EcoRI site of pMOX-P/T1. As a consequence of correct ligation the EcoRI site in front of the preS1 structural gene is regenerated by NcoI/EcoRI blunt ended ligation. The construction expressing the pre S-gene under control of the MOX promoter is colled pMPS-22. This is shown in FIG. 8.

The analogous construction containing the FMD promoter is called pMPS-21.

EXAMPLE A.8

Construction of a vector containing a preS expression cassette.

The SalI-Asp718 expression cassette from plasmid pMPS22 was made blunt ended by filling in and inserted between the filled in XhoI site and StuI sites of plasmid pBC described in Example A4a above. The resulting plasmid is called pMPS-9 and shown in FIG. 9.

EXAMPLE A.9

Cloning of the *Hansenula polymorpha* URA3 gene.

The URA3 gene of *Hansenula polymorpha* was cloned by complementation of the corresponding pyrF mutation of *E. coli* strain MB 1000.

Genomic DNA fragments ranging in size from 6 to 9 kbp were isolated via partial digestion with Sau3A, separation on a low melting agarose gel and isolation of the appropriate DNA fraction.

The purified fragments were ligated into the unique BamHI site of vector YRp7, containing an autonomous replicating sequence of *Hansenula polymorpha* inserted into the SalI site. The resulting ligation mixture was used to transform *E. coli* strain MB 1000 and transformants were selected on minimal plates without uracil. Transformants obtained were analysed and the plasmids were isolated. A sub-fragment as shown in FIG. 10 was isolated, which mediated the restoration of the URA$^+$ phenotype in *E. coli*, *Saccharomyces cerevisiae* and *Hansenula polymorpha* orotidine 5'-monophosphate decarboxylase mutants. The structure of the cloned DNA was shown to be identical to that of the genomic URA3 region by Southern blotting. A restriction map of the *Hansenula polymorpha* URA3 gene fragment is shown in FIG. 10.

Part B

Expression of Hepatitis B Surface Antigen (HBsAg) in *Hansenula polymorpha*

EXAMPLE B.1

Construction of *Hansenula polymorpha* strains containing the S-gene

*Hansenula polymorpha* RB 10 was transformed with the above described plasmids pRB-S-269, pRB-S-269-I, pRB-S-271, pRB-S-271-I. Several clones bearing automonously replicating plasmids (transformants) or integrated foreign DNA (integrants) were obtained.

These transformants/integrants were then tested for the expression of S-gene using immuno assays. Two test systems were used: Western blotting and AUSRIA or AUSZYME tests (Abbott). The production of HBsAg monomer was analysed by Western blotting using monoclonal RF6 antibodies. Abbott's AUSRIA or AUSZYME Kits were used according to the instructions of the manufacturer to estimate the amount of HBsAg particles produced in Hansenula. Transformants showing a stable and high expression level were selected and their DNA analysed by Southern blotting following electrophoretic separation.

a) Transformants

Several colonies bearing the freely replicating plasmid were obtained from *Hansenula polymorpha* transformed with plasmids pRB-S-269 and pRB-S-271. Southern analysis of the total DNA obtained from these transformants digested with different restriction endonucleases showed the expected restriction pattern.

b) Integrants

*Hansenula polymorpha* can be transformed with the integrative vectors pRB-S-269-I and pRB-S-271-I at a high frequency. Integrants grown on complete medium (YEPD) are mitotically stable. Alternatively, mitotically stable maintenance of a foreign DNA in Hansenula can also be obtained by the procedure described above, wherein an autonomously replicating vector, preferably a high copy number plasmid such as pRB-S-269 or pRB-S-271 integrates spontaneously into the genome. The resulting integrants also show high mitotic stability of the foreign DNA.

Both methods mentioned above were used to obtain strains efficiently expressing the S-gene in non-selective complete medium. 3 strains were retained; the strain having the identification number 352, which was transformed with pRB-S-271, wherein the S-gene is regulated by the FMD-promoter, and strains No. 415 and 416, which were transformed with pRB-S-269 containing a MOX regulated S-gene, were used for further experiments.

EXAMPLE B.2

Mitotic Stability of Foreign DNA in Integrants

The stability of the recombinant strains 352, 415 and 416 was tested by the following procedure: Strains were grown in non-selective SMR medium for 40 generations. Twelve independent colonies .were isolated from the cultures before and after the 40-generation period.

The structure of the foreign DNA and the copy number of the expression cassette were examined in the isolated clones by Southern blot analysis in combination with agarose gel electrophoresis of restriction fragments and Pulsed Field Gradient Gel Electrophoresis of total chromosomes. The latter technique allows the separation and analysis of yeast chromosomes (Schwartz and Cantor, 1984).

Pulsed Field Gel Electrophoresis

Cells from strains 415, 416 and 352 were subjected to gentle lysis in the sample wells of an 0.7% w/v agarose gel. The in situ liberated chromosomes were separated using an LKB-Pharmacia Pulsaphor Plus apparatus according to the instructions of LKB-Pharmacia. Following PFGE the DNA was transferred to nitrocellulose according to the procedure of Southern (1975). The blot was submitted to hybridisation using $^{32}$P-labelled probes specific either for the MOX and/or FMD gene or the URA3 gene of *Hansenula polymorpha*, the latter being known to be present as a single copy in the genome.

Comparison of the signals derived from possible multimeric integrants with those of single copy genes (intrinsic markers) allowed an estimation of the copy number of the relevant expression cassettes present inside the cell. The analysis of chromosomes by PFGE demonstrates that clone 415 has about 30 to 50 copies of the expression cassette, whereas clone 416 contains about 5–6 expression cassettes and clone 352 about 10 expression cassettes. The analysis showed that the foreign DNA is integrated into the Hansenula genome.

Southern Analysis

Strains 352, 415 and 416 were grown for 40 generations in SMR medium. Twelve independent colonies were isolated from each batch before and after the above mentioned growth period. DNA preparations from these sub-clones were then subjected to Southern analysis after cleavage with various restriction enzymes and using $^{32}$P-labelled DNA-probes. Analysis of the restriction patterns showed that the expression cassettes were intact and that the introduced DNA was genetically stable. The analysis further revealed that the genome of strain 415 contains long repeats with several copies of the plasmid. The plasmid is deduced to be arranged in this repeat in a head to tail manner.

EXAMPLE B.3

Expression studies

Recombinant strains were routinely analysed for the presence of HBsAg by Western Blotting and AUSRIA/AUSZYME tests.

a) Growth of Cultures and Western blotting

Strains 352, 415 and 416 were grown in 1l flasks in 200 ml SMR-glycerol medium at 37° C. with vigorous aeration. At the beginning of the stationary phase, which is characterised by the depletion of glycerol, 50 ml/l of a five fold concentrated SMR medium lacking glycerol was added together with methanol to a final concentration of 10 g/l. Samples of 10 ml volume were taken from the culture prior to addition of methanol and at 24 hours following addition of methanol. For the purpose of comparison the same strains were grown also in SMR medium containing 30 g/l glucose (repression of promoters). The cells were harvested in the late log-phase.

From the harvested cells crude protein extracts were prepared by suspending a cell pellet corresponding to about 0.1 g dry weight in 5 ml of PE buffer (0.5 M NaCl, 0.1% Triton X-100, 10 mM phosphate buffer pH 7.5, 2 mM PMSF). Approximately an equal volume of glass beads of 0.45 mm diameter was added until the mixture because almost solid. The mixture was subjected to vigorous shaking for 4 minutes at 4° C. using a Braun MSK homogenisation (B. Braun and Diessel Biotech GmbH, Melsungen, FRG). Subsequently, 4 ml of PE buffer was added and the homogenate was mixed and centrifuged 5 minutes, at 4° C., 40,000×g. Aliquots of 5 to 25 μg of the supernatant were subjected to SDS-polyacrylamide gel electrophoresis, using purified HBsAg (0.05 to 0.5 μg) as a control. The presence of antigenic material was demonstrated by transferring the protein onto nitrocellulose according to the procedure of Towbin (1979) and detection with the monoclonal antibody RF6 as described in Method 5a above. The Western blots allow an estimation of the amount of antigen produced in clones 352, 415 and 416, by reference to the known amounts of pure yeast-derived HBsAg.

The results are summarized in Table 1. In methanol induced flask-cultures (SMR medium) with a cell density of about 5 g dry weight/l the S-protein constitutes about 2 to 5% of the total extracted protein of transformed strains.

The comparison of expression in cells grown under conditions of induction (methanol), derepression (glycerol) and repression (glucose) demonstrates a very stringent control of the MOX and FMD promoters. Expression is completely blocked in glucose grown cells. In glycerol, synthesis of HBsAg is about 30% of the level obtained in induced cells.

b) Antigenicity of HBsAg expressed in *Hansenula polymorpha*.

The antigenicity of the material contained in crude extracts was measured using an Abbott AUSZYME test based on monoclonal antibodies. The results were expressed as arbitrary units (absorbance at 492 nm per 0.1 μg protein). Dilution of crude extracts and the reaction were both performed in 150 MM NaCl, 25 mM phosphate buffer pH 7.4, 0.01% BSA, 0.01% Tween 20. The reactivity with the AUSZYME test indicates the presence of conformational epitopes characteristic for sub-viral particles.

TABLE 1

HBsAg production in strains expression S-gene

| Strain | Promoter | Carbon Source | HBsAg estimated by Western blotting mg/100 mg protein | HBsAg estimated by AUSZYME assay arbitrary $A_{492}$ units 0.1 μg protein |
|---|---|---|---|---|
| 352 | FMD | Glucose | No signal | 0.3 |
|  |  | Glycerol | 0.8–1.2 | 10.0 |
|  |  | Methanol | 2.5–3.0 | 25.0 |
| 415 | MOX | Glucose | No signal | 0.1 |
|  |  | Glycerol | 1.0–1.5 | 12.0 |
|  |  | Methanol | 4.0–5.0 | 45.0 |
| 416 | MOX | Glucose | No signal | No signal |
|  |  | Glycerol | 0.5–0.8 | 5.0 |
|  |  | Methanol | 2.0–3.0 | 22.0 | c) Density gradient centrifugation of crude extracts of *H. polymorpha*

The crude extracts obtained according to the procedure described above were subjected to density gradient centrifugation either using CsCl or sucrose gradients. Sucrose equilibrium sedimentation gradient centrifugation was performed by applying 100 to 200 μg (200 μl) of the crude protein extract on top of a 20 to 50% sucrose gradient in 50 mM NaCl, 2 mM EDTA, 25 mM NaPO$_4$, pH 7.2. Tubes having a volume of 5 ml were centrifuged for 18 hours at 40,000 rpm in a Beckman SW 50.1 rotor.

Cesium chloride gradient centrifugation was performed by diluting 1 volume of the crude protein extract with 1 volume of 3 M CsCl in 25 mM phosphate buffer pH 7.4 Centrifugation was performed at 4° C., 40,000 rpm in a Beckman 50 Ti rotor for 40 hours.

The gradients were subjected to fractionation and the various fractions tested using RF6 antibodies in Western blotting or using AUSRIA and/or AUSZYME assays. It could be shown that a peak of HBsAg material with a density of about 1.16 to 1.19 g/ml is formed in a CsCl density gradient. The material present in this peak reacts very well not only with RF6 antibodies in Western blots but also with the AUSRIA and AUSZYME assays. This density as well as reactivity in AUSRIA/AUSZYME tests indicate the presence of conformational epitopes characteristic for particles. Moreover, in a further experiment the density of this material was compared to sub-viral particles isolated from human serum. It could be shown that both materials are found at a comparable density by isopycnic centrifugation in CsCl solutions.

Sucrose gradient centrifugation of crude extracts gave peak fractions, which reacted with AUSRIA and AUSZYME and which constituted at least 80% of the HBsAg as shown by analyses of gradient fractions in parallel with AUSRIA/ AUSZYME and Western blotting. The residual 20% of the material is found mainly in the top and bottom fractions of the gradient and react only in Western blot analysis, indicating that this material constitutes the monomeric form of the protein. Analysis of peak fractions obtained from CsCl gradients also revealed that at least 80% of the material forms particles.

The Hansenula derived particles are resistant to proteolysis. Incubation of crude protein extracts containing particles for several hours at various temperatures reveals only a very minor degradation as shown by testing the AUSZYME values and analysing the intactness of the polypeptide by denaturating SDS-PAGE followed by western blot. The material was further analysed by electron microscopy. The electron microscopy pictures clearly show particles with a diameter of about 22 nm.

The above described results were obtained for all 3 strains (352, 415 and 416).

Part C

Expression of preS1-S2-S protein in *Hansenula polymorpha*

EXAMPLE C.1

Construction of *Hansenula polymorpha* strains containing the preS1-S2-S gene

*Hansenula polymorpha* RB 10 was transformed with the 5570 bp PvuI-Asp718 fragment derived from pMPS-22, encompassing the URA3 gene and preS1 gene under control of the MOX promoter (see FIG. 8). Furthermore, the corresponding fragment carrying the preS1 gene under control of the FMD promoter (−9 deletion) was obtained from plasmid pMPS-21. The integrants resulting from these transformations were shown to contain 1 to 2 expression cassettes by Southern analysis. Integrants containing the preS1 gene under control of MOX promoter are referred to as preS-AM; integrants containing the preS gene under control of FMD promoter are referred to as preS-AF.

Integrants containing several expression cassettes were obtained by transforming *Hansenula polymorpha* with autonomously replicating plasmids pMPS22 and pMPS21 bearing the HARS sequence. Integrants were formed by spontaneous integration of these plasmids as described in "Materials and Methods", item 2b. These types of transformants were given the general designation preS-BM (MOX promoter) and preS-BF (FMD-promoter).

Strains preS-AM-405, preS-BM-402, preS-BM-403 and preS-BM-454 wherein expression of the preS1-gene is regulated by the MOX promoter were retained for further analysis.

2. Mitotic stability

Mitotic stability of the foreign DNA present in the four strains identified in Example C.1 above was tested by Southern analysis of 12 independent subclones isolated before and after a 40 generations growth period as described in PART B. The analysis confirmed the genetic stability of the integrated vectors (see also an example in PART D.3).

3. Expression of preS protein in *Hansenula polymorpha*

Strains preS-BM-402, preS-BM-403, preS-AM-405 and preS-BM-454 were grown on SMR medium containing glycerol followed by induction of the cells with methanol (10 g/l) extractly as described in Part B. Cells were harvested 25 hours following addition of methanol and crude extracts were prepared as described in Part B.

a) 12 µg amounts of crude extracts of strains preS-BM-402, preS-AM-405, and preS-BM-454 were analysed by polyacrylamide SDS-gel electrophoresis followed by Western blotting using a mixture of monoclonal antibodies (S1.1, S2.2 and S2.5) as described in "Methods 5 (a)". Both types of strains showed an antigenic double band at 38/39 kD and a further band at 45 kD.

Strain preS-AM-405 showed a lower content of the 45 kD species relative to the 39 kD materials than did strain preS-BM-402; strain preS-BM-454 showed the highest relative content of the 45 kD species.

The electrophoretic pattern of preS-protein from the above strains was compared with antigen derived from human serum particles. Both human and yeast preparations show a band at about 38/39 kD when compared on Western blots.

b) A variation in the expression level for different strains was also seen. These differences were presumably due to variations in copy number of the expression cassette between the strains. The preS-antigen was estimated by Western blotting to constitute 0.1 to 1.5% of the total cell protein in different preS-A and preS-B strains as given in Table 2.

Crude extracts were also tested with the AUSZYME assay for the presence of particles. The results as shown in Table 2 demonstrate a very low reactivity expressed as $A_{492}$ units per 0.1 µg protein.

TABLE 2

| | Expression of preS in *H. polymorpha* | |
|---|---|---|
| Clone | Estimated PreS protein by Western blotting mg preS1/100 mg | AUSZYME $A_{492}$ units per 0.1 µg protein |
| preS-AM-405 | 0.1–0.2 | 0.01 |
| preS-BM-402 | 0.3–0.5 | 0.02 |
| preS-BM-403 | 0.4–0.6 | 0.02 |
| preS-BM-454 | 1.2–1.5 | 0.1–0.2 | c) Glycosylation: Strain preS-BM-454 characterised by high production of pres protein (about 1.5% of total cell protein) and a pronounced 45 kD band was chosen for further studies on glycosylation. PreS protein from preS-BM-454 was analysed by incubating the crude protein extracts with EndoH endoglycosidase. The following data clearly show that the 45 kD species is a glycosylated form of pres protein.

Upon incubation of 45 µg crude protein for 0.5, 1.0 and 24 hours with 0.5 mU EndoH endoglycosidase according to the instructions of the manufacturer (Boehringer Mannheim, FRG), the 45 kD band shifted to the apparent molecular weight of 42 kD. This shift indicates that the 45 kD species is a N-glycosylated form of preS protein, bearing one 'core' group of about 3000 D.

Tunicamycin, known to be a potent inhibitor of N-glycosylation, was also used to study the glycosylation of preS protein in *Hansenula polymorpha*. Strain preS-BM-454 was grown to a density of $A_{600}=10.0$ in YNB medium containing glucose (10 g/l). 10 ml of this culture was inoculated into 100 ml of YNB containing 10 g/l methanol and 50 μg/ml tunicamycin. The pH value of the medium was kept constant at 7.2 to 7.5. A control experiment was conducted without use of tunicamycin. The cells were harvested 10, 15 and 30 hours following inoculation of the medium containing tunicamycin.

Crude protein extracts were analysed by Western blotting. The studies demonstrated that in the cells grown in the presence of tunicamycin a single band at 42 kD and a double band at 38/39 kD are visible. In the control experiment the 42 kD band was replaced by a 45 kD band. Similar results were obtained with extracts from strains preS-BM-402, preS-BM-403 and preS-AM-405, which however produce much lower amounts of the 45 kD protein species (not more than 5 to 10% of total pre-S-protein synthesised). The results suggest that the 42 kD band represents an O-glycosylated form of preS-protein.

d) Density gradient centrifugation

Crude extracts from strain preS-AM-405 and strains preS-BM-402, preS-BM-403, preS-BM-454 were subjected to analysis by sucrose and CsCl gradient centrifugations. The conditions were described in Part B 3(c). The gradient fractions were tested by Western blotting and by AUSZYME tests.

The analysis revealed that in contrast to strains expressing S antigen (PART B) or both preS1 and S antigens (PART D), the preS-strains do not efficiently form sub-viral particles. Neither isopycnic CsCl nor sucrose gradient centrifugation revealed formation of a band of the required density. This was also confirmed by the fact that the HBsAg-related material from gradient fractions and crude extracts reacted poorly with the AUSRIA or AUSZYME tests.

PART D

Formation of composite particles containing both preS and S antigens

EXAMPLE D.1

Construction of strains

Several strains were constructed which are characterised by different ratios of preS1 to S expression and different total expression levels.

These differences were achieved by variation of the copy number of the expression cassettes per genome. Additional variability was obtained by placing the genes under the control of different Hansenula promoters.

Three basic types of recombinant strains were obtained as follows:

a) Strains containing one copy of the preS1 gene and one copy of the S gene (A-strains)

The 6.6 kb NheI DNA fragment containing the preS1 cassette and the URA3 gene was isolated from plasmid pMPS9 (FIG. 9). A NheI DNA fragment containing the S gene was isolated form plasmid pMPS2 (FIG. 5). The fragments were ligated using T4 DNA ligase and joined fragments consisting of one copy of each of the genes were isolated from agarose gels. These fragments were used to transform *Hansenula polymorpha* strain RB10 to uracil independence.

The resulting transformants were analysed by Southern blotting and clones containing one integrated copy of each cassette were selected. Strain preS/S-A-293 was retained for further analysis.

b) Strains containing one preS expression cassette and several S expression cassettes (B-strains)

*Hansenula polymorpha* was transformed with the 5570 bp Asp718-PvuI fragment from pMPS-22 containing the preS1 expression cassette. Transformants bearing one integrated copy of the cassette were selected. The strain retained was preS-AM-405 described in part C.1 above.

Strain preS-AM-405 was then transformed with autonomously replicating plasmids pRB-S-326 (FMD-promoter) or pRB-S-322 (MOX-promoter) (FIG. 7) containing the S gene under control of the respective promoters. Both plasmids in addition bear a gene encoding resistance against gentamycin G418 as a selective marker. The Kan gene is under the control of the *Saccharomyces cerevisiae* ADH1 promoter (FIG. 7) as described above. Transformation yielded several strains containing always one integrated copy of the preS1 cassette and multiple integrated copies (30 to 100) of the S gene containing cassette as shown by Southern blot and PFGE analyses.

Strains preS/S-B-431, preS/S-B-432 and preS/S-B-433 were retained for further analysis. Strain preS/S-B-431 carries a MOX—promoter controlled S-gene, whereas preS/S-B-432 and preS/S-B-433 contain expression cassettes comprising the FMD promoter.

c) Strains containing several expression cassettes of both the S and pres genes (C-strains)

*Hansenula polymorpha* was transformed with the autonomously replicating plasmid pMPS-22 containing the pre-S1 gene (FIG. 8). Transformation yielded several strains containing variable numbers of expression cassettes integrated into the genome. Isolates containing 2 to 20 preS1 expression cassettes were identified by Southern blotting. Those strains were described in Part C as preS-BM-402, preS-BM-403 and preS-BM-454 and express different amounts of preS antigen. These pres strains were then again transformed with autonomously replicating plasmids pRB-S-322 (MOX-promoter) and pRB-S-326 (FMD-promoter), which bear the S-gene (FIG. 7). Resistance against G418 was used as a transformation marker. Selection for stable integrants yielded several clones for each transformation some of which were further analysed. Strains retained for further analysis were preS/S-C-452, preS/S-C-465 derived from strain preS-BM-402, strain preS/S-C-466 derived from strain preS-BM-403, strain preS/S-C-448-C4 derived from strain preS-BM-454 wherein the S-gene expression cassettes comprise the FMD promoter. Table 3 provides detailed information about the origin and designation of the above described strains.

TABLE 3

Characteristics of strains expressing both preS and S-protein

| Strain | Estimated Number of preS cassettes | Estimated number of S-cassettes | Total expression of preS/S (Western) mg/100 mg | Reactivity with AUSZYME arbitrary $A_{492}$ units* | PreS to S ratio estimated from Immunoblotting |
|---|---|---|---|---|---|
| preS/S-A-293 | 1 | 1 | ca. 0.3–0.4 | 5.0 | ca: 1:1 |
| preS/S-B-431 | 1 | ca.10 | 1.5–2.0 | 10–15 | ca: 1:15 |
| preS/S-B-432 | 1 | ca.10–15 | 2.5–3.0 | 10–20 | ca: 1:15 |
| preS/S-B-433 | 1 | ca.20 | 2.0–2.5 | 10–15 | ca: 1:20 |
| preS/S-C-452 | several | >30–50 | 3.0–4.0 | 20–30 | ca: 1:8 |
| preS/S-C-453 | several | >30–60 | 3.5–4.5 | 15–25 | ca: 1:10 |
| preS/S-C-465 | several | >30–50 | 3.5–4.5 | 25–35 | ca: 1:5 |
| preS/S-C-466 | several | >50–80 | 3.5–4.5 | 25–35 | ca: 1:8 |
| preS/S-C-448-C4 | >20–30 | >10–20 | 3.0–3.5 | 10–20 | ca: 5:3 |

*Numbers represent the lowest and highest values determined for a given strain.

EXAMPLE D.2

Expression of preS and S-proteins in *H. polymorpha*

Expression of preS and S-proteins in different transformant strains of *H. polymorpha* was tested by immunoblotting as described above in Materials and Methods 5a and by the AUSZYME assay. A summary of the results and the properties of the various strains tested is given in Table 3.

Strains expressing both the preS and S-proteins were grown and induced as described in part B item 3 except that 30 ml culture volumes were used. Crude cell extracts were prepared as described above and subjected to SDS-polyacrylamide gel electrophoreses followed by Western blotting using RF6 or a mixing of S1.1 and S2.1 monoclonal antibodies for detection. 12 to 15 µg amounts of crude extracts from methanol induced cells of strains preS/S-A-293, preS/S-B-431, preS/S-B-432, preS/S-B-433, preS/S-C-453, preS/S-C-465, preS/S-C-466 and preS/S-C-448-C4 were immunoblotted using monoclonal RF6 for detection. This analysis demonstrates that a spectrum of strains can be obtained which express different ratios of pres to S-protein. From these and other immunoblots the ratio of preS to S-protein in strain preS/S-B-431 was estimated to be about 1:15, in strain preS/S-C-452 to be about 1:8 and in strain preS/S-448-C4 to be about 5:3. The strains were found to differ also in their level of productivity both by immunoblotting and by AUSZYME assay as shown in Table 3. Cell extracts from these strains were also immunoblotted using monoclonal S1.1 for detection. In most strains the preS protein is detected as the doublet protein band at 38–39 kD with lesser amounts of the 45 kD band (which is estimated to comprise only about 5% of the total preS-protein detected). In contrast strain preS/S-C-448-C4 expresses approximately equivalent amounts of the 38–39 kD and 45 kD species.

EXAMPLE D.3

Stability of the foreign DNA

The stability of the foreign DNA in the above described preS/S transformants and integrants was analysed as described in part B. The studies indicate a very good mitotic stability of the recombinant clones. Southern analysis of 12 independent colonies isolated before and following a 40-generation fermentation of strains preS/S-453 and preS/S-431 demonstrated that in all cases the same restriction fragment pattern was visible. The preS/S strains listed in Table 3 were also analysed by Pulsed Field Gradient Electrophoresis. The separated chromosomes were blotted onto nitrocellulose membranes and then hybridised with different radioactive DNA probes. The procedure allows estimation of the number of copies of the S-expression cassette and proved conclusively that these preS/S strains are integrants. The results of these experiments are summarised in Table 3 above.

EXAMPLE D.4

Isolation and characterisation of composite particles a) Partial purification of composite particles from *Hansenula polymorpha*.

A fermenter culture of *Hansenula polymorpha* strain preS/S-B-431 was grown in S-medium described above in Materials, 5d and the cells recovered by centrifugation after 78 hours induction with methanol. The cell pellet was resuspended at a concentration of about 120 g dry cell weight per liter in buffer containing 0.5% (w/v) Tween 20, 2 mM EDTA, 4 mM PMSF, 5% (v/v) isopropanol and 50 mM sodium phosphate buffer pH 9.0. Cells were broken in a bead mill (Dynomill Type KDL, Bachofen AG, Basel, Switzerland) containing 0.45–0.7 mm diameter glass beads using 4 passages at a flow rate of 6 liters per hour and a residence time of 7 minutes in the chamber.

The cell extract was clarified by centrifugation for 45 minutes at 16000 g at 4° C. and the supernatant recovered.

1% (w/v) colloidal silica (Aerosil 380, Degussa, Frankfurt, FRG) was then added to the supernatant with stirring and the mixture was stirred overnight at 4° C. to permit adsorption of HBSAg. The silica was recovered by centrifugation for 30 minutes at 4000 g at 4° C. and washed twice with 0.9% (w/v) NaCl by resuspension of the pellet and recentrifugation. HBsAg adsorbed to the silica was desorbed by resuspension of the washed pellet in 10 mM sodium pyrophosphate pH 9.5 and incubation for 3 hours at 37° C. with constant stirring. The volume of sodium pyrophosphate buffer added was about one eighth to one tenth of the initial clarified cell extract volume. The solution was then centrifuged at 17,000 g for 60 minutes at 4° C. and the supernatant recovered.

The supernatant was made 1.5 M with CsCl and the mixture centrifuged to isopycnic equilibrium for 70 hours at 45000 rpm in a 50.2 Ti rotor (Spinco Division, Beckman Instruments, Palo Alto, USA). The resulting CsCl gradients was fractionated and fractions tested for the presence of HBsAg using an Elisa kit (Enzygnost, Behring-Werke AG, Marburg, FRG) as described by the manufacturer. Peak fractions were pooled and dialysed against 10 mM sodium/ potassium phosphate, 0.15 M NaCl pH 6.8. Assays made on this material and the crude cell extract showed that 48% of total AUSTRIA reactive material, less than 3% of total proteins, less than 0.2% of total sugars and less than 2% of total lipids were recovered in this procedure.

A cell pellet of *Hansenula polymorpha* strain preS/S-C-452 was also extracted by exactly the same procedure with similar results.

Samples of the partially purified HBsAg preparations from the preS/S-B-431 and preS/S-C-452 strains were examined by gel electrophoresis and immunoblotting using monoclonals HBS1 and S1.1 for detection of HBsAg related proteins as described in Part D.4 below.

Immunoblotting with monoclonal HBS1 showed the presence of a reactive band at 24 kD and a further band at about 38/39 kD in both preparation. Immunoblotting with monoclonal S1.1 detected only the preS1-protein related band at 38/39 kD in both preparations.

This shows that both the preS1-protein and S-protein species copurify through colloidal silica adsorption and isopycnic CsCl density gradient centrifugation.

b) CsCl density gradient centrifugation of composite particles.

A fermenter culture of *H. polymorpha* strain preS/S-B-431 was grown in S-medium (Materials, 5d) and harvested after 73 hours induction with methanol. The cell pellet was recovered by centrifugation and resuspended and a cell extract prepared by passage through a French Press as described below. Cellular debris was removed from the crude lysate by centrifugation for 30 minutes at 17000 g. Crude cell extracts were then centrifuged to equilibrium at 245,000 g in 1.5 M CsCl, phosphate buffered saline pH 7.5. Gradients were fractionated and each fraction analysed for antigenicity using ELISA tests specific for HBsAg (Enzygnost:Behringwerke AG, Marburg, FRG) and for preS1-protein. The Enzygnost tests measures only assembled HBsAg particles, not protein monomers. The preS1-protein specific Elisa test employs murine monoclonal antibody S1.1 for antigen capture and detection and is described below in Part D.5.

A peak of HBsAg activity was observed at a density of 1.18–1.19 g/cm$^3$ in the CsCl gradient. A major peak of preS1-protein activity was observed at this same density together with a minor peak at a density of 1.26 g/cm$^3$.

The gradient fractions were also analysed for the presence of preS1-protein S-protein by immunoblotting. After sodium dodecylsufate polyacrylamide gel electrophoresis according to Laemmli (1970) and blotting to nitrocellulose according to Towbin et. al. (1979), the nitrocellulose sheet was incubated with a rabbit polyclonal serum raised against serum derived HBsAg. Detection of antibody binding was by the alkaline phosphatase method.

A major protein band at 24 kD corresponding to the S protein and a double band at 38/39 kD were observed. The maximum activity in the immunoblotting for all three protein species was in CsCl gradient fractions with a density of 1.18–1.19 g/cm$^3$ which corresponds to the peak of HBsAg activity measured in the Enzygnost test. This indicates that the majority of HBV surface antigen proteins in the crude extract are present in a lipoproteic structure with a density characteristic of HBsAg.

A further nitrocellulose sheet was incubated with murine monoclonal antibody S1.1. This antibody detected only the protein bands at 38/39 kD in fractions corresponding to a CsCl density of 1.18–1.19 g/cm$^3$. The crude cell extracts were also subjected to rate-zonal centrifugation on a sucrose gradient. Crude cell extracts were loaded on 5–20% (w/v) sucrose gradients made up in 50 mM Tris-HCl buffer pH 8.1 and centrifuged at 288,000 g for 200 minutes. Gradients were fractionated and the fractions analysed for the presence of HBsAg by the Enzygnost Elisa test and for the presence of preS1-protein containing HBsAg by capture of antigen with the HBsAg specific antibodies from the Enzygnost test and detection with preS1-protein specific Mab S1.1. The Enzynost assay showed a peak of HBSAg activity sedimenting through the gradient.

The Mab.1.1 Elisa showed the same peak as the Enzygnost assay but with a shoulder of activity extending into higher sucrose densities. This shoulder of material with a higher sedimentation coefficient is eliminated when crude extracts from *Hansenula polymorpha* strain preS/S-B-431 were partially purified by adsorption/desorption on colloidal silica and centrifugation in a CsCl gradient before analysis by sucrose density gradient centrifugation. These results show that both HBsAg and preS1-protein cosediment in CsCl density gradients with a density characteristic of lipoproteic particles.

c) Antigenicity of composite HBsAq particles expressed in *H. polymorpha*

HBV surface antigen particles were partially purified from a crude extract of *H. polymorpha* strain preS/S-B-431 as described above in item 3a. This preparation was tested for reaction with murine monoclonal antibodies (Mabs) directed against epitopes located on the preS1, preS2 and S regions of the surface antigen protein and for the presence of the receptor for polymers of human serum albumin (pHSA-receptor) on the preS2 region.

C1. Reaction with MabS1.1

A murine monoclonal antibody (Mab) S1.1 directed against a preS1 epitope of the HBV surface antigen protein was used to detect the presence of this site on the composite particle by an ELISA assay. MabS1.1 was coated on the wells of a microtitre plate (Immunoplate I; Nunc, Gibco Europe, Ghent, Belgium) and incubated with the partially purified crude extract. After washing to remove non-bound material, capture of reactive particles was revealed by incubation with MabS1.1 coupled to horse radish peroxidase by the method of Wilson and Nakame, 1978.

Colour development to reveal second antibody binding was with orthophenylenediamine as chromogen. Absorbance was read at 490 nm (with 620 nm for the reference filter) in an Intermed Immunoreader, NJ 2000 (Analis, Ghent, Belgium).

The partially purified extract from *H. polymorpha* strain preS/S-B-431 gave a positive reaction in the test indicating capture by and binding MabS1.1 which is specific for the preS1 region. Surface antigen particles containing only S-protein purified from *S. cerevisiae* RIT4376 (Harford et al., 1987) gave no reaction in this test.

C2. Reaction with MabS2.5

Murine monoclonal antibody S2.5 is directed against the preS2 region of the HBV surface antigen. This Mab was used in an ELISA test to determine the presence of the preS2 epitope on the composite particles. MabS2.5 was coated on wells of a microtitre plate and incubated with the partially purified cell extract from *H. polymorpha* preS/S-B-431. Antigen binding was revealed by incubation with MabS2.5 coupled with horseradish peroxidase and colour development as described above. The partially purified cell extract from *H. polymorpha* preS/S-B-431 gave a positive reaction in the test indicating the presence of the preS2 region epitope on the surface antigen particles. Surface antigen particles containing only S-protein purified from *S. cerevisiae* RIT4376 gave no reaction in the test.

C3. Reaction with Mabs RF1 and S1.1 (HRP)

Murine monoclonal antibody RF1 (H. Thomas, Royal Free Hospital, London, U.K.) is directed against a conformational dependant epitope located in the S region and was used in an ELISA test. This Mab was used to coat wells of microtitre plates and incubated with the partially purified extract of *H. polymorpha* strain preS/S-B-431. Particle binding was revealed by incubation with the horseradish peroxidase coupled S1.1 Mab described in section C.1 above. The partially purified extract from *H. polymorpha* gave a positive result in the test whereas surface antigen particles purified from *S. cerevisiae* RIT4376 gave no reaction.

C4. Assay for the pHSA receptor

An assay for the detection of the pHSA receptor present on the preS2 region was made according to the procedure of Pontisso et al. (1983).

Polymerised human serum albumin was coated on the wells of a microtitre plate and incubated with the partially purified cell extract of *H. polymorpha* strain preS/S-B-431. After washing to remove non-bound material, particles captured on the plate were detected by incubation with polyclonal anti-HBsAq rabbit antibodies labelled with 125 (AUSAB kit). The partially purified extract from *H. polymorpha* gave a positive reaction in the test whereas HBsAg purified from *S. cerevisiae* RIT4376 gave no reaction in the test.

The above results show that the HBsAg reactive material present in the partially purified extract from *H. polymorpha* contains antigenic sites specifically bound by Mabs directed against epitopes in the preS1, preS2 and S regions of HBV surface antigen and that this material also contains a site reacting with pHSA.

d) Immune precipitation of composite particles.

To determine whether the AUSRIA reactive material present in a partially purified extract of *H. polymorpha* strain PreS/S-B-431 contained composite particles an immune precipitation with a monoclonal antibody specific for the preS1 protein was performed.

Immune complexes were captured by formalin-fixed *Staphylococcus aureus* (Staph A) cells (Immunoprecipitin, BRL, Gaithesburg, Md., USA) using rabbit anti-mouse serum as sandwich antibody between the monoclonal antibody and the Staph A cells. Staph A cells were pre-treated as recommended by the supplier and finally washed and resuspended at 10% (w/v) in PBS. The Staph A cells (120 μl of 10% w/v suspension) were then incubated with 20 μl of rabbit anti-mouse serum (RAM) for 2 hours at room temperature. The Staph A-RAM complex was collected by centrifugation, washed twice with PBS containing 0.1% (v/v) Tween 20, and finally resuspended at about 10% (w/v) in PBS containing 0.1% (v/v) Tween 20.

To a partially purified preparation of particles of *H. polymorpha* strain preS/S-B-431 obtained as described above and to a sample of yeast-derived S-protein HBsAg particles (lot HB193, Smith Kline Biologicals, Rixensart, Belgium) both containing 2 μg AUSRIA reactive material in 500 μl was added 1 μl of MabS1.1 (638 μg protein per ml) and the mixtures were incubated for 2 hours at room temperature. 20 μl of the Staph A-RAM complex was then added and incubation continued overnight at 4° C. Immune complexes formed were collected by centrifugation, washed 5 times with PBS containing 0.1% (v/v) Tween 20 and once with PBS before resuspending the final pellets in sample buffer for SDS polyacrylamide gel electrophoresis. The immune precipitates were analysed by immunoblotting as described below using mouse monoclonal antibody RF6 (H. Thomas, Royal Free Hospital, London) for detection of HBSAg protein species. Monoclonal antibody RF6 is directed against a denaturation and reduction resistant epitope of plasma derived HBsAg and competes in binding experiments with monoclonal HBS1.

The immune blot showed that the immune precipitate obtained from the *H. polymorpha* preS/S-B-431 particles contained not only the preS1-protein but also the S-protein while the immune precipitate from the Saccharomyces derived HBsAg contained no S-protein.

This confirms that composite particles of mixed polypeptide composition are present in the material partially purified from *H. polymorpha* strain preS/S-B-431 cell extracts.

e) Electron microscopy

Partially purified HBsAg particles from *H. polymorpha* strain preS/S-B-431 were examined by electron microscopy. Material was diluted in 20 mM Tris-HCl buffer pH 8.2 with 0.1% (w/v) bovine serum albumin and sedimented onto copper/rhodium grids covered with a film of celloidin before staining with uranyl acetate. Examination in the electron microscope showed the presence of spheroidal to spherical particles with a mean diameter of 27 nm. This size is within the range of mean particle diameters measured by the same technique for a series of HBsAg preparations purified from *S. cerevisiae* strain RIT4376 [Petre, J. et al., Postgrad. Medical Suppl. 2, 73–81 (1987)].

EXAMPLE D.5

5. Comparison of composite particles expressed in *H. polymorpha* and *S. cerevisiae*

Cultures of strain preS/S-C-453 of *H. polymorpha* and *S. cerevisiae* strain Y1108 were grown in the S-medium as described in Materials, 5d. Strain Y1108 is a diploid strain of *S. cerevisiae* expressing both the preS1 and S-proteins from expression cassettes integrated into the genome by Ty vectors. The strain contains 5–7 copies of a preS1 expression cassette and 3–4 copies of a S-expression cassette. The strain requires tryptophan for growth. Construction and chromosomal integration of such expression cassettes using Ty vectors is described in copending U.S. Ser. No. 07/292,202 filed Dec. 30, 1988 assigned to SmithKline Beckman Corporation which is hereby incorporated as reference. Glycerol at 1.5% (w/v) was used as carbon source for growth of *H. polymorpha*. A series of 2 liter erlenmeyer flasks containing 400 ml of medium were inoculated with *H. polymorpha* strain preS/S-C-453 and incubated on an orbital shaker for about 33 hours at 30° C. until exhaustion of glycerol. The cells from three flasks were harvested by centrifugation and the cell pellet stored at −70° C. until further processing. 100 ml of culture medium was removed from each of six further flasks and replaced with 100 ml of fresh medium containing 4% (w/v) methanol. Incubation was then continued.

Three cultures were harvested by centrifugation after a further 14 hours incubation and a further three cultures harvested after 38 hours incubation in the presence of methanol. The cells were recovered by centrifugation and the cell pellet stored at −70° C. until further processing.

In a second experiment cultures of *S. cerevisiae* Y1108 were grown as described above and harvested after 19.5 hours incubation. Cultures of *H. polymorpha* preS/S-C-453 were also grown as described above except that cells were harvested after 26 hours growth in glycerol medium and after 45 hours in methanol containing medium.

Cell pellets of *Hansenula polymorpha* were resuspended at a concentration of about 25% wet cell pellet weight per volume in buffer containing 0.5% (w/v) Tween 20, 2 mM EDTA, 4 mM PMSF (phenylmethylsulphonylfluoride), 5% (w/v) isopropanol and 50 mM sodium phosphate pH 9.0 10 ml of this mixture was passaged 6 times in a French Press at 20,000 psi to break the cells. The crude cell extract was then clarified by centrifugation at 17,000 g for 45 minutes at 4° C. and the supernatant recovered. Cell pellets of *S. cerevisiae* were treated identically except that cells were resuspended at a concentration of about 50% wet cell pellet weight per volume of the buffer described above.

The protein content of each supernatant was determined by the method of Lowry et al. (1951). The clarified cell extracts were assayed for HBsAg by AUSRIA and for the presence of a preS1 protein epitope by an Elisa assay. The monoclonal S1.1 Elisa assay was performed as follows. Wells of plastic trays (Nunc Immunoplate 1, Gibco Europe, Ghent, Belgium) were coated with S1.1 mouse monoclonal antibody in 50 mM sodium bicarbonate buffer pH 9.6 for 2 hours at 37° C., and the antibody solution removed. The wells were then blocked by incubation with a PBS solution containing 1% (w/v) bovine serum albumin for 1 hour at 37° C. Serial two fold dilutions of cell extracts made in PBS, 0.2% (w/v) bovine serum albumin were then added to wells and incubated. 1 hour at 37° C.

The wells were then washed 3 times with 0.9% (w/v) NaCl, 0.05% (w/v) Tween 20. Antigen capture was revealed by incubation with monoclonal antibody S1.1 coupled to horseradish peroxidase by the method of Wilson and Nakane (1978).

Conjugated antibody in PBS, 0.2% (w/v) bovine serum albumin was added to each well and incubated for 1 hour at 37° C. Second antibody binding was revealed by addition of 100 µl of a solution containing 4 mg o-phenylenediamine (Sigma), 15 µl hydrogen peroxide dissolved in 10 ml 0.1 M $KH_2PO_4$ pH 6.0 and incubation for 15 minutes at room temperature. The reaction was blocked by addition of 25 µl 1 N $H_2SO_4$, and the optical density read at 490 nm (with 620 nm for the reference filter) in an Intermed Immunoreader, NJ200 (Analis, Ghent, Belgium). Results were calculated from the linear portion of the optical density curves obtained and expressed as Optical Density Units per mg protein.

The amount of AUSRIA reactive HBsAg and preS1-protein determined in the cell extracts of *S. cerevisiae* and *H. polymorpha* from the two experiments are shown in Tables 4 and 5. The amount of AUSRIA reactive materials found in crude extracts of *S. cerevisiae* strain Y1108 is about one hundred-fold less than in extracts of *H. polymorpha* preSIS-C-453 induced for 38 to 45 hours in methanol. The amount of preS-protein assayed by Elisa is about 3 to 8-fold less indicating that *S. cerevisiae* strain Y1108 makes a greater proportion of preS1-piotein to S-protein than does *H. polymorpha* strain preS/S-C-453.

TABLE 4

AUSRIA assay of crude cell extracts

| Cell extract | Flask Number | Protein (mg/ml) | HBsAg (AUSRIA) % total protein | preS1-protein Elisa; OD units per mg protein |
|---|---|---|---|---|
| *S. cerevisiae* Y1108 | a | 16.2 | 0.011 | 2.9 |
| | b | 18.0 | 0.008 | 3.0 |
| | c | 12.0 | 0.010 | 4.4 |
| *H. polymorpha* preS/S-C-453 glycerol culture | a | 6.8 | 0.077 | 2.4 |
| | b | 7.4 | 0.123 | 2.3 |
| | c | 9.2 | 0.143 | 1.7 |
| Methanol induced 38 hours | a | 5.5 | 1.15 | 9.2 |
| | d | 7.0 | 1.40 | 11.3 |
| | c | 7.4 | 1.46 | 8.8 |

TABLE 5

AUSRIA assay of crude cell extracts

| Cell extract protein | Flask Number | Protein (mg/ml) | HBsAg (AUSRIA) % total protein | preS1-protein Elisa; OD units per mg protein |
|---|---|---|---|---|
| *S. cerevisiae* Y1108 | a | 13.3 | 0.009 | 8.3 |
| | b | 15.0 | 0.015 | 9.7 |
| | c | 17.1 | 0.013 | 8.9 |
| *H. polymorpha* preS/S-C-453 glycerol culture | a | 8.4 | 0.070 | 1.3 |
| | b | 8.2 | 0.061 | 0.3 |
| | c | 7.9 | 0.082 | 0.3 |
| Methanol induced 45 hours | a | 6.3 | 1.106 | 4.1 |
| | d | 6.5 | 1.314 | 6.8 |
| | c | 7.7 | 1.688 | 5.1 |

The results were confirmed by immunoblotting of the extracts from the first experiment together with extracts of methanol induced cultures of strains 454 and 448-C4 as controls.

Samples containing 15 µg of protein were electrophoresed through 12.5% separating, 5% stacking gels according to the method of Laemmli (1971) and subjected to immunoblotting as described above in Materials and Methods 5a using monoclonal HBS1 for detection.

Extracts from strain preS/S-C-453 show a strongly reactive band at 24 kD related to the S-protein and a band at 38–39 kD related to preS-protein. A 45 kD band is barely detectable. In contrast extracts from *S. cerevisiae* strain Y1108 show weak bands at 24 kD and 45 kD. The 38–39 kD doublet band of preS-protein was barely detectable. The immunoblotting result confirms that *S. cerevisiae* expresses less S and preS-proteins than methanol induced *H. polymorpha* and that the preS protein expressed by *S. cerevisiae* is predominantly the glycosylated 45 kD form.

EXAMPLE D.6

Myristoylation of pres protein in *H. polymorpha*.

Cultures of strain LR9, strain 452 and 453 were grown in shake flasks on minimal medium with 2.5% v/v glycerol for 24 hours and methanol (1%, v/v) was then added. 6 hours after methanol addition, tritium labelled myristic acid was added and the cultures incubated for a further 16 hours. Cells were collected, washed and disrupted with glass beads in the presence of 1% SDS and β-mercaptoethanol. The extracted proteins were separated by SDS-PAGE gel electrophoresis and visualised by immunoblotting with monoclonal HBS1 and by fluorography. The results showed that a band corresponding to the 38/39 Kd preS1 protein was labelled in the extracts of stains 452 and 453 but not in the extract from LR9. This is consistent with post translational removal of the N-terminal methionine and myristoylation of the glycine residue at the second position of the polypeptide (Towler and Gordon, Ann. Rev. Biochem., 57:69–99, 1988).

EXAMPLE D.7

Immunogenicity of pres antigens from H. polymorpha

Crude protein extracts were prepared from methanol grown cultures of strains 452 and 454 and adsorbed onto aluminium hydroxide at 1 mg/ml final concentration. The preS1 epitope content of each extract was measured in an ELISA assay using monoclonal antibody S1.1 and preS1 protein partially purified from S. cerivisiae as standard. Immune complexes for injection were also formed by incubating 600 mcl of S1.1 monoclonal antibody with 1 ml of Sepharose Protein G 4 Fast Flow (obtained from Pharmacia LKB, Brussels, Belgium) for 2 hours at 4° C. The mixture was then centrifuged, washed with PBS and the pellet resuspended in 1 ml PBS. 250 mcl of this suspension was added to 3.4 ml of each crude cell extract and the mixture incubated for 1 hour at 20° C.

Following incubation the Sepharose Protein G/S1.1/crude protein mixture was centrifuged and the pellet resuspended in 10 mM sodium phosphate buffer. Half of this material was adsorbed onto aluminium hydroxide at 1 mg/ml final concentration.

Groups of 5 Balb/c mice were injected intraperitoneally with the four preparations. One month later the mice received an intraperitoneal booster injection of 1 mcg of aluminium hydroxide adsorbed, partially purified particles from a methanol grown culture of strain 453. The mice were bled 15 days later. The titres of anti-S, anti-preS2 and anti-preS1 antibodies in the sera were determined in the same way as described hereinbelow.

Table 6 shows the respective antibody titres induced in Balb/c mice expressed as Geometric Mean Titer.

The results show that anti-pres antibodies are induced in mice when injected with preS1-S2-S containing extract (strain 454) or with extract containing composite particles (strain 452) and boosted with composite particles (strain 453).

TABLE 6

| Preparation | mcg of antigen injected (a)(b) | α-HBS GMT in mIU/m | α-120-145 GMT (c) | α12-32 GMT (c) | α32-47 GMT (c) |
|---|---|---|---|---|---|
| Strain 454 crude extract | 222 | 17755 | 688 | 240 | 612 |
| Immune ppt | 155 | 616 | 518 | 59 | 1400 |

TABLE 6-continued

| Preparation | mcg of antigen injected (a)(b) | α-HBS GMT in mIU/m | α-120-145 GMT (c) | α12-32 GMT (c) | α32-47 GMT (c) |
|---|---|---|---|---|---|
| Strain 452 crude extract | 48 | 124803 | 426 | 59 | <100 |
| Immune ppt | 48 | 119903 | 487 | 64 | 784 |

*Notes
(a) Relative to preS1-S2-S antigen from S. cerevisiae
(b) All mice received a booster injection at day 30 of particles partially purified from strain 453.
(c) Titres are expressed as the inverted dilution giving an OD of 1.0 in the assay.

Part E

EXAMPLE E.1

Expression of composite particles containing both modified preS1-S2-S (L*) and S antigens of single or mixed subtype.

(1) Construction of a L* (ad) coding sequence

A modified preS1-S2-S (L*) coding sequence suitable for direct insertion on the Hansenula expression vector pMPT-121 (FIG. 11) was constructed as follows. Plasmid DNA of pRIT13192 described hereinbelow was digested with HindIII endonuclease to obtain linear fragments. About 1 ng of this DNA was mixed with oligonucleotides BC74 and BC75 and subjected to polymerase chain reaction (PCR) amplification.

PCR technology is well known and is disclosed in 'PCR Protocols, A guide to methods and applications'; Innes M. A. et al. (Eds.) Academic Press Inc., San Diego Calif. 1989.

Oligonucleotides BC74 and BC75 have the sequences shown below and were synthesised by conventional phosphoramidite chemistry.

BC74 5' CCC AGA TCT AAG CTT ATT AAA TGT ATA CCC A 3'

BC75 5' CCC GAA TTC AAA ATG GGG ACG AAT CTT TCT 3'

Oligonucleotide BC74 has homology to the 3' end of the L* coding sequence on pRIT13192 together with a HindIII and BglII retriction site extension. Oligonucleotide BC75 has homology to the 5' end of the L* coding sequence on pRIT13192 together with an EcoRI site and a short leader sequence before the ATG codon as extension. About 1 ng of template pRIT13192 DNA was mixed with 50 mM KCl, 10 mM Tris-HCl pH8.3, 1.5 mM MgCl$_2$, 0.01% (w/v) gelatin, 200 μM each of dATP, dCTP, dGTP and dTTP, 1 μM of each oligonucleotide primer and 2.5 units of Taq polymerase in a final volume of 100 μl using commercially available DNA amplification reagents (Gene Amp DNA Amplification Reagent kit from Perkin Elmer Cetus; obtainable from Vander Heyden, Brussels). The mixture was subjected to 25 cycles of denaturation (2 min, 92°), annealing (2 min, 48°) and extension (2 min, 72°) using a DNA Thermal Cycler (Perkin Elmer Cetus; obtained from Vander Heyden, Brussels). One ng of the modified, amplified L* coding sequence fragment so obtained was then reamplified in a second round with the same oligonucleotides in the same conditions and purified from the reaction mixture by ethanol precipitation.

An aliquot of about 250 ng of the 870 bp adapted L* fragment DNA was digested with EcoRI and BglII endonucleases and cloned between the EcoRI and BglII sites of a pBR327 derivative plasmid, pRIT12555 to give pRIT13488. pRIT12555 consists of the pBR327 replicon with a BglII site introduced by linker insertion between the EcoRI and ClaI sites of the original plasmid.

A further aliquot of the adapted L* fragment was digested with EcoRI and BglII endonucleases and inserted between the EcoRI and BglII sites of the plasmid pMPT121 (FIG. 11). This places the L* coding sequence between the MOX promoter and the MOX terminator on an expression plasmid suitable for introduction into *H. polymorpha* by transformation. DNA sequencing of the resulting plasmid, pL*-11, showed that the L* coding region sequence was correct.

(2) Construction of an S-(ay) coding sequence pRIT13490 is a pBR322 derivative plasmid containing a complete preS2-S coding sequence obtained by conventional recombinant DNA manipulations from pRIT10601 which contains the complete genome of a hepatitis B virus of ay subtype cloned on pBR322. pRIT10601 was deposited under the Budapest Treaty with the American Type Culture Collection, Rockville Md. on Jun. 2, 1982 under Accession Number ATCC 39132.

It will be appreciated by one of skill in the art that in the following manipulations described below pRIT13490 could be substituted by pRIT10601 or any other cloned HBV fragment containing a complete S-(ay) coding sequence. DNA of pRIT13490 was digested with HindIII endonuclease to linearize the plasmid and mixed with the oligonucleotide BC74 described above and with oligonucleotide BC73 which has homology to the 5' end of the S coding sequence on pRIT13490 together with an EcoRI site and a short leader sequence before the ATG codon as extension.

BC73 5' CCC GAA TTC AAA ATG GAG AAC ATC ACA TCA.3'

The mixture of HindIII treated pRIT13490 and oligonucleotides was amplified by 2 rounds of PCR as described above to generate a 700 bp S-(ay) coding sequence fragment flanked by EcoRI and BglII restriction sites. About 250 ng of this material was digested with EcoRI and BglII endonucleases and cloned between the EcoRI and BglII sites of pRIT12555 to give pRIT13438. The correctness of the S-(ay) coding sequence on pRIT13438 was verified by DNA sequencing.

(3) Construction of a L* (ad/ay) coding sequence

About 1 ng of the PCR amplified fragment used to construct pRIT13488 was further amplified by 2 rounds of PCR amplification in the presence of oligonucleotides BC75 (described above) and BC30 having the following sequence.

BC30 5' ACG AGT CTA GAC TCT GCG GTA 3'

BC30 is homologous to the region around the XbaI site of the S coding sequence derived from the pRIT10616 HB virus clone of ad subtype. A 280 bp fragment was recovered from the amplification and about 250 ng of this was digested with EcoRI and XbaI endonucleases.

About 1 ng of the. PCR amplified fragment used to construct pRIT13438 was further amplified by 2 rounds of PCR amplification in the presence of oligonucleotides BC74 (described above) and BC12 having the following sequence.

BC12 5' ATG GAG AAC ATC ACA TCA 3'

BC12 is homologous to the first 6 codons of the S coding sequences of the HB virions cloned on pRIT10601 and pRIT10616. Following PCR amplification about 250 ng of the 700 bp fragment was digested with XbaI and BglII endonucleases.

The two endonuclease digested, PCR amplified fragments were then ligated with EcoRI, BglII digested DNA of pRIT12555.

A plasmid, pRIT13491, was recovered consisting of pRIT12555 together with the EcoRI-XbaI fragment from the PCR amplification of the fragment used to construct pRIT13488 and the XbaI-BglII fragment from the PCR amplificiation of the frament used to construct pRIT13438. DNA sequencing of the L* coding insert on pRIT13491 showed that an error had been introduced at the 5th amino acid of the S coding region. To correct this, the PCR amplified fragment used to construct pRIT13488 above was digested with EcoRI and XbaI endonucleases and used to replace the corresponding EcoRI-XbaI fragment on pRIT13491 which contained the error. The resulting plasmid pRIT13489 specifies a "hybrid" L* coding sequence in which the part from the ATG initiation codon to the XbaI site is derived from ad subtype virus sequence and the part from the XbaI site to the termination codon is derived from ay subtype virus sequence. The corresponding polypeptide will have the ay subtype.

The EcoRI-BglII fragment from pRIT13489 containing the hybrid L* (ad-ay) coding sequence was then inserted between the EcoRI and BglII sites on plasmid pMPT-121 to give the *H. polymorpha* expression vector pL* 13.

(4) Expression in *H. polymorpha* of both modified preS1-S2-S (L*) and S antigens to form composite particles.

Several strains were constructed which were characterised by different ratios of L* and S expression as well as different total expression levels. These differences were achieved by variation of the copy number of the expression cassette per genome.

*H. polymorpha* strain RB10 was transformed as described above with the plasmid pL* 11 bearing the L* (ad)-expression cassette. Transformation yielded several strains containing variable numbers of expression cassettes integrated into the genome. Two of these strains, designated L13/1 and L19/1, were analysed in more detail. Southern blot analysis revealed that these strains contain several copies of the L* (ad)-expression cassette. The L* (ad)-expression level of these strains was assayed by western blot analysis using monoclonal antibody HBS1. A band of 33 kD corresponding to L* antigen was detected. Expression levels were estimated to be about 0.5–2% of total cell protein when cells were grown in glycerol medium followed by addition of methanol.

The L* (ad)-expressing strains were transformed again with plasmid pRB-S-322 bearing the S(ad)-gene under control of the MOX-promoter. pRB-s-322 is described above (see FIG. 7). Resistance against gentamycin was used as a transformation marker. Stable integrants were obtained employing the methods described above. Two of the strains obtained were studied in more detail: strain LMS9/1 and strain LMS26/2, both derived from recipient strain L13/1. Southern blot analysis revealed that these strains carry several copies of the L*(ad) expression cassette as well as several copies of the S(ad) expression cassette.

The expression of L* and S antigens in the *H. polymorpha* transformants was tested by Western blotting using monoclonal antibodies HBS1 and S1.1 as described above. A spectrum of strains was obtained which express different ratios of L* to S antigen. HBS1 antibodies detect a 24 kD protein corresponding to S antigen, and 30 and 33 kD bands corresponding to L* antigen. S1.1 antibodies specific for the preS1 region reveal a 33 kD band as well as the 30 kD band. The L*/S ratios were estimated to be about 1:1 for strain LMS9/1 and about 1:10 for strain LMS26/2. Expression levels were estimated to be about 5–6% of the total cell protein when cells were grown under induced conditions with methanol.

Glycosylation studies showed that the 33 kD protein represents a glycosylated form of the L* antigen. When crude protein extracts from strains LMS9/1 and LMS26/2 were incubated with endoglycosidase H, the 33 kD band shifted to the apparent molecular weight of 30 kD. 30 kD is the expected molecular weight of L* antigen. Thus part of the L* antigen produced in *H. polymorpha* is "core"-glycosylated while the remainder constitutes the unglycosylated form of L*.

In order to test for particle formation crude cell extract from strain LMS9/1 was subjected to CsCl density gradient centrifugation. Gradient fractions were analysed by immunoblotting using antibody HBS1. A peak of HBsAg-reactive material including the 24 kD S antigen and the 30 and 33 kD L* antigen forms was observed at a density of 1.18 g/cm³. This result indicates that composite particles were formed in *H. polymorpha* strains coexpressing the L* and S polypeptides.

In a further variation of the invention a *H. polymorpha* strain coexpressing the L* and S proteins was obtained by further transforming strain 415 described above. Strain 415 carries between 50–100 S(ad) expression cassettes under the control of the MOX promoter and is characterised by a high S antigen expression level.

A L* (ad) expression vector containing a kanamycin-resistance gene was constructed; A 3.5 kb NruI-fragment encoding the kanamycin-resistance gene under control of the ADHI promoter and the HARS sequence was isolated from plasmid pHK2 (FIG. 6). Plasmid pL*11 was digested with NruI and SalI endonucleases and made blunt ended by fill-in with Klenow DNA polymerase. The NruI/SalI-digest eliminated the HARS sequence from the pL*11-vector. The NruI-fragment from pHK2 was then ligated to the blunt ended large NruI-SalI fragment of the pL*11-vector thus introducing the kanamycin-resistance gene and re-introducing the HARS sequence which had been eliminated. The resulting plasmid is designated pKL*1 or pKL*10 depending on the orientation of the kanamycin resistance gene cassette. The structure of pKL*1 is shown in FIG. 12. These plasmids can be introduced into *H. polymorpha* by transformation and selection for gentamycin resistance as described above in Methods.

Strain 415 was transformed with pKL*1 and pKL*10 carrying the L*(ad) expression cassette and stable transformants were obtained after selection for resistance to gentamycin. Several strains were further analysed. Western blot analysis using antibody HBS1 showed a 24 kD protein corresponding to S antigen as well as the 30 and 33 kD bands corresponding to the unglycosylated and glycosylated forms of L* antigen respectively. In these 415 derived strains the L*/S ratio varied from about 1:1 in strain LMS05-14-1 to about 1:20 in strain LMS05-12-1. In strains grown under fully induced conditions with methanol, L*/S antigen expression levels amounted to an estimated 5–6% of the total cell protein. No differences between strains transformed with pKL*1 and strains transformed with pKL*10 were observed.

(5) Co-expression of L* and S antigens leading to composite particles with mixed subtype.

To obtain *H. polymorpha* strains which produce L*/S-particles with a mixed (ad/ay) subtype, plasmid pL*13 bearing a L* (ad/ay) expression cassette was transformed into *H. polymorpha* RB10.

Stable clones expressing the L* antigen can be obtained and retransformed with plasmid pRB-S-322 carrying the S(ad) expression cassette with selection for gentamycin resistance. Stable strains from the second transformation are analysed by Western blotting and AUSRIA assays to determine the respective expression levels of the L* (ad/ay) and S(ad) antigens and the total level of surface antigen expression.

Strain 415 expressing S(ad) protein may also be retransformed with a derivative of pL*13 which carries a functional gentamycin resistance marker to generate stable transformants expressing both the L* (ad/ay) and S(ad) polypeptides in the form of composite particles with both ad and ay subtype specificities.

EXAMPLE F.1

Construction of plasmid pRIT12979 coding for a non-myristylated HBV large protein The outline of the construction of plasmid pRIT12979 is shown in FIGS. 13 and 14. FIG. 13 shows the steps for constructing an *E. coli* plasmid harbouring a ΔGly13 L protein-expression cassette, pRIT12998. FIG. 14 illustrates the procedure for obtaining a yeast plasmid pRIT12979 capable of expressing a ΔGly13 L protein.

It is understood that the Gly 13 residue is encoded by the second codon of the L protein coding sequence represented in Table A.

The starting material for this construction is plasmid pRIT12863, a derivative of pBR327 which contains the TDH3 promoter region and the ARG3 transcription termination region [Cabezon et al., *Proc. Natl. Acad. Sci. USA*, 81:6594–6598 (1984)] separated by a BamHI, SmaI, EcoRI linker. A linker containing a BglII site is placed upstream of the TDH3 promoter sequences. pBR327 is described in Soberon et al, *Gene*, 9:287–305 (1980) and was obtained from F. Bolivar. (Department of Molecular Biology, National University of Mexico). This plasmid may be recovered as described in co-pending U.S. application Ser. No. 009,325.

The expression cassette for the non-myristylated L protein is constructed within the linker region of pRIT12863.

The plasmid pRIT12816, which is an *E. coli* plasmid derived from pAS1 [Rosenberg et al, *Methods Enzymol.*, 101:123–164 (1983)], harbours the coding region for the large HBV (adw serotype) protein flanked by an NcoI site (overlapping the ATG at codon position 12 in the L protein coding sequence) and by an EcoRI site beyond the stop codon. This plasmid is constructed by conventional recombinant DNA techniques [see, T. Maniatis et al, cited above].

Plasmid pRIT12816 is digested with BstXI and EcoRI and the 304 bp BstXI-EcoRI fragment encoding the N-terminal portion of the preS1 region is recovered and ligated to the following synthetic BamHI-BstXI adaptor:

```
 BamHI    XbaI                               BstXI
GATCCCTCTAG ACG AAT CTT TCT GTT CCC AAC C
    GGAGATC TGG TTA TAA AGA CAA GGG TT.
```

This fragment is inserted into pRIT12863, previously digested with BamHI and EcoRI enzymes, resulting in plasmid pRIT12996. The BamHI-BstXI synthetic adaptor harbours the N-terminal preS1 region, but does not provide the correct reading frame with the BamHI site placed at the ATG residue of the TDH3 promoter. The correct reading frame is provided by digesting pRIT12996 with BamHI and XbaI, followed by treatment with mung bean enzyme to eliminate the protruding extensions and ligation. This procedure produced plasmid pRIT12997.

Finally, the 839 bp EcoRI fragment from pRIT12816 was inserted into the EcoRI site of pRIT12997 in the correct orientation to recover the complete coding sequence for the ΔGly L protein. The resulting plasmid pRIT12998 contains the expression cassette coding for an L protein which is deleted for Gly13 and cannot serve as substrate for the myristoyl transferase.

To construct a yeast plasmid capable of expressing the ΔGly L protein, plasmid pRIT12998 was digested with BglII and SalI. The 5822 bp BglII-SalI fragment that contains the expression cassette was purified and inserted into a conventional yeast vector pRIT12741 which is a pBR327 derivative that supplies an AmpR gene, the 2p sequences, the E. coli replicon and the LEU2 yeast marker for selection.

The resulting plasmid pRIT12979 was used to transform the LEU-S. cerevisiae strain 10S44$_c$cir° (pep4-3, leu2-3, leu2-112), otherwise called TCY1 or Y482, which is deposited in the American Type Culture Collection, Rockville, Md., U.S.A. under accession number ATCC 20818. After transformation, the resulting LEU+ yeast strain is called Y720.

EXAMPLE F.2

Comparative Characterisation of ΔGly L Protein with L Protein

Yeast strain Y720 of Example F.1 was examined for ΔGly L protein expression in comparison with yeast strain Y587 (TCY1 transformed by pRIT12845) which expresses the L protein. pRIT12845 contains a 3370 bp expression cassette consisting of a HBV DNA derived coding sequence for the 389 amino acids of the L protein flanked 5' by, and under the control of, a 1050 bp TDH3 promoter fragment and 3' by a 1150 bp fragment carrying the ARG3 transcription terminator. pRIT12845 is described in detail in Example 16A of co-pending U.S. patent application Ser. No. 009,325. Yeast strain Y1017, which is TCY1 transformed with pRIT12741, served as a negative control.

A. Myristylation

Cells from Y720, Y587 and Y1017 were labelled with $^3$H-myristic acid as described in co-pending U.S. patent application Ser. No. 009,325. SDS-extracts of these cells were analysed by SDS polyacrylamide gel electrophoresis (SDS-PAGE), followed by both immunoblot and fluorography [See, e.g., Towler and Glaser, Proc. Natl. Acad. Sci., U.S.A., 83:2812–2816 (1986)].

The immunoblot as described in co-pending U.S. patent application Ser. No. 009,325 involved detection with an S-specific monoclonal antibody (Mab), either Mab RF6 [H. Thomas, Royal Free Hospital, London] or Mab HBs1 [SmithKline Biologicals]. These antibodies recognize overlapping denaturation and reduction resistant epitopes in the S protein. The immunoblot showed the expression of two forms of L protein of 38 kd and 45 kd in both Y720 and Y587.

The fluorograph showed the presence of $^3$H label in the 38 kd L protein derived from Y587 cells as described in co-pending U.S. application Ser. No. 009,325. Minor amounts of label were observed in the 45 kd L protein derived therefrom. In contrast, neither the 38 kd nor the 45 kd ΔGly L protein derived from Y720 cells had incorporated the label. This demonstrates that the elimination of the glycine codon in pRIT12979 abolishes the myristylation of the ΔGly L protein in S. cerevisiae.

B. Expression level

Cells from Y720, Y587 and Y1017 were grown under identical conditions in YNB without amino acids [Difco Labs] 0.675% containing 2% glucose in Erlenmeyer flasks. Both total disrupted cells and crude extracts were analyzed by quantitive immunoblot as described in co-pending U.S. application Ser. No. 009,325.

Two-fold serial dilutions of the samples were analyzed and the immunodetection was based on the S-specific Mabs RF6 or HBs1, or a preS1-specific monoclonal antibody, S1.1 [SmithKline Biologicals]. The immunoblots displayed a 2 to 5-fold higher expression level for the ΔGly L protein (Y720) than the myristylated L protein in Y587. Extraction efficiency appeared to be about equal for the non-myristylated and myristylated proteins. The proportion of L protein that was found in the 45 kd glycosylated form was not changed by the elimination of the myristylation.

C. Lipoprotein structures

Crude extracts from Y720 and Y587 cells were subjected to CsCl equilibrium centrifugation. Gradient fractions were analyzed by immunoblot, AUSRIA assay [Abbott Labs], an ELISA assay specific for a preS1 epitope using MAb S1.1, in which MAb S1.1 was coated on the wells of a microtitre plate [Immunoplate I; Gibco Europe] and incubated with the test samples. After washing to remove non-bound material, capture of reactive particles was revealed by incubation with Mab S1.1 coupled to horseradish peroxidase by the method of Wilson and Nakane (1978) in 'Immunofluorescence and Related Techniques', W. Knapp et al., eds., Elsevier, Amsterdam (1978). Colour development to reveal second antibody binding was with orthophenylenediamine as a chromogen. Absorbance was read at 490 nm with 620 nm for the reference filter, in a Intermed Immunoreader, NJ2000 [Analis, Ghent, Belgium].

The antigenic and immunoblot profile were identical. Both the ΔGly L and the wild type L protein banded at a density of about 1.25 g/cm$^3$, demonstrating that both the myristylated and non-myristylated proteins are present as lipoprotein structures in crude cell extracts. Sucrose gradient velocity centrifugation of CsCl equilibrium gradient purified material showed identical sedimentation behaviour for the myristylated and non-myristylated L protein containing lipoprotein structures, indicating that these lipoprotein structures have comparable physical parameters.

EXAMPLE F.3

Construction of plasmids coding for a modified HBV L protein devoid of potential O- and N-glycosylation sites, potential pHSA binding sites, and potential protease sensitive sites An outline of the construction of two yeast vectors: pRIT13192, coding for the expression of a myristylated modified L protein (L*) and pRIT13193, coding for the expression of a non-myristylated modified L protein (ΔGly L*) is presented in FIGS. 15 and 16.

pRIT10616, deposited as ATCC 39131, is digested with BglII, and the largest fragment ligated to the pACYC177 replicon [Chang and Cohen, J. Bacteriol, 134:1141 (1978)], previously digested with BamHI. The intermediate plasmid obtained was digested by EcoRI and religated to obtain pRIT10633, which harbours an incomplete HBV genome from which the pACYC184 vector has been excised.

Plasmid pRIT12331 is a pUC9 [Amersham, U.K. and Pharmacea, Sweden] derivative containing the 1500 bp HindIII-NcoI ARG3 promoter fragment from pRIT10779 [Cabezon et al, Proc. Natl. Acad. Sci. U.S.A., 81:6594–6598 (1984)] fused in the correct orientation to a 681 bp NcoI-EcoRI fragment which contains the S coding sequences with the NcoI site overlapping the ATG codon and the EcoRI site beyond and adjacent to the stop codon, inserted between the HindIII and EcoRI restriction site of pUC9.

pRIT10633 is digested with BstEII and XbaI enzymes. The 648 bp BstEII-XbaI fragment, in which the BstEII extension was filled in by Klenow polymerase, containing the entire PreS1-PreS2 region and the N-terminal sequences of the S region was purified and inserted between the SmaI and XbaI sites of pUC12 [Amersham]. The resulting plasmid is pRIT13188.

Plasmid pRIT13188 was treated with BalI and BamHI, which deleted the preS1 region coding for the amino acids extending from residues 52 to 133 [the codons for amino acid 53 and 132 were included in deletion]. The large fragment was treated with Klenow polymerase and ligated, resulting in plasmid pRIT13189 in which the BamHI site is reformed.

The DNA corresponding to the pres amino acid region extending from residue 145 to 175 [the codons for amino acids 146–174] were deleted by digestion of pRIT13189 with BamHI and XbaI. This vector was ligated to the following synthetic adaptor:

```
BamHI extension                              NcoI extension
   GATCCCAGAGTCAGGGGTCTGTATTTTCCTGCTGGTGG
        GGTCTCAGTCCCCAGACATAAAAGGACGACCACCGTAC AspProArgValArgGlyLeuTyrPheProAlaGlyGly
        135                               145
``` and to the NcoI-XbaI fragment from pRIT12331 containing the N-terminal portion of the S gene. The resulting plasmid is pRIT13190.

The C-terminal region of the S gene, the termination of transcription ARG3 region and the LEU2 yeast gene were added by insertion of the 4145 bp XbaI-SalI fragment from pRIT12660 between the XbaI and SalI sites of pRIT13190. [pRIT12660 contains a 3050 bp expression cassette consisting of a HBV DNA derived coding sequence for the 281 amino acids of the M protein flanked 5' by, and under the control of, a 1050 bp TDH promoter fragment and 3' by a 1150 bp fragment carrying the ARG3 transcription terminator. PRIT 12660 is described in detail in copending U.S. patent application Ser. No. 009,325.] The resulting plasmid pRIT13191 was obtained.

To reconstitute the expression cassettes for the L* and ΔGly L* protein the TDH3 promoter associated either to the N-terminal coding region for a L protein or to the N-terminal coding region for a ΔGly L protein was inserted into pRIT13191.

The 1234 base pair EcoRI-BalI fragment was purified from pRIT12845, containing the L protein coding sequence described above and in U.S. Ser. No. 009,325, and the 1227 bp BglII-BalI fragment was purified from pRIT 12979 containing the ΔGly L protein coding sequence as described above.

Each fragment was mixed with the large SacI-BamHI fragment from pRIT131.91 followed by treatment with T4 polymerase and ligation. The resulting plasmids were designated pRIT13220 and pRIT13222. The coding sequence contained in the expression cassette present in pRIT13220 contains the amino acid residues of 12 to 52 from the preS1 sequence, 133 to 145 from the preS2 sequence and the entire S sequence as indicated in Table A. pRIT13222 is identical to pRIT13220 with the exception of the deletion of the Gly13 codon (GGG).

The last step was the preparation from pRIT13220 and pRIT13222 of the ClaI—ClaI fragment containing each expression cassette for the L* and ΔGly L* proteins respectively and ligation of them to the ClaI—ClaI fragment from plasmid pRIT12845, giving rise to plasmids pRIT13192 and pRIT13193, respectively.

These latter plasmids were used to transform the S. cerevisiae strain TCY1, to give LEU+ strains Y1139 and Y1140, respectively.

EXAMPLE F.4

Expression of L* and ΔGly L* in yeast

Crude yeast extracts from Y587 (L protein), Y1139 and Y1140 (L* and ΔGlyL* respectively) of Example F.3 and Y724 (control S. cerevisiae strain, no expression cassette inserted) were subjected to SDS-PAGE and immunoblot detection with either the S-specific Mab HBs1 or Mab S1.1. The Y1139 and Y1140 extracts showed two bands of estimated molecular weight of about 33 and 30 kd which were specifically recognized by both the preS1 and S specific antibodies.

Treatment of the extracts with endoglycosidase H [New England Nuclear or Boehringer] or glycopepsidase F [Boehringer] resulted in the disappearance of the 33 kd band and an increase of the 30 kd band. This indicates that the 33 kd band represents a glycosylated form of the L* and ΔGly L* protein of Example F.3 carrying one N-linked high mannose type glycan.

Labelling of cell cultures with $^3$H myristic acid followed by analysis of cell extracts by SDS-PAGE, protein blotting and either fluorography or immuno detection, showed a strong presence of $^3$H-label in the 30 kd band and a weak incorporation of $^3$H-label in 33 kd derived from the Y1139 extract. The $^3$H present in these bands was resistant to hydroxylamine treatment. No incorporation of $^3$H-label was observed in the corresponding protein bands from the Y1140 extract. This shows that the L* protein as expressed in Y1139 cells serves as a substrate for the yeast N-myristyl transferase and that deletion of the Gly13 residue in the ΔGly L* protein of Y1140 prevents the myristoylation of the protein.

Analysis of extracts from Y1189 and Y1140 by, CsCl equilibrium and sucrose velocity gradient centrifugation indicated the presence of lipoprotein particles in the extracts.

EXAMPLE F.5

Yeast Strains Y1088 and Y1295 Containing Integrated Copies of an S Protein Expression Cassette Yeast strains harbouring several copies of an S expression cassette integrated in the genome were constructed.

A. Yeast Strain Y1088

The Ty based linear vector pRIT13133-L described in co-pending U.S. patent application Ser. No. 368,401 containing an expression cassette for the S protein (TDH3 promoter—S protein coding sequence—ARG3 termination region) was used to transform both mating types of S. cerevisiae strain 10S69d (ura3, leu2, trp1, gal1, cir°) described in co-pending U.S. patent application Ser. No. 368,401. Different haploid transformants carrying several vector copies integrated in their genomes were crossed with the haploid strains of opposite mating type. Southern blot analyses of genomic DNA isolated from segregants using an S DNA fragment probe, show 2/2 segregations of vector fragments in tetrad analyses. One haploid segregant obtained by this means, which contains 5–7 copies of vector pRIT13133-L, was named Y957. A TRP+ revertant of Y957 was obtained and named Y1088.

B. Yeast Strain Y1295

The Ty based linear vector pRIT13034-L described in co-pending U.S. patent application Ser. No. 368,401 carries an expression cassette for the S protein identical to that in pRIT13133-L. pRIT13034-L carries the CUP1 gene as an additional marker that can be used in CUP1$^s$ or cup1Δ recipient strains.

Two cup1Δ *S. cerevisiae* haploid strains (CUP1 gene disrupted in a strain containing a single copy of that gene) are preferred as recipient yeast strains for this Ty linear vector. These strains have the respective genomes: EJ cup1Δ 3d (ura 3, leu 2, trp 1, gal 1Δ, cup 1Δ, a) and EJ cup 1Δ 7b (ura 3, trp 1, gal 1Δ, cup 1Δ, α) and are described in co-pending U.S. patent application Ser. No. 368,401.

The Ty based linear vector pRIT13034-L containing an expression cassette for the S protein was used to transform *S. cerevisiae* strains EJ cup1Δ 3d as well as EJ cup1Δ 7b. URA3 transformants were isolated, and screened for resistance to copper toxicity. The more resistant transformants appeared to contain 2 to 5 copies of integrated vectors. Classical genetic crosses between these strains and selection of a LEU⁻ TRP⁻ haploid segregant resulted in a haploid strain containing 4 to 5 copies of the S expression cassette. A TRP⁺ revertant of this strain was named Y1295.

EXAMPLE F.6

Construction of yeast strains that co-express the S and L antigens

The yeast plasmids pRIT12845 (L protein), pRIT12979 (ΔGly L protein, Example F.1), pRIT13192 (L* protein, Example F.3), pRIT13193 (ΔGly L* protein, Example F.3) and pRIT12914 (no hepatitis gene inserted) were each used to transform the yeast strain Y1088 to LEU⁺. The resulting yeast strains obtained were designated Y1301 (S, L), Y1302 (S,L Gly L), Y1142 (S, L*), Y1261 (S, ΔGly L*) and Y1141 (control strain expressing S protein only) respectively.

Likewise, pRIT12845, pRIT12979, pRIT13192, pRIT13193 and pRIT12377 (no hepatitis genes inserted) were introduced into the yeast strain Y1295. The resulting yeast strains obtained were designated Y1304 (S, L), Y1305 (S, ΔGly L), Y1306 (S, L*), Y1307 (S, ΔGly L*) and Y1308 (control strain expressing S protein only) respectively.

Co-expression of the S and L proteins was demonstrated by immunoblot analysis of crude cell extracts. Reaction of the blot with Mab HBs1 specific for an S epitope revealed a band of estimated molecular weight of about 23 kd migrating at the position expected for the S protein in each of the extracts of the above mentioned strains.

Extracts from Y1301, Y1302, Y1304 and Y1305 showed in addition to the 23 'kd band, bands of 38 kd and 45 kd migrating like the non-glycosylated and glycosylated forms of the L proteins previously described in U.S. application Ser. No. 009,325, and in Example F.2 herein. Treatment of the extracts with endoglycosidase H resulted in the conversion of the 45 kd band into a 41 kd band while the 23 kd and 38 kd bands were not affected.

Extracts from Y1142, Y1261, Y1306 and Y1307 showed in addition to the 23 kd band, bands of 30 kd and 33 kd migrating like the non-glycosylated and glycosylated forms of the L* and ΔGly L* proteins described in Example F.4. Treatment of the extracts with endoglycosidase H resulted in the conversion of the 33 kd band into a 30 kd band which is identical to the results described in Example F.4.

Labelling of cells with $^3$H myristic acid and analysis of extracts by SDS-PAGE followed by immunoblot and fluorography demonstrated the presence of hydroxylamine treatment resistant $^3$H-label in the 38 kd (extracts from Y1301 and Y1304) and 30 kd bands (extracts from Y1142 and Y1306) with only minor quantities of $^3$H-label in the 45 kd (extracts from Y1301 and Y1304) and 33 kd (extracts from Y1142 and Y1306) protein bands. The corresponding bands in extracts from Y1302, Y1305, Y1261 and Y1307 contained no detectable $^3$H-label.

The 38 kd and 45 kd forms of the L and Gly L proteins are recognized in immunoblots by the preS1-specific Mab's S1.1 and MA18/7 [W. H. Gerlich, University of Göttingen, FRG], the preS2-specific Mab's S2.4, S2.5, S2.7, S2.8, S2.9 and S2.10 [Smith Kline Biologicals]. The 30 kd and 33 kd. forms of the L* and ΔGly L* proteins are recognized by Mab S.1.1 (recognizing an epitope present in amino acid sequence 12–32), MA18/7 (recognizing an epitope present in amino acid sequence 28–47) and S2.5 (recognizing an epitope present in amino acid sequence 133–145). Monoclonal MA 18/7 is reported to inhibit binding of virions to liver cell membranes [Pontisso P. et al., Virology, 173:522–530 (1989)]. The 30 kd and 33 kd forms of the L* and ΔGly L* proteins are not recognized by Mab's S2.4, S2.8, S2.9 which do not react with peptide 120-145 in an ELISA assay nor by Mab's S2.7 and S2.10 which presumably recognize an epitope localised in amino acids 120–137. Monoclonal F35-25 (obtained from M-A Petit, INSERM unité 131, Clamart, France) binds to particles purfied from strain Y1307 as shown by an ELISA assay but does not bind to S particles. This monoclonal recognises a peptide sequence (Petit M-A et al., Molec. Immunol., 26:531–537, 1989) shown to be involved in binding of virus to HepG2 hepatoma cells (Neurath et al., Cell 46:429–436, 1986). Furthermore it has been found that (S, L*) particles bind to HepG2 hepatoma cells and that this binding, and the binding of HB virus particles can be prevented by Monoclonal F35.15 (Petit M-A et al. The 1990 intl. Symposium on Viral Hepatitis and Liver Disease, Abstract 105. Houston, U.S.A., Apr. 4–8, 1990). The Mab Q19/10 [W. H. Gerlich, University of Göttingen, FRG] which recognizes a glycosylation dependent preS2 epitope [Heermann et al. in "Viral Hepatitis and Liver Disease", Eds. A. Zuckerman and Alan R. Liss, Inc. New York pp. 697–700, (1988)] and reacts with the 45 kd form of the L and Gly L proteins does not react with the 30 or 33 kd forms of L* or ΔGly L* proteins. These results are in accordance with the amino acid deletions introduced in the L* and ΔGly L* proteins.

EXAMPLE F.7

Co-expression of S and L or modified L proteins leads to formation of particles of mixed subunit composition Extracts made from each of the strains described in Example F.6 contain HBsAg related antigenicity as demonstrated by positive results in the AUSRIA assay performed according to the manufacturer's instructions [Abbott Lab.]. Extracts from Y1301, X1302, Y1142, Y1261, Y1304, Y1305, Y1306 and Y1307 but not those from Y1141 and Y1308 give a positive reaction in the ELISA-S1.1 assay. When subjected to the CsCl equilibrium centrifugation the AUSRIA and ELISA-S1.1 positive material cobanded around a density of 1.2 g/cm$^3$. Immunoblots confirmed the antigenicity profiles showing that the protein species found in crude extracts cobanded in the AUSRIA and ELISA-S1.1 positive peak. Sucrose velocity gradient centrifugation of dialyzed peak fractions derived from the CsCl equilibrium gradients showed co-sedimentation of the S and L proteins or modified L proteins as determined by AUSRIA, ELISA-S1.1 and immunoblot. This demonstrates that S and L or modified L proteins are assembled into lipoprotein particles.

Immunoprecipitation reactions with Mab S1.1 were used to demonstrate that the S and L or modified L proteins were associated into one physical entity i.e. particles of mixed subunit composition. Extracts were made from yeast strains expressing the S and L or modified L proteins either alone or together, for instance, from Y1139 (L* protein, Example F.3), Y1141 (S protein, Example F.6) and Y1142 (S and L* protein, Example F.6). After semi-purification of the particles by CsCl banding and dialysis of the peak fractions, the particles were subjected to the immunoprecipitation reaction with Mab S.1.1. A mixture of particles from Y1139 and Y1141 was used as an additional control. The L* protein was immunoprecipitated in each case. Coprecipitation of the S protein with the L* protein was observed only from the reaction with particles derived from Y1142.

Identical results were obtained with the other yeast strains that co-express the S and L or modified L proteins (Y1301, Y1302, Y1261, Y1304, Y1305, Y1306, Y1307).

EXAMPLE F.8

Stability and PHSA binding of particles containing the modified L protein

The sensitivity to proteolytic degradation by yeast proteases of the L* and ΔGly L* proteins was analysed by incubating crude cell extracts of Y1142 and Y1161 for either 4 hours at 37° C. or 65 hours at 4° C.

Extracts of Y1301 and Y1302 served as comparative source of L and ΔGly L protein. Analysis of extracts by immunoblot before and after incubation showed an almost complete disappearance of the L and ΔGly L proteins after incubation while the L* and ΔGly L* proteins were still readily detectable.

Purified preparations of particles from strains Y1306 and Y1307 were incubated for 7 days at 37° C. and examined by SDS-PAGE and silver staining to reveal the polypeptides. No detectable degradation of the L* or S polypeptides could be observed.

Particles derived from Y1142 by CsCl banding were tested by a modification of the pHSA binding assay described by Pontisso et al. J. Virol. Methods 6, 151–159 (1983). Microplates (Immunoplate I; Nunc, Gibco Europe) were coated with glutaraldehyde polymerized human serum albumin (5 μg/ml pHSA in PBS, 2 hrs 37° C.) and non-specific protein binding sites on the plates were saturated by incubation (1 hr 37° C.) with PBS containing 1 % bovine serum albumin (BSA). Serial dilutions of the test samples in PBS containing 0.2% BSA were allowed (1 hr 37° C.) to interact with the pHSA coated plates and bound particles were detected (1 hr 37° C.) with a non-limiting concentration of horseradish peroxidase coupled anti-S monoclonal antibody (RF1, H. C. Thomas, Royal Free Hospital, London) in PBS containing 0.2% BSA and revealed with $H_2O_2$ and orthophenylenediamine as substrate. Between incubations the plates were washed with 0.15 M NaCl containing 0.05% Tween 20.

Particles derived from Y1141 served as negative control and purified particles from strain 10S44C cir° containing pRIT12660 as positive control. pHSA binding was greatly diminished in the Y1142 derived particles (2% residual activity) compared to the particles derived from 10S44C cir° harbouring pRIT12660.

PHSA binding was also not detectable with purified particle preparations from strains Y1306 and Y1307.

EXAMPLE F.9

Immunogenicity of particles containing L* protein

The immunogenicity of (S, L*) particles of this invention was studied in Balb/c mice. Particles derived from either Y1142 (S, L*) or Y1141 (S) were partially purified by CsCl banding, and adsorbed on Al(OH)$_3$. Groups of eight mice were injected with either 50 or 5 μg total protein (corresponding to 1 or 0.1 μg antigen by AUSRIA assay) of each antigen preparation at days 0 and 30. The bleeding of mice was done at day 45 and the different assays performed on individual sera. Anti-HBs antibodies were measured with the AusAb kit (Abbott, USA) and expressed in mIU/ml using the Hollinger formula [Hollinger et al., in "Viral Hepatitis" Szumness et al. Franklin Institute Press, Philadelphia pp. 451–466 (1982)].

Anti-preS antibodies were measured using a direct ELISA assay in which selected synthetic peptides (peptide 12-32, peptide 32-47 and peptide 120-145) were adsorbed to polystyrene walls of microplate (Immunoplate I; Nunc, Gibco Europe). Adsorption took place overnight at 4° C. from a solution of 0.5 μg/ml peptide in 0.05 M $Na_2CO_3$/$NaHCO_3$ buffer pH9.6, 100 μl per well. Non-specific sites on the plates were blocked by incubation with 250 μl, 5% foetal bovine serum in PBS during 1 hour at 37° C.

Two fold serial dilutions of the mice sera in PBS containing 1% foetal bovine serum, 0.05% Tween 20 were allowed to react with the peptide-coated plate during 2 hrs at 37° C. (100 μl per well). After washing, bound antibodies were detected by a biotinylated anti-mouse Ig from sheep (Amersham, 500 fold dilution in PBS containing 1% foetal bovine serum, 0.05% Tween 20, 100 μl per well, incubation for 1 hour at 37° C.) and then with a streptavidin—biotinylated horseradish peroxidase complex (Amersham, 1000 fold dilution in PBS containing 1% foetal bovine serum 0.05% Tween 20) during 1 hour at 37° C., 100 μl per well.

Between incubations, the plates were washed with 0.15 M NaCl, 0.05% Tween 20. Final revelation was by $H_2O_2$ and ortho-phenylenediamine as chromogen (15 μl $H_2O$ and 4 mg ortho-phenylenediamine in 10 ml 0.1M potassium phosphate buffer, pH6.0, 100 μl per well). The reaction was stopped after 20 min by the addition of 25 μl 1 N $H_2SO_4$ and absorbance at 490 nm measured in an Intermed Immunoreader, NJ 2000, Analis. The titer for each serum was calculated as the reciprocal of the highest dilution giving an optical density of 1.00.

Table 7 shows the respective antibody titers induced in Balb/c mice expressed as Geometric Mean Titer.

TABLE 7

| Particles derived from | Dose μg | α-HBs GMT in mIU/ml | α120-145 GMT* | α12-32 GMT* | α32-47 GMT* |
|---|---|---|---|---|---|
| Y1142 | 50 | 304000 | 629 | 5222 | 2255 |
| (S, L*) | 5 | 234000 | 212 | 1490 | 785 |
| Y1141 | 50 | 128000 | 202 | 211 | <200 |
| (5) | 5 | 29000 | <200 | 203 | <200 |

(*) The titers were expressed as the inverted dilution for an OD of 1.0.

Particles purified from strain Y1307 (S, Δgly L*) or from strain RIT4376 [Petre J. et al., Postgrad. Med. J. 63, (Suppl.

2), 73–81 (1987)] were adsorbed onto Al(OH)$_3$ and injected into groups of 10 Balb/c mice on days 0 and 30. Mice were bled on day 45 and the pooled immune sera examined for the presence of anti-S and anti-preS antibodies as described above. Table 8 shows the respective antibody titers induced in Balb/c mice.

TABLE 8

| Particles purified from | Dose mcg | α-HBs mIU/ml | α 12-32* | α32-47* |
|---|---|---|---|---|
| Y1307 (S, Δgly L*) | 1 | 7335 | 3128 | 658 |
| RIT4376 (S) | 1 | 5232 | <100 | <100 |

*Titres are expressed as the inverted dilution giving an OD of 1.0 in the assay.

EXAMPLE F.10

Integration of an L* expression cassette in the S. cerevisiae genome by Ty1 mediated homologous recombination It is desirable to integrate both the L* and S protein expression cassettes of this invention into the host genome to provide genetically stable strains and to avoid the 20–30% of plasmidless cells generally seen with 2 micron based S. cerevisiae vectors.

Plasmids pRIT13459 and pRIT13460 were constructed as described for the vector pRIT13009-p in co-pending U.S. patent application Ser. No. 009,325 and in Jacobs et al. (Gene 80:279–291, 1989). The LEU2 gene, isolated as a 2200 bp XhoI-SalI fragment from the vector pCV9 (Petes et al., Cell 19:765, 1980), was inserted between the SalI sites of the Ty1 element on pRIT12927, replacing the original fragment, to give pRIT13144. A 3050 bp HindIII-KpnI fragment carrying the L* expression cassette from pRIT13220 described in Example F.3 was treated with T4 polymerase and ligated into the T4 polymerase treated SalI site remaining on pRIT13144 and using E. coli strain XL1-Blue as transformation recipient. XL1-Blue is described by Hanahan D. in J. Mol. Biol., 166:557–580 (1983) and is commercially available from Stratagene, 11099 North Torrey Pines Road, La Jolla, Calif. Both orientations of insertion of the HindIII-KpnI cassette fragment were obtained; pRIT13459 contains the cassette ARG3 terminator region proximal to the LEU2 gene, pRIT13460 contains the cassette TDH3 promoter proximal to the LEU2 gene.

The large XhoI fragments of about 7700 bp from both pRIT13459 and pRIT13460 were purified from 1% agarose gels and used to transform strain EJ cup1Δ 3d (see Example F.5 above) to leucine independance by the method of Hinnen et al. (Proc. Natl. Acad. Sci. USA, 75:1929, 1978).

LEU+ transformants were obtained with both fragments and 12 colonies from each series were analysed by Western blotting for L* protein expression and by Southern blotting for the number of integrated cassettes. From the transformation of EJ cup1Δ 3d with the fragment from pRIT13459 a strain Y1528 was retained which showed a level of L* expression equivalent to Y1306 and contained 3–5 copies of the cassette. From the transformation of EJ cup1Δ 3d with the fragment from pRIT13460 a strain Y1529 was retained which has similar properties to Y1528.

Both Y1528 and Y1529 were mated with strains Y1295 and its trp$^-$ parent strain Y1215 (see Example F.5 above) and with strain Y1367 to form diploids as follows: Y1528×Y1295=Y1586, Y1528×Y1215=Y1587, Y1528×Y1367=Y1588, Y1529×Y1295=Y1589, Y1529×Y1215=Y1590, Y1529×Y1367=Y1591. Strain Y1367 is α, leu2, trp1, contains 6–8 copies of the same S-protein cassette as strain Y1295 and was obtained using the strains and methods described in the construction of Y1295 in Example F.5.

The diploid strains listed above are screened for their levels of surface antigen expression and the ratio of L* and S polypeptides in the particles by Western blotting, AUSRIA assay and epitope specific ELISA tests using the reagents and methods described above, more particularly in Examples F.2 and F.6. The number and stability of the integrated expression cassettes is determined by Southern blotting. If desired the diploid strains may be sporulated to obtain haploid segregants which may then be screened for expression and genetic stability as described above.

Insertion of the 3050 bp HindIII-KpnI fragment from pRIT13222 on pRIT13144 and following of the above described procedures may be carried out to give S. cerevisiae strains with integrated copies of the Δgly L* expression cassette and strains expressing S, Δgly L* particles.

In a further embodiment the L* expression cassette is inserted on a vector similar to pRIT13134-P [Jacobs et al., Gene 80; 279–291 (1989)] and which carries the URA3 and CUP1 genes as selective markers inserted within the Ty1 element of pRIT12927. Such a vector is identified as pRIT13501 from which a BglII fragment of about 6500 bp with the above elements can be recovered for transformation and integration into an appropriate yeast host by selection for URA+ transformants. Following transformation the number of integrated cassettes may be advantageously increased by selection for increased levels of copper resistance as disclosed in copending U.S. application Ser. No. 07/368,401.

EXAMPLE F.11

Expression of S, L* mixed particles with ad and ay subtype determinants

An integrative vector with an expression cassette for an L* protein of ay subtype was constructed by exchanging the XbaI-SacII fragment encoding the C-terminal part of an ad subtype S protein and part of the ARG transcription terminator with a corresponding fragment from an S-gene of ay subtype. Plasmid pRIT13459 (Example F.10) was digested with XbaI and SacII endonucleases and the largest fragment was purified from a 1% agarose gel and ligated to a purified 1000 bp XbaI-SacII fragment from pRIT10780 to give pRIT13500. pRIT10780 is disclosed in De Wilde et al., Develop. Biol. Standard, 59:99–107, (1985).

The L* coding sequence on pRIT13500 consists of DNA with sequences identical to those from a virus of ad specificity from the ATG codon to the XbaI site and of DNA derived from a virus of ayw specificity from the XbaI site to the termination codon. The expressed L* polypeptide will have ay subtype determinants.

The XhoI fragment of about 7700 bp from pRIT13500 can be integrated into the yeast genome and the resulting transformants mated with strains such as Y1295 and Y1367 by the methods described above so as to obtain strains expressing mixed particles in which the L* polypeptide is of ay subtype and the S polypeptide of ad subtype.

The above description and examples are illustrative and not limiting of the invention. For example, a variety of additional modifications to the L protein may be made, e.g., partial deglycosylation or a combination of various of the modifications made herein, in addition to those mentioned in the examples to generate modified L proteins and particles of mixed or homogeneous subunit composition containing these modified L proteins of appropriate composition for vaccine use.

Additional modifications that may be made include reintroduction of preS sequences, introduction of coding sequences derived from HBV protein coding sequences other than from the envelope gene, e.g. sequences from the HBV core gene, or sequences coding for immunological important amino acid regions from other pathogens. Additional known vector components may be employed to replace the specific marker genes, promoters and linker sequences and the like employed in the examples. Other types of host cells may be employed. The host cells, vectors and vector components employed in these examples are illustrative and may be replaced with other strains or modifications by one of skill in the art. This invention encompasses all improvements and modifications falling within the scope of the following claims.

LIST OF REFERENCES

Burrell et al. Nature 279, 43–47 (1979)

Charnay et al., Proc. Natl. Acad. Sci. USA 76, 2222–2226 (1979)

Cregg et al., Mol. Cell. Biol. 5, 3376–3385 (1985)

Dehoux et al., Gene 48, 155–163 (1986)

Eble et al., Mol. Cell. Biol. 6, 1454–63 (1986)

Eckart et al., Klonierung and Charakterisierung der Gene fü die Dihydroxyacetonsynthase and Methanoloxidase aus der methylotrophen Hefe *Hansenula polymorpha*, Ph.D. Thesis, University Düsseldorf (1988)

Ellis et al., Mol. Cell. Biol. 5, 1111–1121 (1985)

Galibert et al., Nature 281, 646–650 (1979)

Grindley et al., Proc. Natl. Acad. Sci. USA 77, 7176–7180 (1980)

Harford et al., Postgrad. Medical J. 63, Suppl. 2. 65–70 (1987)

Heermann et al., J. Virol. 52, 396–402 (1984)

Hitzemann et al., Nature 293, 717–722 (1981)

Imamura et al., J. Virology 61, 3543–3549 (1987)

Itoh et al., Biochem. Biophys. Res. Comm. 138, 268 (1986)

Jacobs et al., Gene 67, 259–269 (1988)

Janowicz et al., Nucl. Acid Res. 13 3043–3062 (1985)

Jimenez and Davies, Nature 287, 869–871 (1980)

Kingsman et al., Biotech Gen. Eng. Res. 3, 377 (1985)

Klebe et al., Gene 25, 333–341 (1983)

Kniskern et al., Hepatology 8, 82–87 (1988)

Köhler and Milstein, Nature 256, 495–497 (1975)

Laemmli, Nature 227, 680–685 (1970)

Langley et al., Gene 67, 229 (1988)

Ledeboer et al., Nucleic Acid Res. 13, 3063–3081 (1985)

Lowry et al., J. Biol. Chem. 193, 265–275 (1951)

Maniatis et al., Cold Spring Harbor Laboratory, Cold Spring Harbor (1982)

Maxam and Gilbert, Proc. Natl. Acad. Sci. USA 74, 560–564 (1977)

McLachlan et al, W088/06185 (1988)

Michel et al., Proc. Natl. Acad. Sci. USA 81, 7708–7712 (1984)

Milich et al., Science 228, 1195–1199 (1985)

Milich et al., Immunology Today 9, 380–386 (1988)

Murray et al., EP-A-13828 (1980)

Ou et al., J. Virol. 61, 782 (1987)

Persing et al., Proc. Natl. Acad. Sci. USA 82, 3440–44 (1985)

Pontisso et al., J. Virological Methods 6, 151–159 (1983)

Roggenkamp et al., Mol. Gen. Genetics, 302 (1986)

Rutgers et al., Viral Hepatitis and Liver Disease;

Eds. A. S. Zuckermann A. R. Liss, New York 304–308 (1988)

Rutgers et al., Biotech 6, 1065–1070 (1988)

Schwartz and Cantor, Cell 37, 67 (1984)

Sninsky et al., Nature 279, 346–348 (1979)

Southern, J. Mol. Biol. 98, 503–517 (1975)

Stinchcomb et al., Proc. Natl. Acad. Sci. USA 77, 4559–4563

Struhl et al., Proc. Natl. Acad. Sci. USA 76, 1035–1039 (1979)

Szmuness et al., New England J. Med 303, 833–841 (1980)

Tschopp et al., EP-A-0 226 846

Tschumper and Carbon, Gene 10, 157–166 (1980)

Towbin et al., Proc. Nat. Acad. Sci. USA 76, 4350–4354 (1979)

Valenzuela et al., Nature 280, 815–819 (1979)

Valenzuela et al., Nature 298, 347 (1982)

Valenzuela et al., Biotech. 3, 317 (1985)

Wilson and Nakame in "Immunofluorescence and Related Techniques"

(W. Knapp et al., eds., Elsevier, Amsterdam).

What is claimed is:

1. A recombinant DNA molecule comprising a DNA coding sequence for expression of a modified L protein, which is operatively linked to a regulatory sequence, wherein said modified L protein is lacking amino acids 1–11 of naturally occurring L protein, containing at least amino acids 21–47 of the naturally occurring pre-S1 region, and containing at least amino acids 133–145 of the pre-S2 region, wherein said modified hepatitis B virus large surface protein is further characterized by at least one modification selected from the group consisting of:

at least one of the protease sensitive sites at Arg100, Arg137, Gly149, or Arg167 is modified or deleted;

a myristylation site at amino acid residue 13 is lacking;

at least one of the glycosylation sites at amino acid residue 123, 124, or 125 is modified or deleted;

and a human serum albumin binding site at amino acids 120–132 of the naturally occurring pre-S2 region is lacking.

2. A host cell transformed with a recombinant vector comprising a recombinant DNA molecule comprising a DNA coding sequence for expression of a modified L protein, which is operatively linked to a regulatory sequence, wherein said modified L protein is lacking amino acids 1–11 of naturally occurring L protein, containing at least amino acids 21–47 of the naturally occurring pre-S1 region, and containing at least amino acids 133–145 of the pre-S2 region, wherein said modified hepatitis B virus large surface protein is further characterized by at least one modification selected from the group consisting of:

at least one of the protease sensitive sites at Arg100, Arg137, Gly149, or Arg167 is modified or deleted;

a myristylation site at amino acid residue13 is lacking;

at least one of the glycosylation sites at amino acid residue 123, 124, or 125 is modified or deleted;

and the human serum albumin binding site at amino acids 120–132 of the naturally occurring pre-S2 region is lacking.

3. The cell according to claim 2, selected from the group of yeasts consisting of Saccharomyces, Hansenula, Pichia, Candida, Kluyveromyces, and Schizosaccharomyces.

4. The cell according to claim 3, selected from *Saccharomyces cerevisiae* or *Hansenula polymorpha*.

5. The cell according to claim 2, which is additionally transformed with a recombinant DNA vector capable of expressing the S protein of Hepatitis B surface antigen.

6. A method of producing a modified hepatitis B virus large surface protein comprising culturing a cell according to claim 2 in appropriate culture media and isolating said protein from the cell lysate or extract of said culture, wherein said modified hepatitis B virus large surface protein is lacking amino acids 1–11 of naturally occurring L protein, containing at least amino acids 21–47 of the naturally occurring pre-S1 region, and containing at least amino acids 133–145 of the pre-S2 region, and wherein said modified hepatitis B virus large surface protein is further characterized by at least one modification selected from the group consisting of:

at least one of the protease sensitive sites at Arg100, Arg137, Gly149, or Arg167 is modified or deleted;

a myristylation site at amino acid residue 13 is lacking;

at least one of the glycosylation sites at amino acid residue 123, 124, or 125 is modified or deleted;

and a human serum albumin binding site at amino acids 120–132 of the naturally occurring pre-S2 region is lacking.

7. A method of producing simultaneously a) a modified hepatitis B virus large surface protein comprising an amino acid sequence lacking amino acids 1–11 of naturally occurring L protein, containing at least amino acids 21–47 of the naturally occurring pre-S1 region, and containing at least amino acids 133–145 of the pre-S2 region, wherein said modified hepatitis B virus large surface protein is further characterized by at least one modification selected from the group consisting of:

at least one of the protease sensitive sites at Arg100, Arg137, Gly149, or Arg167 is modified or deleted;

a myristylation site at amino acid residue 13 is lacking;

at least one of the glycosylation sites at amino acid residue 123, 124, or 125 is modified or deleted;

and a human serum albumin binding site at amino acids 120–132 of the naturally occurring pre-S2 region is lacking; and b) the S protein of Hepatitis B surface antigen, wherein said method comprises (i) culturing a cell transformed with a recombinant vector comprising a DNA coding sequence for expression of said modified L protein, and a recombinant vector capable of expressing the S protein of Hepatitis B surface antigen; and (ii) isolating from the cell lysate or extract of said culture protein particles of mixed subunit composition.

8. A recombinant DNA molecule comprising a DNA coding sequence for expression of a modified L protein operatively linked to a regulatory sequence, wherein said modified L protein is lacking amino acids 1–11 of naturally occurring L protein, containing at least amino acids 21–47 of the naturally occurring pre-S1 region, and containing at least amino acids 133–145 of the pre-S2 region, wherein at least one of the protease sensitive sites at Arg100, Arg137, Gly149, or Arg167 is modified or deleted.

9. A recombinant DNA molecule comprising a DNA coding sequence for expression of a modified L protein operatively linked to a regulatory sequence, wherein said modified L protein is lacking amino acids 1–11 of naturally occurring L protein, containing at least amino acids 21–47 of the naturally occurring pre-S1 region, and containing at least amino acids 133–145 of the pre-S2 region, wherein a myristylation site at amino acid 13 is lacking.

10. A recombinant DNA molecule comprising a DNA coding sequence for expression of a modified L protein operatively linked to a regulatory sequence, wherein said modified L protein is lacking amino acids 1–11 of naturally occurring L protein, containing at least amino acids 21–47 of the naturally occurring pre-S1 region, containing at least amino acids 133–145 of the pre-S2 region, and lacking the human serum albumin site at amino acids 120–132 of the naturally occurring pre-S2 region.

11. A recombinant DNA molecule comprising a DNA coding sequence for expression of a modified L protein operatively linked to a regulatory sequence, wherein said modified L protein is lacking amino acids 1–11 of naturally occurring L protein, containing at least amino acids 21–47 of the naturally occurring pre-S1 region, and containing at least amino acids 133–145 of the pre-S2 region, wherein at least one of the glycosylation sites at amino acid residue 123, 124, or 125 is modified or deleted.

12. A recombinant DNA molecule comprising a DNA coding sequence for expression of a modified L protein, which is operatively linked to a regulatory sequence, wherein the modified L protein is lacking amino acids 1–11 of the naturally occurring L protein, containing at least amino acids 21–47 of the naturally occurring pre-S1 region, further lacking amino acids 120–132 of the naturally occurring pre-S2 region, and further containing at least amino acids 133–145 of the pre-S2 region, wherein at least one of the protease sensitive sites at Arg100, Arg137, Gly149, or Arg167 is modified or deleted.

13. A recombinant DNA molecule comprising a DNA coding sequence for expression of a modified L protein, which is operatively linked to a regulatory sequence, wherein said modified L protein lacks amino acids 1–11 of the pre-S1 region, contains at least amino acids 12–52 of the pre-S1 region, contains at least 133–145 of the pre-S2 region, and contains at least amino acids 175–400 of the S protein.

14. A recombinant DNA molecule comprising a DNA coding sequence for expression of a modified L protein, which is operatively linked to a regulatory sequence, wherein said modified L protein lacks amino acids 1–11 and 13 of the pre-S1 region, contains at least amino acids 12 and 14–52 of the pre-S1 region, contains at least 133–145 of the pre-S2 region, and contains at least amino acids 175–400 of the S protein.

15. A vector comprising the recombinant DNA molecule of any one of claims 8–14.

16. A host cell transformed with the vector of claim 15.

17. A method for producing a modified hepatitis B virus L protein comprising inserting the recombinant DNA molecule of any one of claims 8–14 into a suitable expression vector, transferring the vector with said inserted DNA into an appropriate host, and expressing the modified L protein.

* * * * *